United States Patent [19]
Nanba et al.

[11] Patent Number: 6,069,149
[45] Date of Patent: May 30, 2000

[54] AMIDE DERIVATIVES AND INTERMEDIATES FOR THE SYNTHESIS THEREOF

[75] Inventors: Ryouichi Nanba; Takao Iizuka; Takeo Ishii, all of Kanagawa, Japan

[73] Assignee: Terumo Kabushiki Kaisha, Tokyo, Japan

[21] Appl. No.: 09/171,521

[22] PCT Filed: Jan. 6, 1998

[86] PCT No.: PCT/JP98/00005

§ 371 Date: Nov. 23, 1998

§ 102(e) Date: Nov. 23, 1998

[87] PCT Pub. No.: WO98/30562

PCT Pub. Date: Jul. 16, 1998

[30] Foreign Application Priority Data

Sep. 1, 1997 [JP] Japan ..................................... 9-002375

[51] Int. Cl.$^7$ ....................... A61K 31/437; C07D 471/02
[52] U.S. Cl. ............................................... 514/293; 546/82
[58] Field of Search ................. 546/82; 514/293

[56] References Cited

U.S. PATENT DOCUMENTS

| | | | |
|---|---|---|---|
| 4,698,338 | 10/1987 | Katner | 514/206 |
| 4,698,348 | 10/1987 | Gerster | 514/293 |
| 4,929,624 | 5/1990 | Gerster et al. | 514/293 |
| 4,988,815 | 1/1991 | Andre et al. | 546/159 |
| 5,037,986 | 8/1991 | Gerster | 546/82 |
| 5,266,575 | 11/1993 | Gerster et al. | 514/293 |
| 5,268,376 | 12/1993 | Gester | 514/293 |
| 5,346,905 | 9/1994 | Gerster | 514/293 |
| 5,389,640 | 2/1995 | Gerster et al. | 514/293 |
| 5,552,612 | 9/1996 | Katayama et al. | 250/506 |
| 5,605,899 | 2/1997 | Gerster et al. | 514/232.8 |
| 5,741,909 | 4/1998 | Gerster et al. | 546/82 |
| 5,756,747 | 5/1998 | Gerster | 514/82 |

FOREIGN PATENT DOCUMENTS

| | | |
|---|---|---|
| 60-123488 | 7/1985 | Japan . |
| 9-208854 | 1/1997 | Japan . |
| 9-208574 | 8/1997 | Japan . |

*Primary Examiner*—Alan L. Rotman
*Assistant Examiner*—Rita Desai
*Attorney, Agent, or Firm*—Burns, Doane, Swecker & Mathis, LLP

[57] ABSTRACT

Novel compounds which are amide derivatives represented by general formula (I) and medicinal preparations containing the same having an eosinophilic infiltration inhibitory effect based on a potent interferon ($\alpha,\gamma$)-inducing activity and an exellent percutaneous absorbability and being efficacious in treating allergic inflammatory diseases such as atopic dermatitis, various tumors and viral diseases. In said formula, each symbol has the following meaning: $R_1$ and $R_2$: each lower alkyl, etc.; X and Y: independently representing each oxygen, $NR_4$, $CR_5$ etc. (wherein $R_4$ and $R_5$ independently represent each hydrogen, an aromatic group, etc.); Z: an aromatic ring or heterocycle; $R_3$: hydrogen, lower alkoxy, etc.; g, i and k: independently representing each an integer of from 0 to 6; h, i and l: independently representing each an integer of 0 or 1; m: an integer of from 0 to 5; and n: an integer of from 2 to 12.

4 Claims, No Drawings

6,069,149

AMIDE DERIVATIVES AND INTERMEDIATES FOR THE SYNTHESIS THEREOF

This is a national application of International Patent Application No. PCT/JP98/00005, filed on Jan. 6, 1998.

TECHNICAL FIELD

The present invention relates to novel amide derivatives that have a potent interferon ($\alpha,\gamma$)-inducing activity and excellent percutaneous absorbability and that are useful as therapeutic agents for various tumors, viral diseases, and particularly allergic skin diseases such as atopic dermatitis associated with eosinophilic leukocyte skin infiltration reaction, pharmaceutical preparations containing the compounds, and intermediates for synthesizing the compounds.

BACKGROUND ART

Interferon $\alpha$ and $\beta$ are peptides having an antineoplastic effect and an antiviral effect, and are used by intramuscular or subcutaneous injection for treating various tumors such as kidney cancer or multiple myeloma and viral diseases such as active chronic hepatitis type C Interferon $\gamma$ is used for treating tumors (kidney cancer). Since it also has a potent immunity controlling effect, its use for treating allergic diseases such as atopic dermatitis has been considered.

Conventional basic treatment of atopic dermatitis is external application of steroid agents and oral administration of antihistaminics or antiallergic agents. Other treatments include hyposensitization, allergen (mites, food) elimination, PUVA (psoralen long wavelength ultraviolet irradiation), and bacteria vaccine therapy. However, any of such treatments is not satisfactory. Particularly, steroid agents for external application show an immediate effect but cause side effects due to long-term continuous application, such as atrophy of skin, angiotelectasis, flush, purpura, and readily infectiosity. Recently, the treatment of atopic dermatitis is directed to therapy with cytokines whose mechanism of function is novel (Hidemi Nakagawa, Rinsho Meneki (Clinical Immunology) 27, (supple 16), 597–602 (1995), Sachiko Kobayashi et al., Rinsho Meneki (Clinical Immunology) 27, (supple 16), 603–609 (1995)). Patients with atopic dermatitis has imbalance between Th1 helper cells and Th2 helper cells. In other words, Th2 helper cells are dominant. The promising tentative theory is that increased production of cytokines such as interleukin-4 and interleukin-5 from Th2 cells promotes IgE production and differentiation, proliferation, and infiltration of phlogocytes such as eosinophilic leukocytes to thereby induce inflammation. Generally, application of an antigen to sensitized human skin, it causes skin reaction that becomes maximum immediately and 4 to 8 hours after the application and lasts 24 to 48 hours thereafter. The former reaction is called immediate reaction (associated with IgE-mast cell) and the latter is called late allergic reaction. Particularly, it is said that the late reaction is closely related to symptom of allergic diseases including asthma. The mechanism of the late reaction has not been clarified. It is now considered as late phase reaction of the type I allergy associated with IgE-mast cells and is closely connected with infiltration of eosinophilic leukocytes due to dominance of Th2 helper cells (Motohiro Kurosawa, Rinsho Meneki (Clinical Immunology) 27(5), 564–574, 1995). The balance between Th1 helper cells and Th2 helper cells are regulated by interferon. Interferon $\gamma$ enhances differentiation of Th0 cells to Th1 cells. Attempts have been made to use interferon $\gamma$, which corrects dominance of Th2 cells, for therapy of atopic dermatitis. The main interferon treatment is subcutaneous injection of recombinant interferon $\gamma$ (Hanifin J. M., J. Am. Dermatol. 28, 189–197, 1993, Nishioka K. et al., J. Dermatol. 22(3), 181–185, 1995). It was reported that this treatment improved skin conditions and decreased the number of eosinophilic leukocytes in blood. Since interferon has an immunity potentiating effect, it does not cause side effects of readily-infectiosity, which is often caused by treatment with steroids. However, it is expensive and causes other side effects (fervescene, cold-like symptoms, headache). Thus, it cannot be a satisfactory medicine. This is not only applied to the case that interferon is used for treating atopic dermatitis but also the case that it is used as an antiviral or an antitumor agent in the form of injection.

When interferon is administered from the outside of the body, it has still other problems. It can be expected to solve the problems of the interferon injection (cost and side effects) by topical application (external application) of a low molecular weight synthetic compound as an interferon inducer. Several interferon-inducing compounds are known. For example, the known compounds include some 1-substituted-1H-imidazo[4,5-c]quinoline-4-amine compounds, represented by 1-isobutyl-1H-imidazo[4,5-c]quinoline-4-amine (Imiquimod), which is an antiviral agent (European Patent No. 145340, U.S. Pat. No. 4,689,338, U.S. Pat. No. 4,698,348, U.S. Pat. No. 4,929,624, European Patent No. 385630, U.S. Pat. No. 5,346,905, etc.). Some of them are under clinical test as an external preparation. Since these are used to treat genital wart (Imiquimod, Pharma Projects 1996), their percutaneous absorbability is expected to be poor. They also show low interferon-inducing activity in humans.

Therefore, an objective of the present invention is to provide a novel compound that has an eosinophilic leukocyte infiltration-inhibiting effect based on a potent interferon ($\alpha,\gamma$)-inducing activity and excellent percutaneous absorbability, causes fewer side effects, and thus effective for allergic inflammatory diseases such as atopic dermatitis, various tumors, and viral diseases, and a medicinal preparation containing the same.

DESCRIPTION OF THE INVENTION

The present invention that solves the above problems is as follows:

(1) an amide derivative represented by the following formula I and its pharmaceutically acceptable acid addition salt:

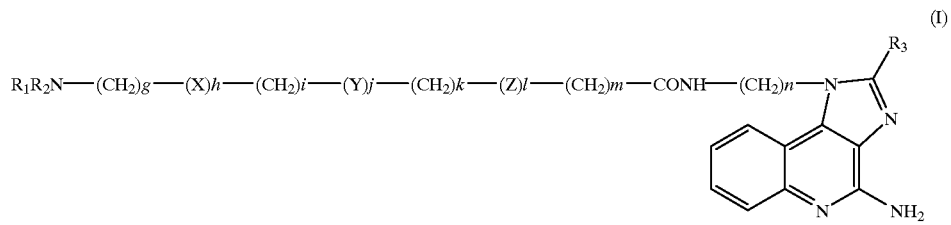

(I)

where in the fomula I, $R_1$ and $R_2$ represent an alkyl group having 1 to 6 carbon atoms that may be branched and may form a ring together, or one of them may form a ring together with any atom in X, Y, or the methylene chain, X and Y independently represents an oxygen atom, S(O)p, wherein p is an integer of 0 to 2, $NR_4$, $CR_5=CR_6$, $CR_7R_8$, or phenylene group that may be substituted, wherein $R_4$, $R_5$, $R_6$, $R_7$, and $R_8$ independently represents an hydrogen atom, a lower alkyl group, a hydroxyl group, a lower alkoxyl group, an amino group, a mono- or di-lower alkyl substituted amino group, a carboxyl group, a lower alkoxycarbonyl group, aromatic ring group that may be substituted, or heterocyclic ring group that may be substituted, Z represents an aromatic ring or a heterocyclic ring, which may be substituted with a lower alkyl group, a hydroxyl group, a lower alkoxy group, or halogen, $R_3$ represents a hydrogen atom, phenyl group that may be substituted, a lower alkyl group that may be substituted with a phenyl group, a phenoxy group, a benzyloxy group, a lower alkoxy group, an amino group, a mono- or di-lower alkyl substituted amino group, a carboxyl group, or a lower alkoxycarbonyl group, g, i, and k independently represents an integer of 0 to 6, h, j, and l independently represents 0 or 1, m represents an integer of 0 to 5, and n represents an integer of 2 to 12;

(2) a medicinal preparation comprising the amide derivative of (1) above;

(3) an intermediate represented by the following formula II for synthesizing the amide derivative of formula I:

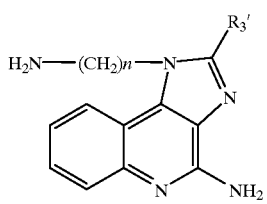

(II)

where in the formula II, $R_3$ represents phenyl group that may be substituted, a lower alkyl group that may be substituted with a phenyl group, a phenoxy group, a benzyloxy group, a lower alkoxy group, an amino group, a mono- or di-lower alkyl substituted amino group, a carboxyl group, or a lower alkoxycarbonyl group, and n represents an integer of 2 to 12;

(4) an intermediate represented by the following formula III for synthesizing the amide derivative of formula I:

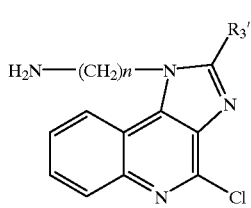

(III)

where in the formula III, $R_3$' represents a phenyl group that may be substituted, a lower alkyl group that may be substituted with a phenyl group, a phenoxy group, a benzyloxy group, a lower alkoxy group, an amino group, a mono- or di-lower alkyl substituted amino group, a carboxyl group, or a lower alkoxycarbonyl group, and n represents an integer of 2 to 12;

(5) an intermediate represented by the following formula IV for synthesizing the amide derivative of formula I:

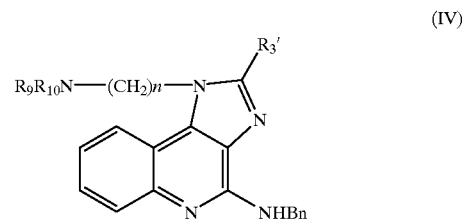

(IV)

where in the formula IV, when $R_9$ is a hydrogen atom, $R_{10}$ represents an alkanoyl group having 1 to 8 carbon atoms of a carbon chain that may have a branched chain, a haloalkanoyl group having 1 to 8 carbon atoms of a carbon chain that may have a branched chain, a phenylalkanoyl group having 1 to 8 carbon atoms of a carbon chain, whose benzene ring may be substituted with halogen, a nitro group, or a methoxy group, a phenoxyalkanoyl group having 1 to 8 carbon atoms of a carbon chain, whose benzene ring may be substituted with halogen, a nitro group, or a methoxy group, an alkoxycarbonyl group having 1 to 8 carbon atoms of a carbon chain that may have a branched chain, a haloalkoxycarbonyl group having 1 to 8 carbon atoms of a carbon chain that may have a branched chain, or a phenylalkoxycarbonyl group having 1 to 8 carbon atoms of a carbon chain, whose benzene ring may be substituted with halogen, a nitro group, or a methoxy group, $R_9$ and $R_{10}$ may form an aromatic cyclic imide together that may be substituted with halogen, a nitro group or a methoxy group, $R_3$ represents a phenyl group that may be substituted, a lower alkyl group that may be substituted with a phenyl group, a phenoxy group, a benzyloxy group, a lower alkoxy group, an amino group, a mono- or di-lower alkyl substituted amino group, a carboxyl group, or a lower alkoxycarbonyl group, and n represents an integer of 2 to 12;

(6) an intermediate represented by the following formula V for synthesizing the amide derivative of formula I:

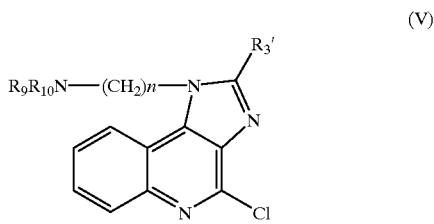

(V)

where in the formula V, when $R_9$ is a hydrogen atom, $R_{10}$ represents an alkanoyl group having 1 to 8 carbon atoms of a carbon chain that may have a branched chain, a haloalkanoyl group having 1 to 8 carbon atoms of a carbon chain that may have a branched chain, a phenylalkanoyl group having 1 to 8 carbon atoms of a carbon chain, whose benzene ring may be substituted with halogen, a nitro group, or a methoxy group, a phenoxyalkanoyl group having 1 to 8 carbon atoms of a carbon chain, whose benzene ring may be substituted with halogen, a nitro group, or a methoxy group, an alkoxycarbonyl group having 1 to 8 carbon atoms of a carbon chain that may have a branched chain, a haloalkoxycarbonyl group having 1 to 8 carbon atoms of a carbon chain that may have a branched chain, or a phenylalkoxycarbonyl group having 1 to 8 carbon atoms of a carbon chain, whose benzene ring may be substituted with halogen, a nitro group, or a methoxy group, $R_9$ and $R_{10}$ may form an aromatic cyclic imide together that may be substituted with halogen, a nitro group or a methoxy group, $R_3$ ' represents a phenyl group that may be substituted, a lower alkyl group that may be substituted with a phenyl group, a phenoxy group, a benzyloxy group, a lower alkoxy group, an amino group, a mono- or di-lower alkyl substituted amino group, a carboxyl group, or a lower alkoxycarbonyl group, and n represents an integer of 2 to 12;

(7) an intermediate represented by the following formula VI for synthesizing the amide derivative of formula I:

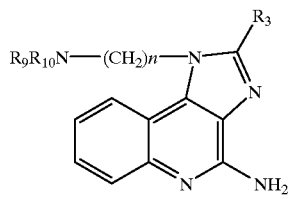

(VI)

where in the formula VI, when $R_9$ is a hydrogen atom, $R_{10}$ represents an alkanoyl group having 1 to 8 carbon atoms of a carbon chain that may have a branched chain, a haloalkanoyl group having 1 to 8 carbon atoms of a carbon chain that may have a branched chain, a phenylalkanoyl group having 1 to 8 carbon atoms of a carbon chain, whose benzene ring may be substituted with halogen, a nitro group, or a methoxy group, a phenoxyalkanoyl group having 1 to 8 carbon atoms of a carbon chain, whose benzene ring may be substituted with halogen, a nitro group, or a methoxy group, an alkoxycarbonyl group having 1 to 8 carbon atoms of a carbon chain that may have a branched chain, a haloalkoxycarbonyl group having 1 to 8 carbon atoms of a carbon chain that may have a branched chain, or a phenylalkoxycarbonyl group having 1 to 8 carbon atoms of a carbon chain, whose benzene ring may be substituted with halogen, a nitro group, or a methoxy group, $R_9$ and $R_{10}$ may form an aromatic cyclic imide together that may be substituted with halogen, a nitro group or a methoxy group, $R_3$ represents a hydrogen atom, a phenyl group that may be substituted, a lower alkyl group that may be substituted with a phenyl group, a phenoxy group, a benzyloxy group, a lower alkoxy group, an amino group, a mono- or di-lower alkyl substituted amino group, a carboxyl group, or a lower alkoxycarbonyl group, and n represents an integer of 2 to 12;

(8) an intermediate represented by the following formula VII for synthesizing the amide derivative of formula I:

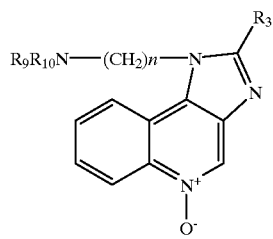

(VII)

where in the formula VII, when $R_9$ is a hydrogen atom, $R_{10}$ represents an alkanoyl group having 1 to 8 carbon atoms of a carbon chain that may have a branched chain, a haloalkanoyl group having 1 to 8 carbon atoms of a carbon chain that may have a branched chain, a phenylalkanoyl group having 1 to 8 carbon atoms of a carbon chain, whose benzene ring may be substituted with halogen, a nitro group, or a methoxy group, a phenoxyalkanoyl group having 1 to 8 carbon atoms of a carbon chain, whose benzene ring may be substituted with halogen, a nitro group, or a methoxy group, an alkoxycarbonyl group having 1 to 8 carbon atoms of a carbon chain that may have a branched chain, a haloalkoxycarbonyl group having 1 to 8 carbon atoms of a carbon chain that may have a branched chain, or a phenylalkoxycarbonyl group having 1 to 8 carbon atoms of a carbon chain, whose benzene ring may be substituted with halogen, a nitro group, or a methoxy group, $R_9$ and $R_{10}$ may form an aromatic cyclic imide together that may be substituted with halogen, a nitro group or a methoxy group, $R_3$ represents a hydrogen atom, a phenyl group that may be substituted, a lower alkyl group that may be substituted with a phenyl group, a phenoxy group, a benzyloxy group, a lower alkoxy group, an amino group, a mono- or di-lower alkyl substituted amino group, a carboxyl group, or a lower alkoxycarbonyl group, and n represents an integer of 2 to 12;

(9) an intermediate represented by the following formula VIII for synthesizing the amide derivative of formula I:

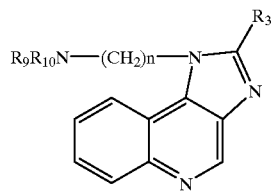

(VIII)

where in the formula VIII, when $R_9$ is a hydrogen atom, $R_{10}$ represents an alkanoyl group having 1 to 8 carbon atoms of a carbon chain that may have a branched chain, a haloalkanoyl group having 1 to 8 carbon atoms of a carbon chain that may have a branched chain, a phenylalkanoyl group having 1 to 8 carbon atoms of a carbon chain, whose benzene ring may be substituted with halogen, a nitro group, or a methoxy group, a phenoxyalkanoyl group having 1 to 8 carbon atoms of a carbon chain, whose benzene ring may be substituted with halogen, a nitro group, or a methoxy group, an alkoxycarbonyl group having 1 to 8 carbon atoms of a carbon chain that may have a branched chain, a haloalkoxycarbonyl group having 1 to 8 carbon atoms of a carbon chain that may have a branched chain, or a phenylalkoxycarbonyl group having 1 to 8 carbon atoms of a carbon chain, whose benzene ring may be substituted with halogen, a nitro group, or a methoxy group, $R_9$ and $R_{10}$ may form an aromatic cyclic imide together that may be substituted with halogen, a nitro group or a methoxy group, $R_3$ represents a hydrogen atom, a phenyl group that may be substituted, a lower alkyl group that may be substituted with a phenyl group, a phenoxy group, a benzyloxy group, a lower alkoxy group, an amino group, a mono- or di-lower alkyl substituted amino group, a carboxyl group, or a lower alkoxycarbonyl group, and n represents an integer of 2 to 12; and

(10) an intermediate represented by the following formula IX for synthesizing the amide derivative of formula I:

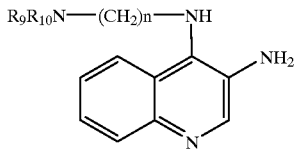

(IX)

where in the formula IX, when $R_9$ is a hydrogen atom, $R_{10}$ represents an alkanoyl group having 1 to 8 carbon atoms of a carbon chain that may have a branched chain, a haloalkanoyl group having 1 to 8 carbon atoms of a carbon chain that may have a branched chain, a phenylalkanoyl group having 1 to 8 carbon atoms of a carbon chain, whose benzene ring may be substituted with halogen, a nitro group, or a methoxy group, a phenoxyalkanoyl group having 1 to 8 carbon atoms of a carbon chain, whose benzene ring may be substituted with halogen, a nitro group, or a methoxy group, an alkoxycarbonyl group having 1 to 8 carbon atoms of a carbon chain that may have a branched chain, a haloalkoxycarbonyl group having 1 to 8 carbon atoms of a carbon chain that may have a branched chain, or a phenylalkoxycarbonyl group having 1 to 8 carbon atoms of a carbon chain, whose benzene ring may be substituted with halogen, a nitro group, or a methoxy group, $R_9$ and $R_{10}$ may form an aromatic cyclic imide together that may be substituted with halogen, a nitro group or a methoxy group, and n represents an integer of 2 to 12.

In formulae IV, V, VI, VII, VIII, and IX, $R_9$ and $R_{10}$ are protective groups of an amino group and prefered exemples include acetyl, propionyl, pivaloyl, benzoyl, methoxycarbonyl, ethoxycarbonyl, iso-butoxycarbonyl, tert-butoxycarbonyl, benzyloxycarbonyl, phthalimide, etc. The pharmaceutically acceptable acid addition salts of the compound of formula I include salts of mineral acids such as hydrochloric acid, hydrobromic acid, sulfuric acid, nitric acid, or phosphoric acid, and organic acids such as acetic acid, lactic acid, maleic acid, fumaric acid, citric acid, malic acid, tartaric acid, oxalic acid, methanesulfonic acid, or p-toluenesulfonic acid. These can be prepared by a conventional method.

The novel amide derivatives of the present invention represented by formula I can be produced by, for example, the following reaction scheme:

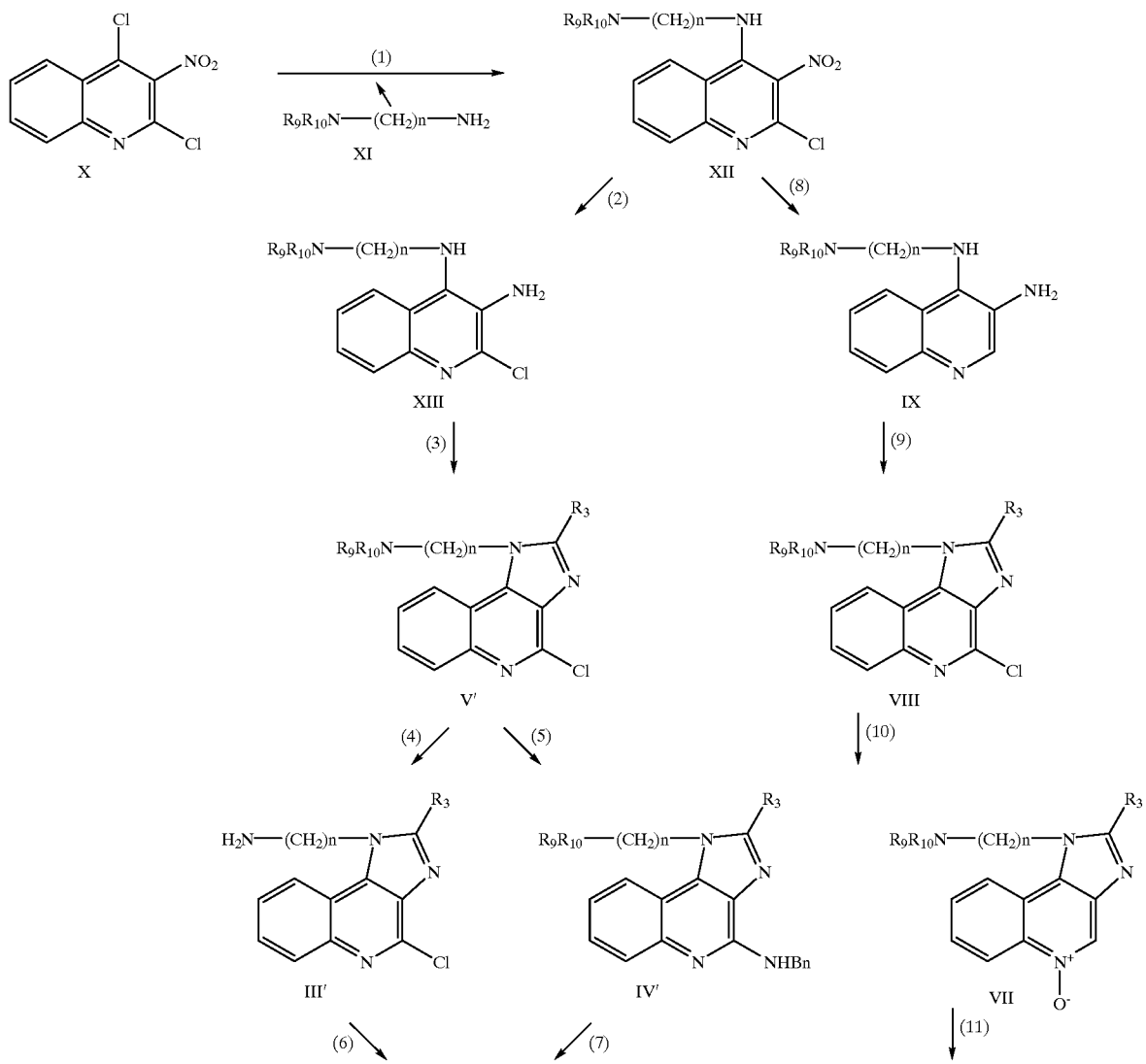

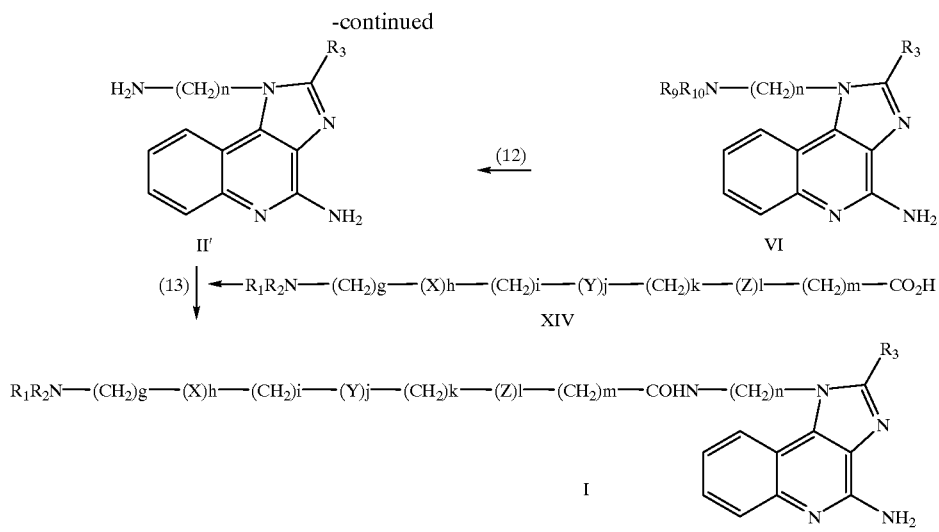

In the step (1), 2,4-dichloro-3-nitroquinoline of formula X, which is a starting compound, is known and can be synthesized by the method of Gaburiel (Chem. Ber., 1918, 51, 1500), etc. The monoamino-protected form of alkylene diamine represented by formula XI can also be synthesized by a known method (Synth. Commun., 1990, 20, 2559, J. Med. Chem., 1988, 31, 898, J. Org. Chem., 1981, 46, 2455, J. Amer. Chem. Soc., 1941, 63, 852, etc.). The compound of formula X is reacted with the compound of formula XI by heating in an appropriate solvent (preferably a basic solvent such as triethylamine or pyridine) to obtain the compound of formula XII. Alternatively, alkylene diamine in place of the compound of formula XI is reacted with the compound of formula X and a primary amino group of the resulting product is protected to produce the compound of formula XII.

In the step (2), the nitro group can be reduced with iron powder-hydrochloric acid or tin chloride (II) in an appropriate solvent (preferably alcohol) at 0° C. to a reflux temperature. Alternatively, the compound of formula XIII can be obtained by contact reduction reaction by hydrogen in the presence of a catalyst such as palladium or platinum.

In the step (3), the compound of formula V' can be obtained by heating the compound of formula XIII in the presence of carboxylic acid represented by $R_3CO_2H$ (wherein $R_3$ is as defined above) or ortho ester of carboxylic acid represented by $R_3C(OR_{11})_3$ (wherein $R_3$ is as defined above and $R_{11}$, represents a lower alkyl group) without solvent or in an appropriate solvent (for example, benzene, toluene, xylene, etc.).

In the step (4), appropriate reaction conditions for deprotection of the amino-protective group of the compound of formula V' can be selected depending on the type of the protective group. For example, the compound of formula III' can be obtained by using trifluoroacetic acid in an appropriate solvent when the protective group is tert-butoxycarbonyl (Boc) and by using hydrobromide-acetic acid when the protective group is benzyloxycarbonyl (Z).

In the step (5), the compound of formula V' is heated with benzylamine in an appropriate solvent or with an excess amount of benzylamine without a solvent to obtain the compound of formula IV'.

In the step (6), the compound of formula III' is reacted with ammonia in an alcoholic solvent or concentrated aqueous ammonium under heating in an autoclave (pressure-resistant steel cylinder) to obtain the compound of II'.

In the step (7), the compound of formula II' can be obtained by heating the compound in carboxylic acid (preferably formic acid) with palladium hydroxide on a carbon carrier. In this case, when the protection group of N represented by $R_9$ and $R_{10}$ is remained, deprotection is further performed in the same manner as in the step (4).

In the step (8), reduction of the nitro group and dechlorination can be performed by contact hydrogenation in the presence of an appropriate catalyst such as palladium or platinum.

The step (9) can be performed in the same manner as in the step (3).

In the step (10), the formation of an N-oxide can be perfomed with peracid or hydrogen peroxide in an appropriate solvent (preferably acetic acid or lower alcohol) at an appropriate temperature (for example, 0° C. to a reflux temperature of the solvent).

In the step (11), the N-oxide compound of formula VII is reacted with an acylating agent (preferably p-toluenesulfonyl chloride, benzenesulfonyl chloride, and methanesulfonyl chloride) and an aminating agent (for example, concentrated aqueous ammonium, ammonium carbonate, etc.) in an appropriate solvent (for example, dichloromethane, chloroform, toluene, etc.) at an appropriate temperature (for example, −20° C. to a reflux temperature of the solvent) to obtain the compound of formula VI.

The step (12) can be performed in the same manner as in the step (4).

In the step (13), a reaction between the compound of formula XIV and the compound of formula II' can be performed to be led to the compound of formula I, which is performed by condensation in the presence of an appropriate condensing agent by an appropriate condensation method (for example, the carbodiimide method, the acid anhydride mixture method, the acid chloride method, etc.), in an appropriate solvent (for acetonitrile, alcohol, water, etc.).

4-Chloro-3-nitroquinoline can be used as a starting compound in place of the compound of formula X (2,4-dichloro-3-nitroquinoline). This compound can be readily obtained by a known method (U.S. Pat. No. 3,700,674) and the compound of formula IX can be led through the steps (1) and (8).

The synthetic intermediates represented by formula XIV are mostly novel compounds; some of them are known compounds.

The synthetic intermediates represented by formula XIV are mostly novel compounds; some of them are known compounds. These can be readily produced by methods of usual organic synthetic chemistry. For example, when X in formula XIV is O, S(O)p (wherein p has the same meaning as defined above) or N $R_4$ ($R_4$ has the same meaning as defined above), the compound of formula XV, wherein M is a leaving group (for example, halogen, methanesulfonyloxy, p-toluenesulfonyloxy, etc.) and $R_1$, $R_2$, and g have the same meaning as defined above, is reacted with the compound of formula XVI, wherein $R_2$ represents hydrogen or a lower alkyl group, i, j, k, l, and m have the same meaning as defined above, in the presence of an appropriate base in an appropriate solvent, and then, the synthetic intermediates are obtained by, if necessary, hydrolyzing the ester moiety of the resulting product. Similarly, the desired compound can be obtained by reacting the compound of formula XVII, wherein $R_1$, $R_2$, and g have the same meaning as defined above, with the compound of formula XVIII, wherein M represents a leaving group (for example, halogen, methanesulfonyloxy, p-toluenesulfonyloxy, etc.), $R_{12}$ represents hydrogen or a lower alkyl group, and i, j, k, l, and m have the same meaning as defined above.

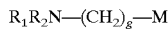

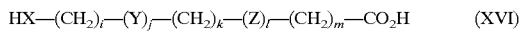

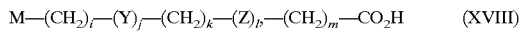

For example, when Y in formula XIV is $CH=CR_6$, wherein $R_6$ has the same meaning as defined above, and K is 0, the desired compound can also be obtained by reacting the compound of formula XIX, wherein L represents halogen, and $R_1$, $R_2$, g, h, and i have the same meaning as defined above, with the compound of formula XX, wherein $R_{12}$ represents hydrogen or a lower alkyl group, and $R_6$, l, and m have the same meaning as defined above, in the presence of an appropriate base in an appropriate solvent, and then, if necessary by hydrolyzing, the ester moiety of the resulting product. Alternatively, a Grignard reagent represented by formula XXI, wherein L is halogen and $R_6$ has the same meaning as defined above, is reacted with the compound of formula XXII, wherein $R_{12}$ represents hydrogen or a lower alkyl group, and $R_1$, $R_2$, g, h, i, l, and m have the same meaning as defined above, and the resulting product is dehydrated with acid or the like, if necessary, followed by hydrolyzing the ester moiety to obtain the desired compound.

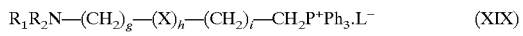

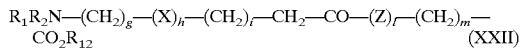

Examples of the appropriate solvents as described above include N,N-dimethylformamide, dimethylsulfoxide, chloroform, methylene chloride, benzene, toluene, xylene, tetrahydrofuran, dioxane, diethyl ether, acetonitrile, alcohol, and water. The appropriate base includes, for example, sodium hydrogencarbonate, potassium carbonate, triethylamine, pyridine, sodium hydride, metal sodium, t-butoxy potassium, and n-butyl lithium. The starting compounds represented by formulae XV, XVI, XVII, XVIII, XIX, XX, XXI, and XXII are commerically available compounds, known compounds, or novel compounds that can be readily synthesized by known methods. As described above, the synthetic intermediates represented by formula XIV can be readily synthesized by the combination of known reactions. The compounds of formula XIV can be isolated in the form of a salt (for example, hydrochloride, hydrobromide, an organic acid salt, etc.), which is subjected to the reaction of the step (8).

Many of the amide derivatives represented by formula I and their salts of the present invention are racemic mixtures, which have an asymmetric carbon atom in the molecule. If required, the respective optically active compounds can be used after isolated by optical resolution, asymmetric synthesis or the like methods.

The term "lower alkyl" used herein means an alkyl group having 1 to 8 carbon atoms of a carbon chain that may be a branched chain or may form a ring.

The amide derivatives represented by formula I or pharmaceutically acceptable acid addition salts thereof of the present invention can be orally or parenterally administered to mammalian animals as a therapeutic agent for atopic dermatitis. The dosage form of the pharmaceutical composition for oral administration includes tablets, capsules, powders, fine powders, granules, suspension, emulsion, liquid, and syrup. The dosage form for parenteral administration includes injections, suppositories, inhalants, ophthalmic solution, collunarium, ointments, cream, lotion, and patches. Into any of the above dosage forms, appropriate medically and acceptable additives can be added upon formulation. Examples of the additives include excipients, binders, lubricants, disintegrating agents, diluents, flavors, colorants, dissolving agents, suspension media, emulsifiers, preservatives, buffering agents, isotonizing agents, ointment base, oils, dissolving adjuvants, absorbefacients, adhesives, and atomizing media. Since the compounds of formula I and their acid addition salts are excellent in percutaneous absorbability, it is preferably formulated into compositions for percutaneous administration such as ointments, lotion, or cream.

The compounds of formula I and their acid addition salts show an eosinophilic leukocyte infiltration surpressing activity. They are thus suggested to be useful for therapy of other diseases, for which the activity is effective, such as allergic rhinitis, urticaria, pemphigoid, eosinophilic pustular folliculitis, and asthma. Furthermore, since they strongly induce interferon α and γ, they are useful for therapy of various cancerous diseases such as multiple myeloma, kidney cancer, malignant ecphyma, urinary bladder cancer, hairy cell leukemia, or chlonic myelocytic leukemia, and chlonic rheumatism. They are also useful for various viral diseases such as active chronic hepatitis types B and C, herpes simplex keratitis, genital wart, condyloma acuminatum, herpes zoster, AIDS.

BEST MODE FOR IMPLEMENTING THE INVENTION

The present invention will be described below in more detail with reference to examples. Spectroscopic data of the compounds synthesized in the examples were measured with Nippon Bunko IR-810 or FT/IR-350 for IR spectra and with Varian Unity 400 NMR Apparatus for 1H-NMR spectra.

PRODUCTION EXAMPLE 1

α-(2-dimethylaminoethoxy)-α-phenyl-p-toluic acid (1) 25.2 g (154 mmol) of methyl terephthalaldehydate was dissolved in 200 ml of tetrahydrofuran. 51.2 ml(154 mmol) of a 2M ether solution of phenyl magnesium bromide was added dropwise thereto under cooling in a sodium chloride-ice bath with stirring for 12 minutes and the mixture was stirred for further 20 minutes. Dilute hydrochloric acid was added to the resulting reaction mixture, then the obtained mixture was extracted twice with ethyl acetate. After the organic phase was washed with brine and dried (MgSO$_4$), the solvent was distilled off. The resulting residue was purified by silica gel column chromatography (n-hexane:ethyl acetate=6:1 (v/v)) to obtain 31.7 g (131 mmol) of methyl α-hydroxy-α-phenyl-p-toluate as a pale yellow oily substance. Its spectroscopic data are as follows:
$^1$H-NMR (CDCl$_3$) δ(ppm): 2.32 (1H, br), 3.90 (3H, s), 5.89 (1H, s), 7.26~7.38 (5H, m), 7.47 (2H, d, J=8.0 Hz), 8.00 (2 H, d, J=8.4 Hz).

(2) 4.66 g (19.23 mmol) of methyl α-hydroxy-α-phenyl-p-toluate was dissolved in 50 ml of N,N-dimethylformamide. 0.77 g (19.23 mmol) of 60% sodium hydride was added thereto and the mixture was stirred at room temperature for 1 hour. 3.10 g (28.85 mmol) of 2-dimethylaminoethyl chloride was added thereto and the mixture was heated at 80° C. for 2.5 hours. After the reaction mixture was cooled and poured into water, the obtained mixture was extracted twice with ethyl acetate and the extract was washed with brine, and dried (MgSO$_4$). The solvent was distilled off and the resulting residue was purified by silica gel column chromatography (chloroform:methanol=40:1 (v/v)) to obtain 0.53 g (1.69 mmol) of methyl α-(2-dimethylaminoethoxy)-α-phenyl-p-toluate as a brown oily substance. Its spectroscopic data are as follows:
$^1$H-NMR (CDCl$_3$) δ (ppm) 2.26 (6H, s), 2.60 (2H, t, J=6.0 Hz), 3.56 (2H, t d, J=6.0 Hz, 2.0 Hz), 3.89 (3H, s), 5.40 (1H, s), 7.22~7.35 (5H, m), 7.43 (2H, d, J=8.4 Hz), 7.98 (2H, d, J=8.0 Hz)

(3) 0.53 g (1.69 mmol) of methyl α-(2-dimethylaminoethoxy)-α-phenyl-p-toluate) was dissolved in 10 ml of methanol. 2.54 ml of a 1N sodium hydroxide aqueous solution was added thereto and the mixture was refluxed under heating for 1 hour. After the reaction mixture was cooled, 2.54 ml of 1N hydrochloric acid was added thereto and the mixture was concentrated to dryness. A mixture of chloroform and methanol (5:1 (v/v)) was added to the residue, and the resulting mixture was stirred for a while, then filtered with Celite. The solvent was distilled off and the residue was triturated with diethyl ether. The resulting precipitate was collected by filtration to obtain 0.44 g (1.47 mmol) of α-(2-dimethylaminoethoxy)-α-phenyl-p-toluic acid as pale yellow brown powder.

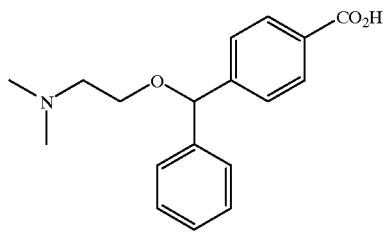

Its spectroscopic data are as follows:
$^1$H-NMR (CDCl$_1$) δ (ppm) 2.62 (6H, s), 3.00 (2H, m), 3.59 (1H, m), 3.82 (1H, m), 5.37 (1H, s), 7.21~7.36 (7H, m), 7.77 (2H, d, J=8.4 Hz).

PRODUCTION EXAMPLE 2
3-{4-[α-(2-Dimethylaminoethoxy)benzyl]phenyl}propionic acid (1) 30 ml of 10% hydrochloride-methanol was added to 2.35 g (13.34 mmol) of 4-formylcinnamic acid and the mixture was stirred overnight. The solvent was distilled off under reduced pressure. The residue was di ssolved in ethyl acetate and the resulting solution was washed with sodium hydrogencarbonate and brine. The organic phase was dried (over MgSO$_4$) and the solvent was distilled off. The resulting residue was dissolved in 22 ml of tetrahydrofuran. 4.36 ml (13.09 mmol) of a 3M ether solution of phenyl magnesium bromide was added dropwise to the mixture for three minutes under cooling in a sodium chloride-ice bath and the resulting mixture was stirred for further 20 minutes. After 1N hydrochloric acid was added to the reaction mixture, the resulting mixture was extracted twice with ethyl acetate. The extract was washed with brine and dried (MgSO$_4$). The solvent was distilled off and the resulting residue was purified by silica gel column chromatography (n-hexane:ethyl acetate=8:1 to 4:1 (v/v)) to obtain 3.04 g (11.33 mmol) of methyl 4-(α-hydroxybenzyl)cinnamate as a faint yellow solid. Its spectroscopic data are as follows:
$^1$H-NMR (CDCl$_3$) δ(ppm) 2.27 (1H, d, J=3.2 Hz), 3.80 (3H, s), 5.85 (1H, d, J=3.6 Hz), 6.41 (1H, d, J=15.6 Hz), 7.2~7.39 (5H, m), 7.41 (2H, d, J=8.4 Hz), 7.49 (2H, d, J=8.4 Hz), 7.67 (1H, d, J=16.4 Hz).

(2) 3.04 g (11.33 mmol) of methyl 4-(α-hydroxybenzyl)cinnamate was dissolved in 35 ml of N,N-dimethylformamide, thereafter 0.45 g (11.33 mmol) of 60% sodium hydride was added thereto, and the mixture was stirred overnight at room temperature. 2.44 g ( 22.66 mmol) of 2-dimethylaminoethyl chloride was then added thereto. The resulting mixture was heated at 80° C. and stirred for 5 hours. After cooling, the reaction mixture was poured into water, the obtained mixture was extracted twice with ethyl acetate, and the extract was washed with brine. The organic phase was dried (MgSO$_4$) and the solvent was distilled off. The resulting residue was purified by silica gel column chromatography (chloroform:methanol =50:1 (v/v)) followed by alumina column chromatography (n-hexane:ethyl acetate=5:1 (v/v)) to obtain 0.19 g (0.560 mmol) of methyl 4-[α-(2-dimethylaminoethoxy)benzyl]cinnamate as a pale yellow oily substance. Its spectroscopic data are as follows:
$^1$H-NMR (CDCl$_3$) δ (ppm): 2.27 (6H, s), 2.60 (2H, t, J=6.0 Hz), 3.56 (2H, t, J=6.0 Hz), 3.79 (3H, s), 5.37 (1H, s), 6.40 (1H, d, J=16.4 Hz), 7.22~7.36 (5H, m), 7.37 (2H, d, J=8.0 Hz), 7.47 (2H, d, J=8.0 Hz), 7.66 (1H, d, J=16.0 Hz).

(3) 0.19 g (0.560 mmol) of methyl 4-[α-(2-dimethylaminoethoxy)benzyl]cinnamate was dissolved in 4 ml of methanol and 13 mg (0.056 mmol) of nickel chloride hexahydrate was then added. Forty-two mg (1.12 mmol) of sodium boronhydride was further added thereto under ice-cooling in divided portions for 1 hour and stirred for further 45 minutes. The reaction mixture was filtered and the filtrate was concentrated. The resulting residue was dissolved in chloroform and washed with water and brine. After the organic phase was dried (MgSO$_4$), the solvent was distilled off and the residue was purified by silica gel column chromatography (chloroform:methanol=50:1 (v/v)) to obtain 0.10 g (0.293 mmol) of methyl 3-{4-[α-(2-dimethylaminoethoxy)benzyl]phenyl}propionate as a colorless oily substance. Its spectroscopic data are as follows:
$^1$H-NMR (CDCl$_3$) δ (ppm): 2.26 (6H, s), 2.59 (2H, t, J=6.0 Hz), 2.60 (2H, t, J=7.8 Hz), 2.91 (2H, t, J=7.8 Hz), 3.55 (2H, t, J=6.2 Hz), 3.66 (3H, s), 5.33 (1H, s), 7.13 (2H, d, J=8.0 Hz), 7.20~7.36 (7H, m).

(4) 0.10 g (0.293 mmol) of methyl 3-{4-[α-(2-dimethylaminoethoxy)benzyl]phenyl} propionate (0.10 g, 0.293 mmol) was dissolved in 2.5 ml of methanol, 0.44 ml of a 1N sodium hydroxide aqueous solution was added, and the resulting mixture was stirred overnight at room temperature. 0.44 ml of 1N Hydrochloric acid was added to the reaction mixture and the obtaied mixture was concentrated to dryness. After a chloroform-methanol mixed solution (5:1 (v/v)) was added to the residue, the resulting mixture was stirred for a while and filtered with Celite. The filtrate was concentrated and the residue was purified by silica gel column chromatography (chloroform:methanol=4:1 (v/v)) to obtain 77 mg (0.235 mmol) of 3-{4-[α-(2-dimethylaminoethoxy)benzyl]phenyl}propionic (shown below) as a faint yellow gummy solid.

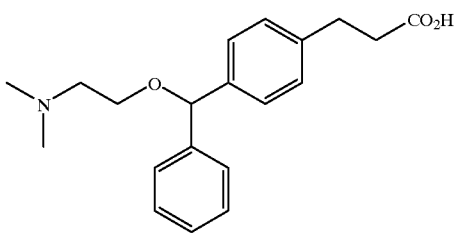

Its spectroscopic data are as follows:
$^1$H-NMR (CDCl$_3$) δ (ppm): 2.33 (2H, m), 2.49 (6H, s) 2.75 (2H, m), 2.86 (2H, m), 3.52 (1H, m), 3.66 (1H, m), 5.29 (1H, s), 7.13 (2H, d, J=8.0 Hz), 7.19~7.35 (7H, m).

PRODUCTION EXAMPLE 3

α-(2-dimethylaminoethoxy)-α-phenyl-m-toluic acid (1) 25 ml of 10% hydrogen chloride-methanol was added to 1.95 g (8.62 mmol) of 3-benzoylbenzoic acid and the mixture was stirred overnight at room temperature. The reaction mixture was concentrated under reduced pressure. The resulting residue was dissolved in ethyl acetate, washed with a sodium hydrogencarbonate aqueous solution and brine, and dried (MgSO$_4$). The solvent was distilled off and the residue was dissolved in 20 ml of methanol. Under ice-cooling, 0.32 g (8,41 mmol) of sodium boronhydride was added thereto and the mixture was stirred for 30 minutes. After acetone and 1N hydrochloric acid were added, the reaction mixture was extracted twice with chloroform, the extract was washed with a sodium hydrogencarbonate aqueous solution, and dried (MgSO$_4$). The solvent was distilled off to obtain 2.04 g (8.42 mmol) of methyl a-hydroxy-a-phenyl-m-toluate as a colorless oily substance. Its spectroscopic data are as follows:
$^1$H-NMR (CDCl$_3$) δ (ppm) : 2.30 (1H, d, J=3.6 Hz), 3.90 (3H, s), 5.90 (1H, d, J=3.6 Hz), 7.27~7.39 (5H, m), 7.41 (1H, t, J=7.8 Hz), 7.59 (1H, d, J=7.6 Hz), 7.94 (1H, d, J=7.6 Hz), 8.09 (1H, s).

(2) 0.48 g (1.53 mmol) of methyl α-(2-dimethylaminoethoxy)-α-phenyl-m-toluate was obtained from 2.04 g (8.42 mmol) of methyl α-hydroxy-α-phenyl-m-toluate in the same manner as in Production Example 1 (2) as a brown oily substance. Its spectroscopic data are as follows:
$^1$H-NMR (CDCl$_3$) δ (ppm) :2.27 (6H, s), 2.60 (2H, t, J=6.0 Hz), 3.56 (2H, t d, J=6.0 Hz, 2.7 Hz), 3.90 (3H, s), 5.41 (1H, s), 7.22~7.36 (5H, m), 7.38 (1H, t, J=7.8 Hz), 7.55 (1H, d, J=7.6 Hz), 7.91 (1H, d, J=7.6 Hz), 8.04 (1H, s)

(3) 0.36 g (1.20 mmol) of α-(2-Dimethylaminoethoxy)-α-phenyl-m-toluic acid shown below was obtained as a deliquescent pale brown amorphous substance from 0.48 g (1.53 mmol) of methyl α-(2-dimethylaminoethoxy)-α-phenyl-m-toluate in the same manner as in Production Example 2 (4).

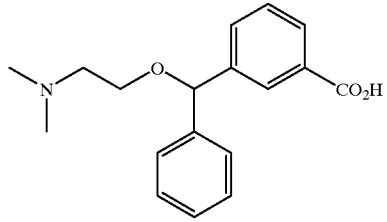

Its spectroscopic data are as follows:
$^1$H-NMR (CDCl$_3$) δ (ppm) : 2.61 (6H, s), 3.02 (2H, m), 3.71 (2H, m), 5.40 (1H, s), 7.16~7.36 (7H, m), 7.82 (1H, d, J=7.6 Hz), 8.07 (1H, s)

PRODUCTION EXAMPLE 4

α-(3-Dimethylaminopropoxy)-α-phenyl-p-toluic acid (1) 50 mg (0.153 mmol) of methyl α-(3-dimethylaminopropoxy)-α-phenyl-p-toluate was obtained as a pale brown oily substance from 2.42 g (10 mmol) of methyl a-hydroxy-a-phenyl-p-toluate and 2.43 g (20 mmol) of 3-dimethylaminopropyl chloride in the same manner as in Production Example 1 (2). Its spectroscopic data are as follows:
$^1$H-NMR (CDCl$_3$) δ (ppm) :1.83 (2H, m), 2.22 (6H, s) 2.40 (2H, t, J=7.4 Hz), 3.50 (2H, t, J=6.4 Hz), 3.89 (3H, s), 5.37 (1H, s), 7.22~7.34 (5H, m), 7.42 (2H, d, J=8.0 Hz), 7.98 (2H, d, J=8.4 Hz).

(2) 39 mg (0.124 mmol) of α-(3-Dimethylaminopropoxy)-α-phenyl-p-toluic acid shown below was obtained as white powder from 50 mg (0.153 mmol) of methyl α-(3-dimethylaminopropoxy)-α-phenyl-p-toluate in the same manner as in Production Example 2 (4). Its spectroscopic data are as follows:

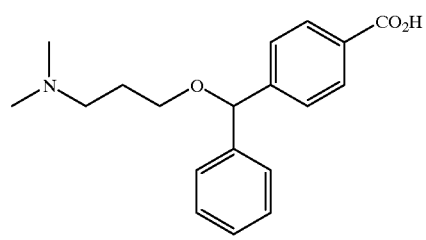

$^1$H-NMR (CDCl$_3$) δ (ppm) : 2.05 (2H, m), 2.64 (6H, s), 2.89 (1H, m), 3.04 (1H, m), 3.55 (2H, m), 5.37 (1H, s), 7.21~7.33 (5H, m), 7.35 (2H, d, J=8.0 Hz), 7.95 (2H, d, J=8.0 Hz).

PRODUCTION EXAMPLE 5

α-(2-Diethylaminoethoxy)-α-phenyl-p-toluic acid (1) 0.24 g (0.703 mmol) of methyl α-(2-diethylaminoethoxy)-α-phenyl-p-toluate was obtained as a pale brown oily substance from 3.17 g (13.08 mmol) of methyl α-hydroxy-α-phenyl-p-toluate and 2.66 g (19.61 mmol) of 2-diethylaminoethyl chloride in the same manner as in Production Example 1 (2). Its spectroscopic data are as follows:
$^1$H-NMR (CDCl$_3$) δ (ppm) : 1.01 (6H, t, J=7.2 Hz), 2.56 (4H, q, J=7.2 Hz), 2.76 (2H, t, J=6.4 Hz), 3.54 (2H, t, J=6.4 Hz), 3.89 (3H, s), 5.41 (1H, s), 7.22~7.34 (5H, m), 7.43 (2H, d, J=8.0 Hz), 7.98 (2H, d, J=8.8 Hz).

2) 0.20 g (0.611 mmol) of α-(2-Diethylaminoethoxy)-α-phenyl-p-toluic acid (shown below was obtained as a pale yellow amorphous ubstance from 0.24 g (0.703 mmol) of methyl α-diethylaminoethoxy)-α-phenyl-p-toluate in the same manner as in Production Example 2 (4).

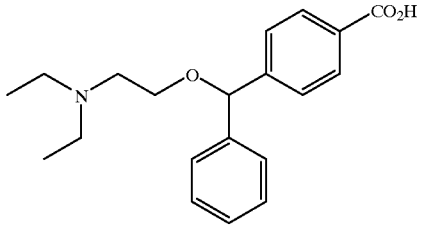

Its spectroscopic data are as follows:
¹H-NMR (CDCl₃) δ (ppm) 1.27 (6H, t, J=7.2 Hz), 3.14 (4H, q, J=7.2 Hz), 3.20 (2H, t, J=5.4 Hz), 3.68 (1H, m), 3.94 (1H, m), 5.39 (1H, s), 7.20~7.31 (5H, m), 7.32 (2H, d, J=8.0 Hz), 7.84 (2H, d, J=8.4 Hz).

PRODUCTION EXAMPLE 6

α-(2-Dimethylaminoethoxy)-p-toluic acid (1) 0.48 g (2.02 mmol) of methyl α-(2-dimethylaminoethoxy)-p-toluate was obtained as a yellow oily substance using 4.71 g (28.34 mmol) of methyl 4-hydroxymethylbenzoate as a raw material in the same manner as in Production Example 2 (2). Its spectroscopic data are as follows:
¹H-NMR (CDCl₃) δ (ppm) :2.27 (6H, s), 2.55 (2H, t, J=5.8 Hz), 3.57 (2H, t, J=5.8 Hz), 3.91 (3H, s), 4.59 (2H, s), 7.41 (2H, d, J=8.4 Hz), 8.01 (2H, d, J=8.4 Hz).

(2) 0.41 g (1.84 mmol) of α-(2-dimethylaminoethoxy)-p-toluic acid shown below was obtained as a pale yellow solid from 0.48 g (2.02 mmol) of methyl α-(2-dimethylaminoethoxy)-p-toluate in the same manner as in Production Example 2 (4).

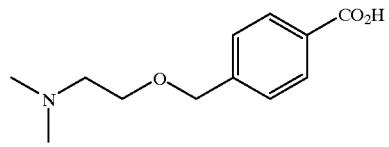

Its spectroscopic data are as follows:
¹H-NMR (CDCl₃) δ (ppm) : 2.64 (6H, s), 2.99 (2H, t, J=5.4 Hz), 3.73 (2H, t, J=5.2 Hz), 4.56 (2H, s), 7.29 (2H, d, J=8.0 Hz), 7.77 (2H, d, J=8.0 Hz).

PRODUCTION EXAMPLE 7

4-(2-Dimethylaminoethoxy)benzoic acid (1) 1.52 g (10 mmol) of methyl 4-hydroxybenzoate was dissolved in 40 ml of N,N-dimethylformamide and 2.16 g (15 mmol) of 2-dimethylaminoethyl chloride hydrochloride and 4.15 g (30 mmol) of potassium carbonate were further added. The mixture was heated at 80° C. and stirred overnight. After cooling, water was added to the reaction mixture, the obtained mixture was extracted twice with ethyl acetate, and the extract was washed with brine. The organic phase was dried (Na₂SO₄) and the solvent was distilled off. The resulting residue was purified by silica gel column chromatography (chloroform:methanol=70:1 to 15:1 (v/v)) to obtain 0.69 g (3.09 mmol) of methyl 4-(2-dimethylaminoethoxy)benzoate as a pale brown oily substance. Its spectroscopic data are as follows:

¹H-NMR (CDCl₃) δ (ppm) :2.34 (6H, s), 2.75 (2H, t, J=5.8 Hz), 3.88 (3H, s), 4.1 2 (2H, t, J=5.6 Hz), 6.93 (2H, d, J=9.2 Hz), 7.98 (2H, d, J=9.2 Hz)

(2) 0.69 g (3.09 mmol) of methyl 4-(2-dimethylaminoethoxy)benzoate was dissolved in 15 ml of methanol. 4.64 ml of a 1N sodium hydroxide aqueous solution was added thereto and the mixture was refluxed under heating for 3 hours. After cooling, 4.64 ml of 1N hydrochloric acid was added and the mixture was concentrated to dryness. A chloroform-methanol mixed solution (1:1 (v/v)) was added to the residue. The solution was stirred for a while and filtered with Celite. The solvent was distilled off under reduced pressure to obtain 0.65 g (3.09 mmol) of 4-(2-dimethylaminoethoxy)benzoic acid shown below as a pale yellow solid.

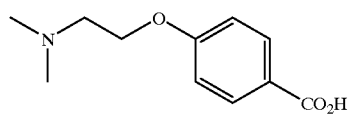

Its spectroscopic data are as follows:
¹H-NMR (DMSO-d₆) δ (ppm): 2.27 (6H, s), 2.71 (2H, t, J=5.6 Hz), 4.14 (2H, t, J=5.8 Hz), 7.01 (2H, d, J=8.8 Hz), 7.88 (2H, d, J=9.2 Hz)

PRODUCTION EXAMPLE 8

3-(2-Dimethylaminoethoxy)benzoic acid (1) 0.19 g (0.851 mmol) of methyl 3-(2-dimethylaminoethoxy) benzoate was obtained as a colorless oily substance using 1.52 g (10 mmol) of methyl 3-hydroxybenzoate as a starting material in the same manner as in Production Example 7 (1). Its spectroscopic data are as follows:

¹H-NMR (CDCl₃) δ (ppm): 2.34 (6H, s), 2.75 (2H, t, J=5.8 Hz), 3.91 (3H, s), 4.11 (2H, t, J=5.6 Hz), 7.13 (1H, dd, J=8.4 Hz, 2.8 Hz), 7.33 (1H, t, J=8.0 Hz), 7.58 (1H, d, J=2.4 Hz), 7.63 (1H, d, J=7.6 Hz).

(2) 0.18 g (0.851 mmol) of 3-(2-dimethylaminoethoxy) benzoic acid shown below was obtained as a deliquescent colorless amorphous substance from 0.19 g (0.851 mmol) of methyl 3-(2-dimethylaminoethoxy)benzoate in the same manner as in Production Example 7 (2).

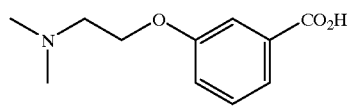

Its spectroscopic data are as follows:
¹H-NMR (CDCl₃+CD₃OD) δ (ppm) 2.75 (6H, s), 3.22 (2H, m), 4.34 (2H, t, J=4.8 Hz), 6.99 (1H, d, J=8.0 Hz), 7.30 (1H, t, J=7.8 Hz), 7.64 (1H, d, J=8.0 Hz), 7.68 (1H, s).

PRODUCTION EXAMPLE 9

3-[3-(2-dimethylaminoethoxy)phenyl]propionic acid (1) 20 ml of 10% hydrogen chloride-methanol was added to 1.64 g (10 mmol) of 3-hydroxycinnamic acid and the mixture was stirred at room temperature for one day. The reaction mixture was concentrated under reduced pressure. The residue was dissolved in ethyl acetate, washed twice with water and dried (MgSO₄). The solvent was distilled off. The residue was dissolved in 25 ml of methanol, 0.5 g of 10% palladium-carbon was added and the mixture was stirred overnight under hydrogen atmosphere. The reaction mixture was filtered and the filtrate was concentrated. The resulting residue was purified by silica gel column chromatography (chloroform:methanol=100:1 (v/v)) to obtain 1.75 g (9.71 mmol) of methyl 3-(3-hydroxyphenyl)propionate as a colorless oily substance. Its spectroscopic data are as follows:
$^1$H-NMR (CDCl$_3$) δ (ppm) : 2.62 (2H, t, J=7.8 Hz), 2.91 (2H, t, J=7.8 Hz), 3.68 (3H, s), 4.96 (1H, s), 6.68 (2H, m), 6.76 (1H, 3d, J=8.0 Hz), 7.15 (1H, t, J=8.2 Hz).

(2) 0.48 g (1.91 mmol) of methyl 3-[3-(2-dimethylaminoethoxy)phenyl]propionate was obtained as a pale brown oily substance from 1.75 g (9.71 mmol) of methyl 3-(3-hydroxyphenyl)proprionate in the same manner as in Production Example 7 (1). Its spectroscopic data are as follows:
$^1$H-NMR (CDCl$_3$) δ (ppm) : 2.33 (6H, s), 2.62 (2H, t, J=7.8 Hz), 2.72 (2H, t, J=5.6 Hz), 2.92 (2H, t, J=8.0 Hz), 3.67 (3H, s), 4.05 (2H, t, J=6.0 Hz), 6.74~6.80 (3H, m), 7.19 (1H, t, J=8.2 Hz).

(3) 0.45 g (1.90 mmol) of 3-[3-(2-dimethylaminoethoxy)phenyl]propionic acid shown below was obtained as a faint yellow oily substance from 0.48 g (1.91 mmol) of methyl 3-[3-2-dimethylaminoethoxy)phenyl]propionate in the same manner as in Production Example 7 (2).

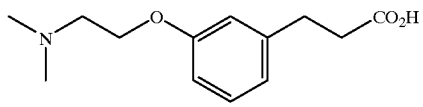

Its spectroscopic data are as follows:
$^1$H-NMR (CDCl$_3$) δ (ppm): 2.50 (6H, s), 2.59 (2H, t, J=8.2 Hz), 2.93 (2H, t, J=8.0 Hz), 2.96 (2H, t, J=5.2 Hz), 4.12 (2H, t, J=5.4 Hz), 6.67 (1H, d, J=8.2 Hz) 6.83 (1H, d, J=8.0 Hz), 6.84 (1H, s), 7.17 (1H, t, J=8.2 Hz).

PRODUCTION EXAMPLE 10
3-[4-(2-Dimethylaminoethoxy)-3-methoxphenyl]propionic acid (1) 20 ml of 10% hydrogen chloride-methanol was added to 1.94 g (10 mmol) of ferulic acid and the mixture was stirred at room temperature for one day. After the reaction mixture was concentrated under reduced pressure, the residue was dissolved in ethyl acetate, washed twice with water, and dried (MgSO$_4$). The solvent was distilled off. The resulting residue was dissolved in 25 ml of methanol. 0.5 g of 10% palladium-carbon was added thereto and the solution was stirred overnight under hydrogen atmosphere. The reaction mixture was filtered and the filtrate was concentrated. The residue was purified by silica gel column chromatography (n-hexane:ethyl acetate=3:1 (v/v)) to obtain 1.86 g (8.85 mmol) of methyl 3-(4-hydroxy-3-methoxyphenyl) propionate as a colorless oily substance. Its spectroscopic data are as follows:
$^1$H-NMR (CDCl$_3$) δ (ppm) : 2.60 (2H, t, J=7.6 Hz), 2.88 (2H, t, J=7.8 Hz), 3.67 (3H, s), 3.87 (3H, s), 5.48 (1H, s, 6.69 (1H, d, J=7.6 Hz), 6.70 (1H, s), 6.83 (1H, d, J=8.0 Hz).

(2) 0.44 g(1.56 mmol) of methyl 3-[4-(2-dimethylaminoethoxy)-3-methoxyphenyl]propionate was obtained as abrown oily substance from 1.86 g (8.85 mmol) of methyl 3-(4-hydroxy-3-methoxyphenyl)propionate in the same manner as in Production Example 7 (1). Its spectroscopic data are as follows:
$^1$H-NMR (CDCl$_3$) δ (ppm): 2.33 (6H, s), 2.61 (2H, t, J=7.8 Hz), 2.76 (2H, t, J=6.2 Hz), 2.89 (2H, t, J=7.6 Hz), 3.67 (3H, s), 3.84 (3H, s), 4.08 (2H, t, J=6.2 Hz), 6.71 (1H, d, J=7.6 Hz), 6.72 (1H, s), 6.81 (1H, d, J=8.0 Hz).

(3) 0.42 g (1.56 mmol) of 3-[4-(2-Dimethylaminoethoxy)-3-methoxyphenyl]propionic acid shown below was obtained as a reddish brown solid from 0.44 g (1.56 mmol) of methyl 3-[4-(2-dimethylaminoethoxy)-3-methoxyphenyl]propionate in the same manner as in Production Example 7 (2).

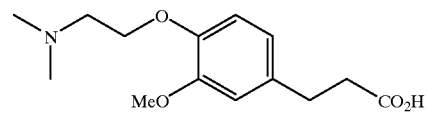

Its spectroscopic data are as follows:
$^1$H-NMR (CDCl$_3$) δ (ppm) : 2.54 (6H, s), 2.57 (2H, t, J 7.0 Hz), 2.89 (2H, t, J=6.8 Hz), 3.05 (2H, t, J=5.4 Hz), 3.79 (3H, s), 4.08 (2H, t, J=5.4 Hz),6.68 (1H, d, J=8.8 Hz), 6.76 (1H, s), 6.77 (1H, d, J=6.4 Hz).

PRODUCTION EXAMPLE 11
6-(2-Dimethylaminoethoxy)-2-naphthoic acid (1) 15 ml of 10% hydrogen chloride-methanol was added to 1.0 g (5.31 mmol) of 6-hydroxy-2-naphthoic acid and the mixture was stirred at room temperature for one day. After the reaction mixture was concentrated under reduced pressure, the residue was dissolved in ethyl acetate, washed twice with water, and dried (MgSO$_4$). The solvent was distilled off to obtain 1.07 g (5.29 mmol) of methyl 6-hydroxy-2-naphthoate as a pale yellowish brown powder. Its spectroscopic data are as follows:
$^1$H-NMR (CDCl$_3$) δ (ppm) : 3.97 (3H, s), 5.40 (1H, s) 7.14~7.19 (2H, m), 7.70 (1H, d, J=8.8 Hz), 7.86 (1H, d, J=8.4 Hz), 8.01 (1H, d, J=8.4 Hz), 8.53 (1H, s).

(2) 0.41 g (1.50 mmol) of methyl 6-(2-dimethylaminoethoxy)-2-naphthoate (was obtained as a pale brown solid from 1.07 g (5.29 mmol) of methyl 6-hydroxy-2-naphthoate in the same manner as in Production Example 7 (1). Its spectroscopic data are as follows:
$^1$H - NMR (CDCl$_3$) δ (ppm) : 2.37 (6H, s), 2.81 (2H, t,J=5.6 Hz), 3.96 (3H, s), 4.21 (2H, t, J=5.6 Hz), 7.16 (1H, d, J=2.4 Hz), 7.23 (1H, d d, J=9.0 Hz, 2.6 Hz), 7.74 (1H, d, J=8.4 Hz), 7.83 (1H, d, J=8.8 Hz), 8.02 (1H, dd, J=8.6 Hz, 1.8 Hz), 8.52 (1H, s).

(3) 0.38 g (1.47 mmol) of 6-(2-Dimethylaminoethoxy)-2-naphthoic acid shown below was obtained as a pale yellow crystalline powder from 0.41 g (1.50 mmol) of methyl 6-(2-dimethylaminoethoxy)-2-naphthoate in the same manner as in Production Example 7 (2).

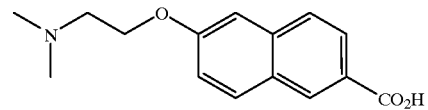

Its spectroscopic data are as follows:
$^1$H-NMR (DMSO-d$_6$) δ (ppm) : 2.33 (6H, s), 2.82 (2H, t, J=5.8 Hz), 4.25 (2H, t, J=5.6 Hz), 7.24(1H, dd, J=9.2 Hz, 2.4 Hz), 7.42 (1H, d, J=2.4 Hz), 7.86 (1H, d, J=8.8 Hz), 7.93 (1H, dd, J=8.6 Hz, 1.8 Hz), 8.00 (1H, d, J=9.2 Hz), 8.51 (1H, s).

PRODUCTION EXAMPLE 12
4-[4-(2-dimethylaminoethox)phenyl]benzoic acid (1) 15 ml of 10% hydrogen chloride-methanol was added to 1.07 g (5.0 mmol) of 4-(4-hydroxyphenyl)benzoic acid and the mixture was refluxed under heating for 5 hours. After the reaction mixture was concentrated under reduced pressure, water was added thereto and the solution was extracted twice with a chloroform-methanol mixed solution (10:1 (v/v)). The extract was washed with a sodium hydrogencarbonate aqueous solution and dried ($MgSO_4$). The solvent was distilled off to obtain 0.97 g (4.25 mmol) of methyl 4-(4-hydroxyphenyl)benzoate as a faint yellow powder. Its spectroscopic data are as follows:

$^1$H-NMR ($CDCl_3$) δ (ppm) :3.93 (3H, s), 4.93 (1H, s), 6.93 (2H, dd, J=6.6 Hz, 2.2 Hz), 7.52 (2H, dd, J=6.6 Hz, 2.2 Hz), 7.61 (2H, dd, J=6.8 Hz, 2.0 Hz), 8.07 (2H, d d, J=6.8 Hz, 2.0 Hz).

(2) 0.69 g (2.30 mmol) of methyl 4-[4-(2-dimethylaminoethoxy)phenyl]benzoate was obtained as a faint yellow solid from 0.97 g (4.25 mmol) of methyl 4-(4-hydroxyphenyl)benzoate in the same manner as in Production Example 7 (1). Its spectroscopic data are as follows:

$^1$H - NMR ($CDCl_3$) δ (ppm) : 2.36 (6H, s), 2.76 (2H, t, J=5.8 Hz), 3.93 (3H, s), 4.12 (2H, t, J=5.8 Hz), 7.01 (2H, d d, J=8.8 Hz), 7.56 (2H, d, J=8.8 Hz), 7.62 (2H, d, J=8.8 Hz), 8.07 (2H, d, J=8.8 Hz).

(3) 0.68 g (2.27 mmol) of methyl 4-[4-(2-dimethylaminoethoxy)phenyl]benzoate was dissolved in 18 ml of methanol-methylene chloride (5:1 (v/v)). 3.4 ml of a 1N sodium hydroxide aqueous solution was added thereto and the mixture was refluxed under heating for 5 hours. After cooling to room temperature, 3.4 ml of 1N hydrochloric acid was added and stirred. The precipitate thus formed was collected by filtration, washed, and dried to obtain 0.54 g (1.89 mmol) of 4-[4-(2-dimethylaminoethoxy)phenyl]benzoic acid as faint yellowish white powder.

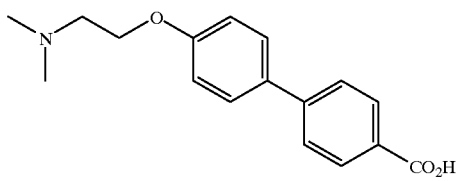

Its spectroscopic data are as follows:

$^1$H-NMR (DMSO-$d_6$) δ (ppm) : 2.24 (6H, s) 2.66 (2H, t, J=5.8 Hz), 4.11(2H, t, J=5.8 Hz), 7.05 (2H, d, J=8.8 Hz), 7.67 (2H, d, J=8.4 Hz), 7.73 (2H, d, J=8.4 Hz), 7.98 (2H, d, J=8.4 Hz).

PRODUCTION EXAMPLE 13

3-(4-dimethylaminophenyl)propionic acid (1) 0.37 g (1.79 mmol) of methyl 3-(4-dimethylaminophenyl)propionate was obtained as a colorless oily substance using 0.57 g (3.0 mmol) of p-dimethylaminocinnamic acid as a starting material the same manner as in Production Example 10 (1). Its spectroscopic data are as follows:

$^1$H-NMR ($CDCl_3$) δ (ppm) 2.58 (2H, t, J=7.8 Hz), 2.86 (2H, t, J=7.8 Hz), 2.91 (6H, s), 3.67 (3H, s), 6.69 (2H, d, J=8.8 Hz), 7.07 (2H, d, J=8.8 Hz).

(2) 0.13 g (0.673 mmol) of 3-(4-dimethylaminophenyl) propionic acid shown below was obtained as a pale orange solid from 0.37 g (1.79 mmol) of methyl 3-(4-dimethylaminophenyl)propionate in the same manner as in Production Example 2 (4).

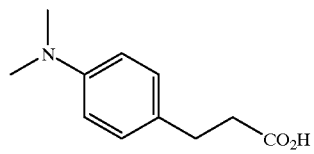

Its spectroscopic data are as follows:

$^1$-NMR ($CDCl_3$) δ (ppm) : 2.63 (2H, t, J=8.0 Hz), 2.87 (2H, t, J=7.8 Hz), 2.91 (6H, s), 6.70 (2H, d, J=8.8 Hz), 7.09 (2H, d, J=8.8 Hz)

PRODUCTION EXAMPLE 14

O-(2-dimethylaminoethyl)benzilic acid (1) 5.42 g (17.29 mmol) of methyl o-(2-dimethylaminoethyl)benzilate was obtained as a pale yellowish brown oily substance using 4.85 g (20 mmol) of methyl benzilate acid as a starting material in the same manner as in Production Example 1 (2). Its spectroscopic data are as follows:

$^1$H-NMR ($CDCl_3$) δ (ppm) 2.23 (6H, s), 2.55 (2H, t, J=6.0 Hz), 3.36 (2H, t, J=6.0 Hz), 3.76 (3H, s), 7.28~7.34 (6H, m), 7.40~7.45 (4H, m).

(2) 0.24 g (0.802 mmol) of o-(2-dimethylaminoethyl) benzilic acid shown below was obtained as a faint yellow solid from 0.31 g (1.0 mmol) of methyl o-(2-dimethylaminoethyl)benzilate in the same manner as in Production Example 2 (4).

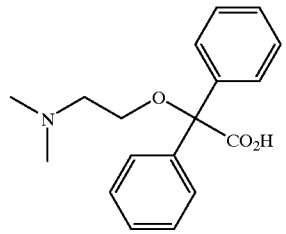

Its spectroscopic data are as follows: $^1$H-NMR ($CDCl_3$) δ (ppm) : 2.87 (6H, s), 3.09 (2H, t, J=4.8 Hz), 3.51 (2H, t, J=4.8 Hz), 7.21~7.30 (6H, m), 7.50~7.54 (4H, m).

PRODUCTION EXAMPLE 15

4-(4-dimethylamino-1-phenyl-1-butenyl)benzoic acid (1) 2.97 g (6.93 mmol) of (3-dimethylaminopropyl) triphenylphophonium bromide was dissolved in 25 ml of tetrahydrofuran and 4.77 ml (7.63 mmol) of 1.6 M n-butyl lithium was added dropwise thereto under cooling in a dry ice-acetone bath. The mixture was stirred for 30 minutes under ice-cooling. A solution of 1.67 g (6.93 mmol) of methyl p-benzoylbenzoate in 15 ml of tetrahydrofuran was added thereto and the mixture was stirred for 30 minutes. Returning to room temperature, it was stirred for one hour. After brine was added, the reaction mixture was extracted twice with ethyl acetate, the extract was washed with brine, and dried ($Na_2SO_4$). The solvent was distilled off and the residue was purified by silica gel column chromatography (chloroform:methanol=100:1 to 15:1 (v/v)) to obtain 1.59 g (5.14 mmol) of methyl 4-(4-dimethylamino-1-phenyl-1-butenyl)benzoate as a pale brown oily substance. Its spectroscopic data are as follows:

$^1$H - NMR ($CDCl_3$) δ (ppm) :2.18, 2.19 (6H, s×2), 2.29 (2H, m), 2.39 (2H, m), 3.89, 3.93 (3H, s×2), 6.14, 6.22 (1H, t×2, J=7.2 Hz, 7.2 Hz,), 7.14~7.41 (7H, m), 7.91, 8.04 (2H, d×2, J=8.4 Hz, 8.4 Hz).

(2) 0.59 g (2.0 mmol) of 4-(4-dimethylamino-1-phenyl-1-butenyl)benzoic acid (shown below was obtained as a pale brown amorphous substance from 0.62 g (2.0 mmol) of methyl 4-(4-dimethylamino-1-phenyl-1-butenyl)benzoate in the same manner as in Production Example 1 (3).

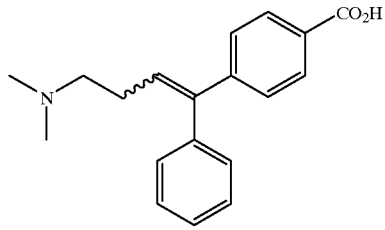

Its spectroscopic data are as follows:
$^1$H-NMR (CDCl$_3$) δ (ppm) : 2.40, 2.64 (2H, m×2), 2.88 (2H, m), 5.90, 6.39 (1H, t×2, J=7.4 Hz, 7.4 Hz),7.12~7.28 (5H, m), 7.32, 7.39 (2H, t×2, J=7.2 Hz, 7.2 Hz,), 7.57, 7.94 (2H, d×2, J=8.6 Hz, 8.6 Hz).

PRODUCTION EXAMPLE 16

4-(4-dimethylamino-1-phenylbutyl)benzoic acid 0.41 g (1.39 mmol) of 4-(4-Dimethylamino-1-phenyl-1-butenyl)benzoic acid obtained in the method of Production Example 15 was dissolved in 12 ml of a mixed solution of methanol-methylene chloride (5:1 (v/v)). 0.2 g of 10% palladium-carbon was added thereto and the mixture was stirred overnight under hydrogen atmosphere. The reaction mixture was filtered with Celite and the filtrate was concentrated under reduced pressure. The residue was triturated with diethyl ether and the precipitate was collected by filtration to obtain 0.40 g (1.34 mmol) of 4-(4-dimethylamino-1-phenylbutyl)benzoic acid shown below as a faint yellowish while powder.

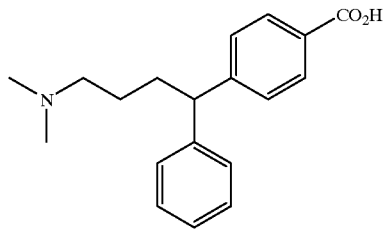

Its spectroscopic data are as follows:
$^1$H-NMR (CDCl$_3$) δ (ppm) : 1.64 (1H, m), 1.73 (1H, m), 2.27 (1H, m), 2.58 (6H, s), 2.84 (2H, m), 3.95 (1H, m), 7.13~7.28 (7H, m), 7.80 (2H, d, J=8.0 Hz).

PRODUCTION EXAMPLE 17

4-[N-(2-dimthylaminoethyl)phenylamino]benzoic acid (1) 30 ml of 10% hydrogen chloride-methanol was added to 1.59 g (7.46 mmol) of 4-(phenylamino)benzoic acid and the mixture was refluxed overnight under heating. After the reaction mixture was concentrated under reduced pressure, the residue was dissolved in ethyl acetate, washed with a sodium hydrogencarbonate aqueous solution and brine, and dried (MgSO$_4$). The solvent was distilled off and the residue was purified by silica gel column chromatography (n-hexane:ethyl acetate=5:1 (v/v)) to obtain 1.66 g (7.30 mmol) of methyl 4-(phenylamino)benzoate as a pale yellow solid. Its spectroscopic data are as follows:
$^1$H-NMR (CDCl$_3$) δ (ppm) : 3.87 (3H, s), 6.01 (1H, br), 6.98 (2H, d, J=9.2 Hz), 7.07 (1H, t, J=7.2 Hz), 7.17 (2H, d, J=7.6 Hz), 7.34 (2H, t, J=8.0 Hz), 7.91 (2H, d, J=8.8 Hz).

(2) 0.68 g (2.28 mmol) of methyl 4-[N-(2-dimethylaminoethyl)phenylamino]benzoate was obtained as a brown oily substance from 0.77 g (3.39 mmol) of methyl 4-(phenylamino)benzoate in the same manner as in Production Example 1 (2). Its spectroscopic data are as follows:
$^1$H-NMR (CDCl$_3$) δ (ppm) 2.27 (6H, s), 2.58 (2H, t, J=7.8 Hz), 3.85 (3H, s), 3.86 (2H, t, J=7.8 Hz), 6.72 (2H, d, J=9.2 Hz), 7.19~7.25 (3H, m), 7.40 (2H, t, J=7.8 Hz), 7.83 (2H, d, J=9.2 Hz).

(3) 0.57 g (2.0 mmol) of 4-[N-(2-dimethylaminoethyl)phenylamino]benzoic (shown below) was obtained as a faint yellowish brown powder from 0.60 g (2.01 mmol) of methyl 4-[N-(2-dimethylaminoethyl) phenylamino]benzoate in the same manner as in Production Example 1 (3).

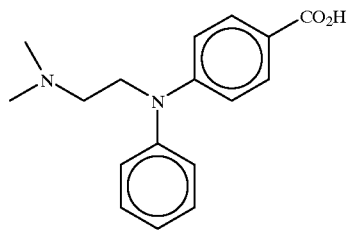

Its spectroscopic data are as follows:
$^1$H-NMR (CDCl$_3$) δ (ppm) : 2.39 (6H, s), 2.75 (2H, t, J=8.0 Hz), 3.98 (2H, t, J=7.8 Hz), 6.81 (2H, d, J=8.8 Hz), 7.17~7.23 (3H, m), 7.39 (2H, t, J=8.0 Hz), 7.89 (2H, d, J=8.8 Hz).

PRODUCTION EXAMPLE 18

4-[N-(3-dimethylaminopropyl)phenylamino]benzoic acid (1) 0.90 g (2.88 mmol) of methyl 4-[N-(3-dimethylaminopropyl)phenylamino]benzoate was obtained as a pale brown oily substance from 0.84 g (3.70 mmol) of methyl 4-(phenylamino)benzoate obtained by the method of Production Example 17 (1) and 0.67 g (5.54 mmol) of 3-dimethylaminopropyl chloride in the same manner as in Production Example 1 (2). Its spectroscopic data are as follows:
$^1$H - NMR (CDC$_3$) δ (ppm) 1.82 (2H, m), 2.20 (6H, s), 2.30 (2H, t, J=7.0 Hz), 3.79 (2H, t, J=7.6 Hz), 3.85 (3H, s), 6.73 (2H, d, J=9.2 Hz), 7.18~7.24 (3H, m), 7.39 (2H, t, J=7.8 Hz), 7.82 (2H, d, J=8.8 Hz).

(2) 0.78 g (2.61 mmol) of 4-[N-(3-dimethylaminopropyl) phenylamino]benzoic acid shown below was obtained as a faint brown powder from 0.88 g (2.82 mmol) of methyl 4-[N-(3-dimethylaminopropyl)phenyl-amino]benzoate in the same manner as in Production Example 1 (3).

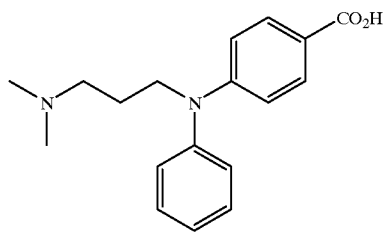

Its spectroscopic data are as follows:
$^1$H-NMR (CDCl$_3$) δ (ppm) :2.0 9 (2H, m), 2.71 (2H, t, J=8.2 Hz), 3.79 (2H, t, J=7.8 Hz), 6.81 (2H, d, J=8.8 Hz), 7.13~7.19 (3H, m), 7.36 (2H, t, J=8.0 Hz), 7.82 (2H, d, J=9.2 Hz) 8.51 (1H, s).

EXAMPLE 1

4-[3-(Benzyloxycarbonylamino)propylamino]-2-chloro-3-nitroquinoline 0.19 g (0.768 mmol) of 2,4-dichloro-3-nitroquinoline and 0.16 g (0.768 mmol) of N-(benzyloxycarbonyl)-1,3-propanediamine was heated at 70° C. in 5 ml of triethylamine for one hour with stirring. After triethylamine was distilled off under reduced pressure, the residue was dissolved in methylene chloride, washed with water, and dried ($MgSO_4$). The solvent was distilled off under reduced pressure and the residue was purified by silica gel column chromatography (n-hexane:ethyl acetate=2:1 (v/v)) to obtain 0.27 g (0.651 mmol) of 4-[3-(benzyloxycarbonylamino)propylamino]-2-chloro-3-nitroquinoline shown below as yellow powder.

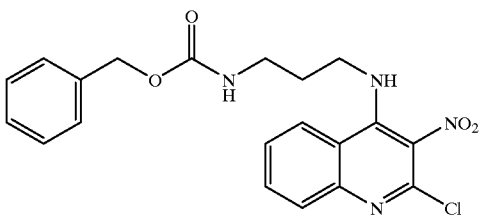

Its spectroscopic data are as follows:
$^1$H-NMR ($CDCl_3$) δ (ppm) :1.79 (2H, m), 3.35 (4H, m), 5.02 (1H, br), 5.18 (2H, s), 7.15 (1H, br), 7.37 (5H, m), 7.57 (1H, t, J=8.0 Hz), 7.73 (1H, t, J=7.8 Hz), 7.90 ($^1$H, d, J=8.4 Hz), 8.21 (1H, d, J=8.0 Hz).

EXAMPLE 2

3-Amino-4-[3-benzyloxycarbonylamino)propylamino]-2-chloroquinoline 0.27 g (0.651 mmol) of 4-[3-(benzyloxycarbonylamino)propylamino]-2-chloro-3-nitroquinoline was dissolved in 10 ml of methanol. One ml of concentrated hydrochloric acid and 0.22 g (0.390 mmol) of iron powder were added thereto and the mixture was stirred at room temperature for 2 hours. The reaction mixture was poured into a saturated sodium hydrogencarbonate aqueous solution. After the resulting mixed solution was extracted with ethyl acetate, the extract was washed with brine and dried ($Na_2SO_4$). The solvent was distilled off under reduced pressure and the residue was purified by silica gel column chromatography (chloroform:methanol=300:1 (v/v)) to obtain 0.12 g (0.312 mmol) of 3-amino-4-[3-(benzyloxycarbonylamino)propylamino]-2-chloroquinoline shown below as faint yellow powder.

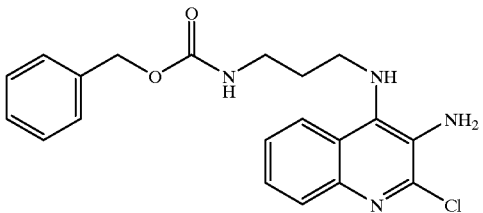

Its spectroscopic data are as follows:
$^1$H-NMR ($CDCl_3$) δ (ppm) :1.76 (2H, m), 3.30 (2H, m), 3.42 (2H, q, J=6.3 Hz), 4.21 (2H, b r), 4.44 (1H, br), 4.92 (1H, br), 5.16 (2H, s), 7.30~7.39 (5H, m), 7.46 (2H, m), 7.89 (2H, m).

EXAMPLE 3

1-[3-(benzyloxycarbonylamino)propyl]-4-chloro-1H-imidazo[4,5-c]-quinoline 0.52 ml (3.12 mmol) of triethyl ortho-formate was added to 0.12 g (0.312 mmol) of of 3-amino-4-[3-(benzyloxycarbonylamino)propylamino]-2-chloroquinoline. The mixture was heated at 100° C. and stirred for 3.5 hours. The reaction mixture was concentrated under reduced pressure to obtain 0.12 g (0.304 mmol) of 1-[3-(benzyloxycarbonylamino)propyl]-4-chloro-1H-imidazo[4,5-c]-quinoline (shown below) as a pale yellow solid.

Its spectroscopic data are as follows:

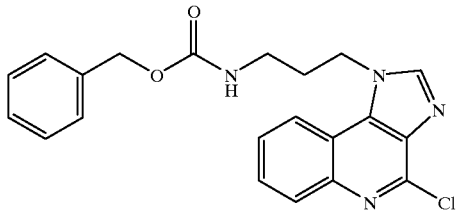

$^1$H-NMR ($CDCl_3$) δ (ppm) 2.24 (2H, m), 3.36 (2H, q, J=6.4 Hz), 4.67 (2H, t, J=7.0 Hz), 4.95 ($^1$H, b r), 5.14 (2H, s), 7.31~7.39 (5H, m), 7.62 (1H, t, J=7.8 Hz), 7.71 (1H, t, J=7.8 Hz), 8.09 (1H, s), 8.13 (1H, d, J=8.4 Hz), 8.21 (1H, d, J=8.4 Hz).

EXAMPLE 4

1-(3-Aminopropyl)-4-chloro-1H-imidazo[4,5-c]-quinoline accetate 3 ml of 33% hydrogen bromide-acetic acid was added to 0.12 g (0.304 mmol) of 1-[3-(benzyloxycarbonylamino)propyl]-4-chloro-1H-imidazo[4,5-c]quinoline and the mixture was stirred at room tempterature for 1.5 hours. After the reaction mixture was concentrated under reduced pressure, a 1N sodium hydroxide aqueous solution and brine were added to the residue and the solution was extracted five times with chloroform. The organic phase was dried ($Na_2SO_4$), the solvent was distilled off under reduced pressure, and the residue was purified by silica gel column chromatography (chloroform:methanol:32% acetic acid= 12:6:1 (v/v)) to obtain 60 mg (0.187 mmol) of 1-(3-aminopropyl)-4-chloro-1H-imidazo[4,5-c]quinoline·acetate shown below as a pale yellow solid.

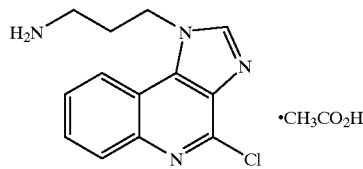

Its spectroscopic data are as follows:
$^1$H-NMR ($CD_3OD$) δ (ppm): 1.94 (3H, s), 2.39 (2H, m), 3.12 (2H, t, J=7.8 Hz), 4.82 (2H, t, J=7.2 Hz), 7.70 (2H, m), 7.97 (1H, d, J=8.0 Hz), 8.27 (1H, d, J=8.0 Hz), 8.41 (1H, s).

EXAMPLE 5

1-(3-Aminopropyl)-1H-imidazo[4,5-c]quinoline-4-amine 60 mg (0.187 mmol) of 1-(3-aminopropyl)-1H-imidazo[4,5-c]quinoline·acetate, 10 ml of methanol and 5 ml of liquid ammoniun were stirred in an autoclave overnight at 150° C. under heating. The reaction mixture was concentrated under reduced pressure. The resulting residue was dissolved in a small amount of water and 0.5 ml of a 1N sodium hydroxide aqueous solution was added thereto. The precipitate was collected by filtration and recrystallized from ethanol to obtain 11 mg (0.0455 mmol) of 1-(3-aminopropyl)-1H-imidazo[4,5-c]quinoline-4-amine shown below as pale yellow cotton-like crystals (mp: 243–245° C. (decomposition)).

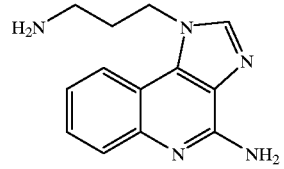

Its spectroscopic data are as follows:
IR (KBr) cm$^{-1}$ : 33 20, 3170, 1650. $^1$H-NMR (DMSO-d$_6$) δ (ppm) :1.93 (2H, m), 2.57 (2H, t, J=6.6 Hz), 4.64 (2H, t, J=7.0 Hz), 6.55 (2H, s), 7.26 (1H, t, J=7.2 Hz), 7.44 (1H, t, J=7.4 Hz), 7.62 (1H, d, J=8.0 Hz), 8.12 (1H, d, J=8.0 Hz), 8.19 (1H, s).

EXAMPLE 6

4- [3-(tert-Butoxycarbonylamino)propylamino]-2-chloro-3-nitroquinoline 0.59 g (2.41 mmol) of 2,4-Dichloro-3-nitroquinoline and 0.42 g (2.41 mmol) of N-(tert-butoxycarbonyl)-1,3-propanediamine were heated at 70° C. in 10 ml of triethylamine and stirred for 1.5 hours. Triethylamine was distilled off under reduced pressure. The resulting residue was dissolved in methylene chloride, washed with water, and dried (Na$_2$SO$_4$). After the solvent was distilled off under reduced pressure, the residue was triturated with methanol and filtered to obtain 0.61 g (1.60 mmol) of 4-[3-(tert-butoxycarbonylamino)propylamino]-2-chloro-3-nitroquinoline shown below as yellow crystals (mp: 159–161° C.).

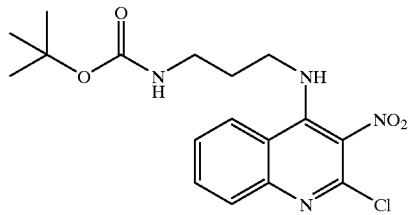

Its spectroscopic data are as follows:
IR (KBr) cm$^{-1}$ : 3310, 1680, 1580. $^1$H-NMR (CDCl$_3$) δ (ppm) : 1.50 (9H, s), 1.77 (2H, m), 3.27 (2H, q, J=6.1 Hz), 3.36 (2H, q, J=6.0 Hz), 4.82 (1 H, br), 7.37 (1H, br), 7.55 (1H, t, J=7.8 Hz), 7.72 (1H, t, J=7.7 Hz), 7.89 (1H, d, J=8.2 Hz), 8.27 (1H, d, J=8.4 Hz).

EXAMPLE 7

3-Amino-4-[3- (tert-butoxycarbonylamino)propylamino]-2-chloroquinoline 0.27 g (0.70 mmol) of 4-[3-(tert-Butoxycarbonylamino)propylamino]-2-chloro-3-nitroquinoline was dissolved in 7 ml of ethanol. Tin chloride [II] dihydrate (0.55 g, 2.45 mmol) was added thereto and the mixture was refluxed under heating for 1 hour. After cooling, the reaction mixture was poured into 2N aqueous ammonia. The resulting solution was extracted twice with chloroform, thereafter the extract was washed (brine), and dried (Na$_2$SO$_4$). The solvent was distilled off under reduced pressure and the residue was purified by silica gel column chromatography (n-hexane:ethyl acetate=1:1 (v/v)) to obtain 0.15 g (0.428 mmol) of 3-amino-4-[3-(tert-butoxycarbonylamino) propylamino]-2-chloro-quinoline shown below as pale yellow crystals.

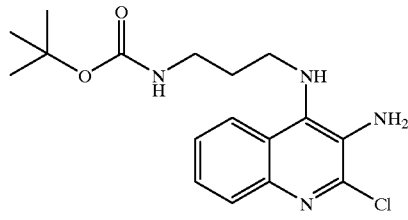

Its spectroscopic data are as follows:
$^1$H-NMR (CDCl$_3$) δ (ppm) : 1.49 (9H, s), 1.73 (2H, m), 3.29 (2H, t, J=6.2 Hz), 3.35 (2H, q, J=6.0 Hz), 4.28 (2H, br), 4.60 (1H, br), 4.75 (1H, br), 7.44 (2H, m), 7.87 (1H, d, J=7.6 Hz), 7.94 (1H, d, J=7.6 Hz).

EXAMPLE 8

1-[3-(tert-butoxycarbonylamino)propyl]-4-chloro-1H-imidazo[4,5-c]quinoline 0.36 ml (2.14 mmol) of triethyl ortho-formate was added to 0.15 g (0.428 mmol) of 3-amino-4-[3-(tert-butoxycarbonylamino)-propylamino]-2-chloro-quinoline. The mixture was stirred at 100° C. for 2 hours and then at 80° C. for overnight. The reaction mixture was concentrated under reduced pressure and the residue was purified by silica gel column chromatography (chloroform:methanol 150:1 to 100:1 (v/v)) to obtain 0.14 g (0.388 mmol) of 1-[3-(tert-butoxycarbonylamino)propyl]-4-chloro-1H-imidazo[4,5-c] quinoline shown below as white powder (mp: 155–156° C.).

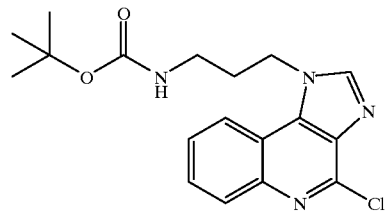

Its spectroscopic data are as follows:
IR (KBr) cm$^{-1}$ : 3380, 1680, 1520.
$^1$H-NMR (CDCl$_3$) δ (ppm) : 1.47 (9H, s), 2.22 (2H, m), 3.30 (2H, q, J=6.4 Hz), 4.68 (2H, t, J=7.2 Hz), 4.7 (1H, H, br), 7.66 (1H, t, J=7.6 Hz), 7.72 (1H, t, J=7.6 Hz), 8.09 (1H, s), 8.16 (1H, d, J=8.4 Hz), 8.21 (1H, d, J=8.4 Hz).

EXAMPLE 9

1-(3-Aminopropyl)-4-chloro-1H-imidazo[4,5-c]quinoline 50 mg (0.139 mg) of 1-[3-(tert-butoxycarbonylamino)-propyl]-4-chloro-1H-imidazo[4,5-c]quinoline was dissolved in 3 ml of methylene chloride. 0.11 ml (1.39 mmol) of trifluoroacetic acid was added thereto and the mixture was stirred at room temperature for one day. The reaction mixture was concentrated under reduced pressure and 1 ml of a 1N sodium hydroxide aqueous solution and brine were added to the residue. The resulting solution was extracted with chloroform five times, thereafter the extract was dried (Na$_2$SO$_4$), and concentrated under reduced pressure. The residue was triturated with diethyl ether (containing a small amount of methylene chloride) and the precipitate thus formed was collected by filtration to obtain 14 mg (0.0536 mmol) of 1-(3-aminopropyl)-4-chloro-1H-imidazo[4,5-c]quinoline shown below as white powder.

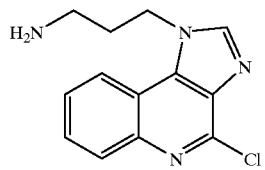

Its spectroscopic data are as follows:

IR (KBr) cm$^{-1}$ : 340, 1590, 1510. $^1$H-NMR (CDCl$_3$+ CD$_3$OD) δ (ppm) : 2.06 (2H, m), 2.72 (2H, t, J=6.8 Hz), 2.98 (2H, b r), 4.64 (2H, t, J=7.0 Hz), 7.57 (1H, t, J=7.6 Hz), 7.61 (1H, t, J=7.6 Hz), 8.03 (1H, s), 8.05 (1H, d, J=8.0 Hz), 8.11 (1H, d, J=8.0 Hz).

EXAMPLE 10

1-(3-Aminopropyl)-1H-imidazo[4,5-c]quinoline-4-amine 14 mg (0.0536 mmol) of 1-(3-aminopropyl)-4-chloro-1H-imidazo[4,5-c]quinoline, 5 ml of methanol and 3 ml of liquid ammonia were stirred in an autoclave overnight at 150° C. under heating. The reaction mixture was concentrated under reduced pressure and 0.3 ml of a 1N sodium hydroxide solution was added to the residue. The precipitate thus formed was collected by filtration to obtain 8 mg (0.0331 ml) of 1-(3-aminopropyl)-1H-imidazo[4,5-c]quinoline-4-amine shown below.

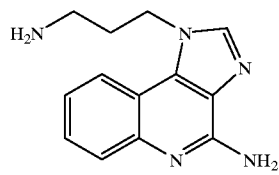

The physicochemical data of this compound was in agreement with the compound of Example 5.

EXAMPLE 11

4-Benzylamino-1-[3-(tert-butoxycarbonylamino)propyl]-1H-imidazo[4,5-c]quinoline

One ml of benzylamine was added to 30 mg (0.0831 mmol) of 1-[3-(tert-butoxycarbonylamino)propyl]-4-chloro-1H-imidazo[4,5-c]quinoline and the mixture was stirred at 150° C. for 3 hours. Excess benzylamine was distilled off under reduced pressure and 1N hydrochloric acid and brine were added thereto. The mixture was extracted twice with methylene chloride. The organic phase was washed with a saturated sodium hydrogencarbonate aqueous solution and dried (Na$_2$SO$_4$). The solvent was distilled off under reduced pressure and the residue was purified by silica gel column chromatography (chloroform:methanol=150:1 (v/v)) to obtain 35 mg (0.0811 mmol) of 4-benzylamino-1-[3-(tert-butoxycarbonylamino)propyl]-1H-imidazo[4,5-c]quinoline shown below as white powder (mp: 171–172.5° C.).

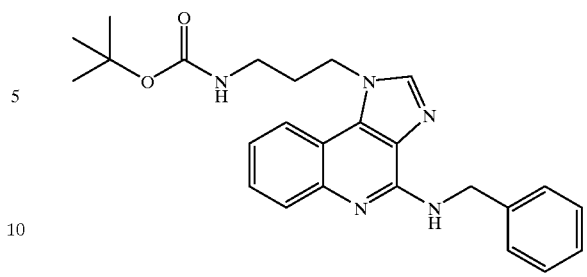

Its spectroscopic data are as follows:

IR (KBr) cm$^{-1}$ : 3330, 1700, 1590, 1540. $^1$H-NMR (CDCl$_3$) δ (ppm) :1.46 (9H, s), 2.18 (2H, m), 3.25 (2H, m), 4.57 (2H, t, J=7.0 Hz), 4.64 (1H, br), 4.95 (2H, d, J=5.2 Hz), 6.05 (1H, br), 7.26~7.36 (4H, m), 7.47 (2H, d, J=7.6 Hz), 7.51 (1H, t, J=7.6 Hz), 7.82 (1H, s), 7.92 (2H, t, J=8.0 Hz).

EXAMPLE 12

1-(3-Aminopropyl)-1H-imidazo[4,5-c]quinoline-4-amine 30 mg (0.0695 mmol) of 4-benzylamino-1-[3-(tert-butoxycarbonylamino)propyl]-1H-imidazo[4,5-c]quinoline was dissolved in 3 ml of formic acid. 0.1 g of 20% palladium hydroxide-carbon was added thereto and the mixture was refluxed under heating for one day. The reaction mixture was filtered and the filtrate was evaporated to distill off the solvent under reduced pressure. The resulting residue was purified by silica gel column chromatography (chloroform:methanol:32% acetic acid=6:3:1 (v/v)) to obtain the acetic acid salt of the object. The thus obtained product was subjected to treatment with alkali to obtain the free base. The precipitate thus formed was collected by filtration to obtain 7 mg (0.0290 mmol) of 1-(3-aminopropyl)-1H-imidazo[4,5-c]quinoline-4-amine shown below as faint brown powder.

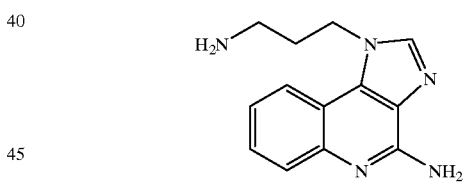

The physicochemical data of this compound was in agreement with compound of Example 5.

EXAMPLE 13

4-[4-(tert-Butoxycarbonylamino)butylamino]-2-chloro-3-nitroquiline 0.72 g (2.97 mmol) of 2,4-Dichloro-3-nitroquinoline and 0.56 g (2.97 mmol) of N-(tert-butoxycarbonyl)-1,4-diaminobutane were heated in 12 ml of triethylamine at 70° C. and stirred for 1.5 hours. After the reaction mixture was concentrated under reduced pressure, the residue was dissolved in methylene chloride, washed with water, and dried (MgSO$_4$). The solvent was distilled off under reduced pressure. The residue was triturated with n-hexane-diethyl ether (1:1 (v/v)) and collected by filtration to obtain 0.97 g (2.46 mmol) of 4-[4-(tert-butoxycarbonylamino)butylamino]-2-chloro-3-nitroquinoline shown below as yellow powder (mp: 125–126.5° C.).

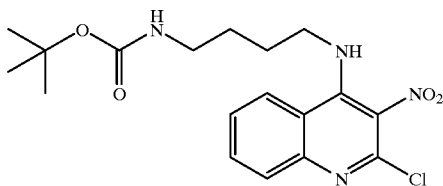

Its spectroscopic data are as follows:
IR (KBr) cm$^{-1}$ : 3340, 3280, 1680, 1540, 1520. $^1$H-NMR (CDCl$_3$) δ (ppm) :1.46 (9H, s), 1.63 (2H, m), 1.78 (2H, m), 3.19 (2H, q, J=6.4 Hz), 3.47 (2H, q, J=61 Hz), 4.68 (1H, br), 6.41 (1H, b r), 7.52 (1H, t, J=7.7 Hz), 7.74 (1H, t, J=7.8 Hz), 7.91 (1H, d, J=8.4 Hz), 8.11 (1H, d, J=8.4 Hz).

EXAMPLE 14

3-Amino-4- [4-(tert-butoxycarbonylamino)butylamino]-2-chloroquinoline 0.5 g (1.27 mmol) of 4-[4-(tert-Butoxycarbonylamino) butylamino]-2-chloro-3-nitroquinoline was dissolved in 13 ml of ethanol. 1.0 g (4.43 mmol) of tin chloride [II] dihydrate was added thereto and the mixture was refluxed under heating for one hour. The reaction mixture was poured into 2N aqueous ammonia. The resulting solution was extracted twice with chloroform, washed (brine), and dried (Na$_2$SO$_4$). The solvent was distilled off under reduce pressure and the residue was purified by silica gel column chromatography (n-hexane:ethyl acetate=2:1 (v/v)) to collect the product. After the solvent was distilled off, the resulting product was triturated with diethyl ether to obtain 0.12 g (0.329 mmol) of 3-amino-4-[4-(tert-butoxycarbonylamino)butylamino]-2-chloroquinoline shown below as orange crystals.

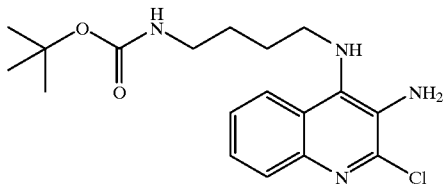

Its spectroscopic data are as follows:
IR (KBr) cm$^-$: 3270, 1680, 1540, 760. $^1$H-NMR (CDCl$_3$) δ (ppm) : 1.44 (9H, s), 1.64 (4H, m), 3.17 (2H, q, J=6.0 Hz), 3.27 (2H, t, J=6.6 Hz), 3.89 (1H, H, br), 4.15 (2H, br), 4.59 (1H, br), 7.47 (2H, m), 7.77 (1H, d, J=7.6 Hz), 7.89 (1H, d, J=7.2 Hz).

EXAMPLE 15

1-[4-(tert-Butoxycarbonylamino)butyl]-4-chloro-1H-imidazo[4,5-c]quinoline 0.32 ml (1.92 mmol)of Triethyl ortho-formate was added to 0.14 g (0.384 mmol) of 3-amino-4-[4-(tert-butoxycarbonylamino)butylamino]-2-chloroquinoline. The mixture was heated at 100° C. and stirred overnight. The reaction mixture was concentrated under reduced pressure and the resulting residue was purified by silica gel column chromatography (chloroform:methanol=150:1 to 100:1 (v/v)) to obtain 0.12 g (0.321 mmol) of 1-[4-(tert-butoxycarbonylamino)butyl]-4-chloro-1H-imidazo[4,5-c] quinoline as pale orange powder (mp: 148–150° C.).

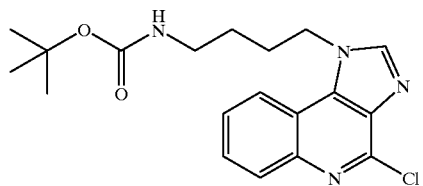

Its spectroscopic data are as follows:
IR (KBr) cm-1 : 1695, 1510.
$^1$H-NMR (CDCl$_3$) δ (ppm) :1.42 (9H, s), 1.62 (2H, m), 2.06 (2H, m), 3.21 (2H, q, J=6.4 Hz), 4.58 (1H, br), 4.65 (2H, t, J=7.4 Hz), 7.66 (1H, t, J=7.2 Hz), 7.72 (1H, t, J=7.6 Hz), 8.02 (1H, s), 8.13 (1H, d, J=8.4 Hz), 8.21 (1H, d, J=8.2 Hz).

EXAMPLE 16

1-(4-Aminobutyl)-4-chloro-1H-imidazo[4,5-c]quinoline 0.10 g (0.267 mmol) of 1-[4-(tert-butoxycarbonylamino) butyl]-4-chloro-1H-imidazo-[4,5-c]quinoline was dissolved in 6 ml of methylene chloride. 0.21 ml (2.67 mmol) of trifluoroacetic acid was added thereto and the mixture was concentrated under reduced pressure. 2 ml of a 1N sodium hydroxide aqueous solution and brine were added to the residue and the mixture was extracted five times with chloroform. The extract was dried (Na$_2$SO$_4$) and concentrated under reduced pressure. The residue was triturated with diethyl ether (containing a small amount of methylene chloride) and the precipitate thus formed was collected by filtration to obtain 45 mg (0.164 mmol) of 1-(4-aminobutyl)-4-chloro-1H-imidazo[4,5-c]quinoline (shown below) as pale orange powder.

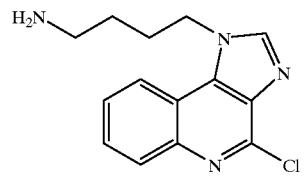

Its spectroscopic data are as follows:
IR (KBr) cm$^{-1}$: 3400, 2950, 1670, 1520, 1360.
$^1$H-NMR (CDCl$_3$) δ (ppm) :1.51 (2H, m), 1.96 (2H, m), 2.66 (2H, t, J=7.2 Hz), 3.03 (2H, b r), 4.53 (2H, t, J=7.4 Hz), 7.56 (1H, t, J=7.4 Hz), 7.60 (1H, t, J=7.5 Hz), 7.97 (1H, s), 8.02 (1H, d, J=6.4 Hz), 8.04 (1H, d, J=6.4 Hz).

EXAMPLE 17

1-(4-Aminobutyl)-1H-imidazo[4,5-c]quinoline-4-amine 40 mg (0.146 mmol) of 1-(4-aminobutyl)-4-chloro-1H-imidazo[4,5-c]quinoline, 8 ml of methanol and 4 ml of liquid ammonia were stirred overnight in an autoclave under heating at 150° C. The reaction mixture was concentrated under reduced pressure, the residue was dissolved in a small amount of water and 0.5 ml of a 1N sodium hydroxide aqueous solution was added thereto. The precipitate thus formed was collected by filtration and recrystallized from ethanol to obtain 14 mg (0.0548 mmol) of 1-(4-aminobutyl)-1H-imidazo[4,5-c]quinoline(shown below) -4-amine as pale yellowish green crystals (mp: 227–230.5° C. (decomposition)).

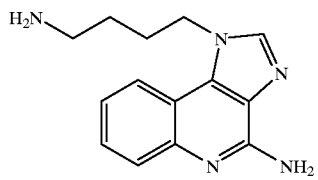

Its spectroscopic data are as follows:
IR (KBr) cm$^{-1}$: 3340, 3180, 1650, 1530, 1400.
$^1$H-NMR (DMSO-d$_6$) δ (ppm): 1.30 (2H, br), 1.39 (2H, m), 1.89 (2H, m), 2.55 (2H, t, J=6.8 Hz), 4.59 (2H, t, J=7.0 Hz), 6.56 (2H, br), 7.26 (1H, t, J=7.4 Hz), 7.44 (1H, t, J=7.7 Hz), 7.62 (1H, d, J=8.0 Hz), 8.05 (1H, d, J=8.0 Hz), 8.19 (1H, s).

EXAMPLE 18

4-Benzylamino-1-[4-(tert-butoxycarbonylamino)butyl]-1H-imidazo-[4,5-c]quinoline 2 ml of benzylamine was added to 70 mg (0.187 mmol) of 1-[4-(tert-butoxycarbonylamino)butyl]-4-chloro-1H-imidazo-[4,5-c]quinoline. The resulting mixture was heated at 150° C. and stirred for 3 hours. An excess amount of benzylamine was distilled off under reduced pressure and 1N hydrochloric acid and brine were added thereto. The resulting solution was extracted twice with methylene chloride. The organic phase was washed with a saturated sodium hydrogencarbonate aqueous solution and dried (Na$_2$SO$_4$). The solvent was then distilled off under reduced pressure. The residue was purified by silica gel column chromatography (chloroform:methanol=150:1 (v/v)) to obtain 79 mg (0.177 mmol) of 4-benzylamino-1-[4-(tert-butoxycarbonylamino)butyl]-1H-imidazo[4,5-c]quinoline shown below as white powder (mp: 151 to 153.5° C.).

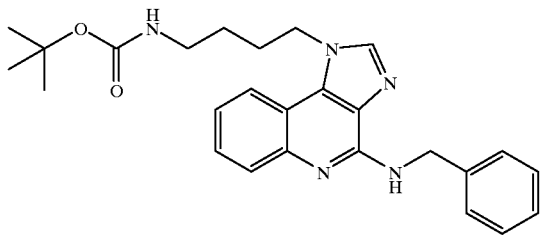

Its spectroscopic data are as follows:
IR (KBr) cm$^{-1}$: 3380, 3310, 2930, 1680, 1595, 1540, 1245, 1160.
$^1$H-NMR (CDCl$_3$) δ (ppm): 1.42 (9H, s), 1.58 (2H, m), 2.02 (2H, m), 3.18 (2H, m), 4.55 (2H, t, J=7.4 Hz), 4.55 (1H, br), 4.95 (2H, d, J=5.6 Hz), 6.03 (1H, t, J=5.6 Hz), 7.23~7.36 (4H, m), 7.47 (2H, d, J=7.6 Hz), 7.51 (1H, t, J=7.8 Hz), 7.75 (1H, s), 7.90 (2H, d, J=8.0 Hz).

EXAMPLE 19

1-(4-Aminobutyl)-1H-imidazo[4,5-c]quinoline-4-amine 67 mg (0.150 mmol) of 4-Benzylamino-1-[4-(tert-butoxycarbonylamino)butyl]-1H-imidazo[4,5-c]quinoline was dissolved in 5 ml of formic acid. 0.15 g of 20% palladium hydroxide-carbon was added thereto and the mixture was refluxed for 2 days under heating. The reaction mixture was filtered and the solvent was distilled off under reduced pressure. The residue was purified by silica gel column chromatography (chloroform:methanol:32% acetic acid=6:3:1 (v/v)) to obtain the acetic acid salt of the object. The product was treated with alkali and the solid was collected by filtration to obtain 14 mg (0.0548 mmol) of 1-(4-aminobutyl)-1H-imidazo[4,5-c]quinoline-4-amine shown below as faint brown powder.

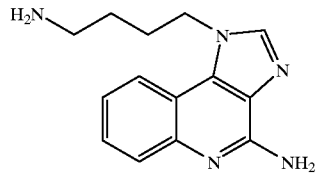

The physicochemical properties of this compound was in agreement with those of the compound of Example 17.

EXAMPLE 20

1-(5-Aminopentyl)-1H-imidazo[4,5-c]quinoline-4-amine 1-(5-Aminopentyl)-1H-imidazo[4,5-c]quinoline-4-amine shown below was synthesized using 2,4-dichloro-3-nitroquinoline and N-(tert-butoxycarbonyl)-1,5-diaminopentane as starting materials in the same manner as in Examples 13 to 17.

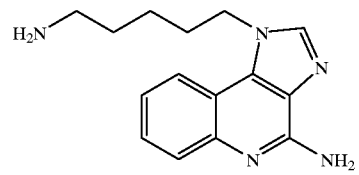

Its spectroscopic data are as follows:
IR (KBr) cm$^{-1}$: 3320, 3150, 2950, 1650, 1580, 1520, 1480, 1420, 1400, 1250, 760.
$^1$H-NMR (DMSO-d$_6$) δ (ppm): 1.36 (4H, m), 1.86 (2H, m), 2.50 (2H, m), 4.58 (2H, t, J=7.2 Hz), 6.55 (2H, s), 7.26 (1H, t, J=7.6 Hz), 7.44 (1H, t, J=7 Hz), 7.62 (1H, d, J=8.4 Hz), 8.02 (1H, d, J=8.0 Hz), 8.19 (1H, s).

EXAMPLE 21

1-(6-Aminohexyl)-1H-imidazo[4,5-c]quinoline-4-amine 1-(6-Aminohexyl)-1H-imidazo[4,5-c]quinoline-4-amine shown below was synthesized using 2,4-dichloro-3-nitroquinoline and N-(tert-butoxycarbonyl)-1,6-diaminohexane as starting materials in the same manner as in Examples 13 to 17.

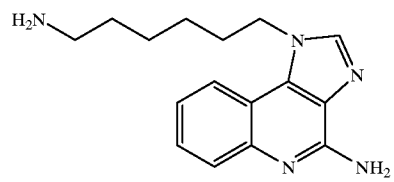

Its spectroscopic data are as follows:
IR (KBr) cm$^{-1}$: 3330, 3140, 2940, 1650, 1580, 1530, 1480, 1395, 1250, 750.
$^1$H-NMR (DMSO-d$_6$) δ (ppm): 1.31 (6H, m), 1.86 (2H, m), 2.50 (2H, m), 4.58 (2H, t, J=7.2 Hz), 6.54 (2H, s), 7.26 (1H, t, J=7.6 Hz), 7.44 (1H, t, J=7.4 Hz), 7.62 (1H, d, J=8.4 Hz), 8.03 (1H, d, J=8.0 Hz), 8.18 (1H, s).

EXAMPLE 22

3-Amino-4-[4-(tert-butoxycarbonylamino)butylamino]quinoline 38.69 mg (97.98 mmol) of 4-[4-(tert-butoxycarbonylamino)butylamino]-2-chloro-3- nitroquinoline was dissolved in 900 ml of methanol. 10 g of 10% palladium-carbon was added thereto and the mixture was stirred for 2 days under hydrogen atmosphere. The reaction mixture was filtrated and the filtrate was concentrated under reduced pressure. A sodium hydrogencarbonate aqueous solution was added to the residue and the solution was extracted twice with chloroform. The organic phase was washed with brine and dried ($Na_2SO_4$). The solvent was distilled off and the residue was purified by silica gel column chromatography (chloroform:methanol=50:1 to 10:1 (v/v)) to obtain 21.37 mg (64.67 mmol) of 3-amino-4-[4-(tert-butoxycarbonylamino)butylamino] quinoline shown below as a green brown amorphous substance.

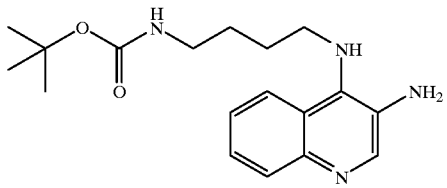

Its spectroscopic data are as follows:
$^1$H-NMR ($CDCl_3$) δ (ppm): 1.44 (9H, s), 1.64 (4H, m), 3.16 (2H, m), 3.26 (2H, t, J=6.8 Hz), 3.8 (2H, br) 4.6 (1H, br), 7.45 (2H, m), 7.82 (1H, m), 7.97 (1H, m), 8.47 (1H, s).

EXAMPLE 23
4-[4-(tert-butoxycarbonylamino)butylamino]-3-nitroquinoline 3.59 g (19.08 mmol) of N-(tert-butoxycarbonyl)-1,4-diaminobutane was dissolved in 70 ml of triethylamine and 3.79 g (18.17 mmol) of 4-chloro-3-nitroquinoline was added thereto. The resulting mixture was heated at 70° C. and stirred for 4 hours. After the reaction mixture was concentrated under reduced pressure, the residue was dissolved in chloroform, washed with water, and dried ($MgSO_4$). The solvent was distilled off under reduced pressure. The resulting residue was triturated with diethel ether and collected by filtration to obtain 5.77 g (16.01 mmol) of 4-[4-(tert-butoxycarbonylamino)butylamino]-3-nitroquinoline shown below as a yellow solid.
Its spectroscopic data are as follows:

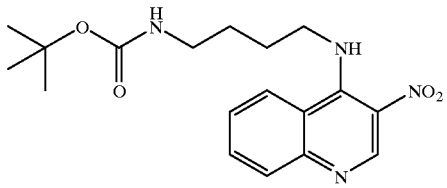

IR (KBr) cm$^{-1}$: 3330, 2980, 1710, 1600, 1510, 1260, 1180, 1130, 760, 700.
$^1$H-NMR ($CDCl_3$) δ (ppm): 1.44 (9H, s), 1.68 (2H, m), 1.88 (2H, m), 3.21 (2H, q, J=6.5 Hz), 3.99 (2H, q, J=6.3 Hz), 4.60 (1H, br), 7.49 (1H, t, J=7.6 Hz), 7.77 (1H, t, J=7.6 Hz), 8.00 (1H, d, J=8.4 Hz), 8.30 (1H, d, J=8.8 Hz), 9.37 (1H, s) 9.69 (1H, br).

EXAMPLE 24
3-Amino-4-[4-(tert-butoxycarbonylamino)butylamino] quinoline 1.80 g (5.0 mmol) of 4-[4-(tert-butoxycarbonylamino) butylamino]-3-nitroquinoline) was dissolved to a mixed solvent of 30 ml of methanol and 10 ml of ethyl acetate. 0.5 g of 10% palladium-carbon was added thereto and the mixture was stirred overnight under hydrogen atomsphere. The reaction mixture was filtered and the filtrate was concentrated under reduced pressure. The residue was purified by silica gel column chromatography (chloroform:methanol=50:1 to 10:1 (v/v)) to obtain 1.15 g (3.48 mmol) of 3-amino-4-[4-(tert-butoxycarbonylamino) butylamino]quinoline shown below as a brown amorphous substance.

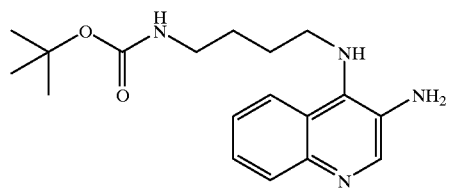

Its physicochemical properties were in agreement with those of the compound of Example 22.

EXAMPLE 25
1-[4-(tert-butoxycarbonylamino)butyl]-1H-imidazo[4,5-c] quinoline 21.37 g (64.67 mmol) of 3-amino-4-[4-(tert-butoxycarbonylamino)butylamino]quinoline was heated at 100° C. in 43.0 ml (258.7 mmol) of triethyl ortho-formate and stirred for 5 hours. The reaction mixture was concentrated to dryness, triturated with diethyl ether, and collected by filtration to obtain 19.49 g (57.25 mmol) of 1-[4-(tert-butoxycarbonylamino)butyl]-1H-imidazo[4,5-c]quinoline shown below as faint yellowish white powder.
Its spectroscopic data are as follows:
IR (KBr) cm$^{-1}$: 3230, 3040, 2940, 1690, 1560, 1

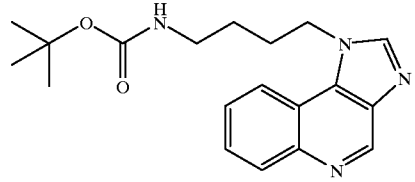

365, 1280, 1170, 880, 760.
$^1$H-NMR ($CDCl_3$) δ (ppm): 1.42 (9H, s), 1.62 (4H, m), 2.07 (2H, m), 3.21 (2H, m), 4.57 (1H, br), 4.65 (2H, t, J=7.2 Hz), 7.66 (1H, t, J=7.5 Hz),7.72 (1H, t, J=7.6 Hz), 7.99 (1H, s), 8.17 (1H, d, J=8.2 Hz), 8.30 (1H, d, J=8.4 Hz), 9.35 (1H, s).

EXAMPLE 26
1-[4-(tert-Butoxycarbonylamino)butyl]-1H-imidazo[4,5-c] quinoline-5-oxide 19.47 g (57.19 mmol) of 1-[4-(tert-Butoxycarbonylamino)butyl]-1H-imidazo[4,5-c]quinoline was dissolved in 500 ml of methylene chloride and 15.51 g (62.91 mmol) of 70% m-chloroperbenzoic acid was added thereto. The resulting mixture was stirred overnight at room temperature. A sodium hydrogencarbonate aqueous solution was added to the reaction mixture and the reaction mixture was extracted twice with chloroform. The organic phase was washed with brine and dried ($Na_2SO_4$). The solvent was distilled off under reduced pressure and the residue was purified by aluminum column chromatography (chloroform:methanol=50:1 to 10:1 (v/v)). Finally, the resulting product was triturated with diethyl ether and collected by filtration to obtain 15.88 g (44.55 mmol) of 1-[4-(tert-butoxycarbonylamino)butyl]-1H-imidazo[4,5-c]quinoline-5-oxide shown below as yellowish white powder.

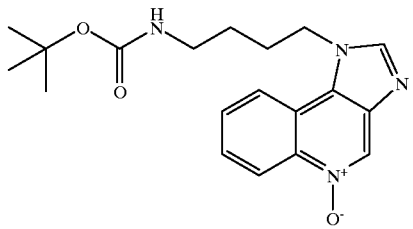

Its spectroscopic data are as follows:
IR (KBr) cm$^{-1}$: 3280, 2970, 1710, 1540, 1365, 1250, 1170, 1140, 850, 760, 630.
$^1$H-NMR (CDCl$_3$) δ (ppm): 1.42 (9H, s), 1.63 (2H, m), 2.06 (2H, m), 3.22 (2H, m), 4.63 (2H, t, J=7.2 Hz), 7.79 (2H, m), 8.00 (1H, s), 8.15 (1H, m), 9.06 (1H, m), 9.08 (1H, s).

EXAMPLE 27

1-[4-(tert-Butoxycarbonylamino)butyl]-1H-imidazo[4,5-c]quinoline-4-amine 15.87 g (44.52 mmol) of 1-[4-(tert-butoxycarbonylamino)butyl]-1H-imidazo[4,5-c]quinoline-5-oxide was dissolved in 400 ml of methylene chloride and 200 ml of concentrated aqueous ammonia (29%) was added thereto under ice-cooling. A solution of p-toluenesulfonyl chloride (9.34 g, 48.98 mmol) in 50 ml of methylene was further added thereto and the mixture was stirred for 30 minutes, then rasing up to room temperature stirred for 2 hours. After the reaction solution was separated, the organic phase was washed with brine and dried (Na$_2$SO$_4$). The solvent was distilled off and the residue was triturated with chloroform, then collected by filtration to obtain 7.10 g (19.97 mmol) of 1-[4-(tert-butoxycarbonylamino)butyl]-1H-imidazo[4,5-c]-quinoline-4-amine shown below as a faint yellowish white solid.

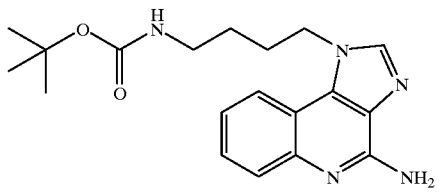

Its spectroscopic data are as follows:
IR (KBr) cm$^{-1}$: 3440, 3380, 3110, 2980, 1710, 1650, 1530, 1260, 1160, 760.
$^1$H-NMR (CDCl$_3$) δ (ppm): 1.43 (9H, s), 1.60 (2H, m), 2.03 (2H, m), 3.19 (2H, m), 4.57 (2H, t, J=7.2 Hz) 4.58 (1H, br), 5.46 (2H, br), 7.34 (1H, t, J=7.6 Hz),7.53 (1H, t, J=7.7 Hz),7.82 (1H, s), 7.83 (1H, d, J=8.4 Hz), 7.93 (1H, d, J=8.2 Hz).

EXAMPLE 28

1-(4-Aminobutyl)-1H-imidazo[4,5-c]quinoline-4-amine

One hundred ml of trifluoroacetic acid was added to 16.04 g (45.13 mmol) 1-[4-(tert-butoxycarbonylamino)butyl]-1H-imidazo[4,5-c]-quinoline-4-amine and the mixture was stirred overnight at room temperature. The reaction mixture was concentrated to dryness. A 2N sodium hydroxide solution aqueous solution (120 ml) was added thereto and the mixture was stirred. The precipitate thus formed was collected by filtration and washed with water and diethyl ether to obtain 9.64 g (37.76 mmol) of 1-(4-aminobutyl)-1H-imidazo[4,5-c]quinoline-4-amine shown below as a pale yellowish white solid.

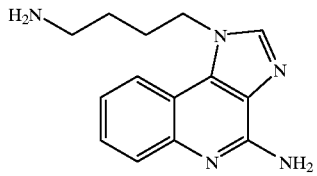

Its physicochemical properties were in agreement with those of the compound of Example 17.

EXAMPLE 29

3-Amino-4- [4-(tert-butoxycarbonylamino)butylamino]quinoline hydrochloride 2.50 g (6.33 mmol) of 4-[4-(tert-Butoxycarbonylamino)butylamino]-2-chloro-3-nitroquinoline was dissolved in 65 ml of methanol and 1 g of 10% palladium-carbon was added thereto. The mixture was stirred for one day under hydrogen atomosphere. The reaction mixture was filtered, the filtrate was concentrated under reduced pressure, and the residue was purified by silica gel column chromatography (chloroform:methanol=10:1 (v/v)). Finally, the resulting product was triturated with diethyl ether and collected by filtration to obtain 1.75 g (4.77 mmol) of 3-amino-4-[4-(tert-butoxycarbonylamino)butylamino]quinoline hydrochloride shown below as a yellow solid.

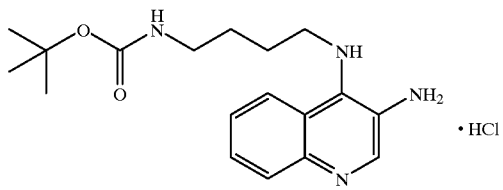

Its spectroscopic data are as follows:

IR (KBr) cm$^{-1}$: 3340, 2970, 1690, 1590, 1530, 1170.

$^1$H-NMR (CDCl$_3$) δ (ppm): 1.40 (9H, s), 1.68 (2H, m), 1.94 (2H, m), 3.17 (2H, m), 3.91 (2H, m), 5.04 (1H, br), 5.4 (2H, br), 7.10 (1H, br), 7.28 (1H, t, J=7.6 Hz), 7.51 (1H, t, J=7.6 Hz), 8.03 (2H, t, J=8.2 Hz), 8.57 (1H, s).

EXAMPLE 30

1- [4-(tert-Butoxycarbonylamino)butyl]-2-methyl-1H-imiazo[4,5-c]quinoline 0.66 g (1.80 mmol) of 3-Amino-4-[4-(tert-butoxycarbonylamino)butylamino]quinoline hydrochloride was heated at 100° C. in 1.47 ml (8.0 mmol) of triethyl ortho-acetate and the mixture was stirred overnight. The reaction mixture was concentrated to dryness and the residue was purified by silica gel column chromatography (chloroform:methanol=100:1 to 50:1 (v/v)) to obtain 0.55 g (1.55 mmol) of 1-[4-(tert-butoxycarbonylamino)butyl]-2-methyl-1H-imiazo[4,5-c]quinoline shown below as a pale yellow solid.

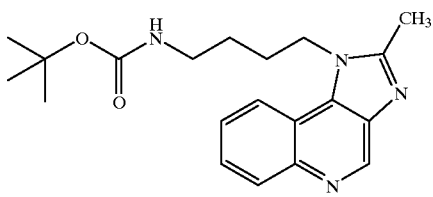

Its spectroscopic data are as follows:
IR (KBr) cm$^{-1}$: 3240, 2970, 1700, 1550, 1360, 1280, 1170, 760.
$^1$H-NMR (CDCl$_3$) δ (ppm): 1.42 (9H, s), 1.69 (2H, m), 2.01 (2H, m), 2.72 (3H, s), 3.21 (2H, m), 4.56 (2H, t, J=7.8 Hz), 4.57 (1H, br), 7.63 (1H, t, J=7.5 Hz), 7.68 (1H, t, J=7.6 Hz), 8.13 (1H, d, J=8.0 Hz), 8.28 (1H, d, J=8.2 Hz), 9.25 (1H, s).

EXAMPLE 31
1-[4-(tert-Butoxycarbonylamino)butyl]-2-methyl-1H-imidazo[4,5-c]quinoline-5-oxide 0.15 g (0.423 mmol) of 1-[4-(tert-butoxycarbonylamino)butyl]-2-methyl-1H-imidazo[4,5-c]quinoline) was dissolved in a mixed solvent of 5 ml of ethyl acetate and 5 ml of chloroform and 0.11 ml (0.508 mmol) of 32% peracetic acid was added thereto. The mixture was heated at 50° C. and stirred for 3 hours. After the reaction mixture was poured into a sodium hydrogencarbonate aqueous solution, the resulting solution was extracted with chloroform, dried (Na$_2$SO$_4$), then concentrated under reduced pressure. The residue was purified by silica gel column chromatography (chloroform:methanol=20:1 (v/v)) to obtain 0.13 g (0.351 mmol) of 1-[4-(tert-butoxycarbonylamino)butyl]-2-methyl-1H-imidazo[4,5-c]quinoline-5-oxide shown below as a white solid.

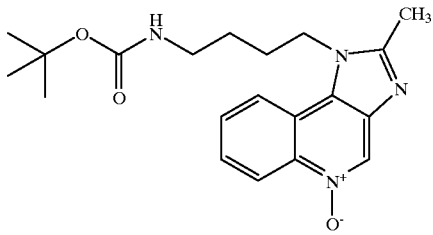

Its spectroscopic data are as follows:
IR (KBr) cm$^{-1}$: 3230, 2980, 1710, 1540, 1440, 1370, 1280, 1170, 880, 770.
$^1$H-NMR (CDCl$_3$) δ (ppm): 1.42 (9H, s), 1.70 (2H, m), 2.00 (2H, m), 2.70 (3H, s), 3.23 (2H, m), 4.53 (2H, t, J=7.8 Hz), 4.63 (1H, br), 7.76 (2H, m), 8.12 (1H, m), 9.01 (1H, s), 9.06 (1H, m).

EXAMPLE 32
1-[4-(tert-Butoxycarbonylamino)butyl]-2-methyl-1H-imidazo[4,5-c]quinoline-4-amine 0.124 g (0.335 mmol) of 1-[4-(tert-Butoxycarbonylamino)butyl]-2-methyl-1H-imidazo[4,5-c]quinoline-5-oxide was dissolved in 3 ml of methylene chloride. Two ml of concentrated aqueous ammonia (29%) and a solution of 70 mg (0.368 mg) of p-toluenesulfonyl chloride in 1 ml of methylene chloride were added thereto under ice-cooling and the mixture was stirred for 30 minutes, then stirred at room temperature for 3 hours. After brine was added, the reaction mixture was extracted with chloroform and dried (Na$_2$SO$_4$). The solvent was distilled off and the residue was purified by silica gel column chromatography (chloroform:methanol=30:1 to 20:1 (v/v)) to obtain 0.114 g (0.309 mmol) of 1-[4-(tert-butoxycarbonylamino)butyl]-2-methyl-1H-imidazo[4,5-c]quinoline-4-amine shown below as a pale brown solid.

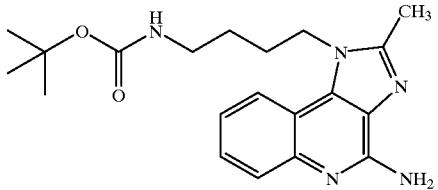

Its spectroscopic data are as follows:
IR (KBr) cm$^{-1}$: 3460, 3370, 3100, 1710, 1640, 1540, 1380, 1260, 1170, 750.
$^1$H-NMR (CDCl$_3$) δ (ppm): 1.42 (9H, s), 1.66 (2H, m), 1.97 (2H, m), 2.65 (3H, s), 3.20 (2H, m), 4.47 (2H, t, J=7.6 Hz), 4.58 (1H, br), 5.39 (2H, br), 7.32 (1H, t, J=7.6 Hz), 7.50 (1H, t, J=7.7 Hz), 7.82 (1H, d, J=8.4 Hz), 7.90 (1H, d, J=8.2 Hz).

EXAMPLE 33
1-(4-Aminobutyl)-2-methyl-1H-imidazo[4,5-c]quinoline-4-amine

Sixty mg (0.223 mmol) of 1-(4-aminobutyl)-1H-imidazo[4,5-c]quinoline-4-amine shown below was obtained as a faint brown solid using 98 mg (0.265 mmol) of 1-[4-(tert-butoxycarbonylamino)butyl]-2-methyl-1H-imidazo[4,5-c]quinoline-4-amine as a starting material in the same manner as in Example 28.

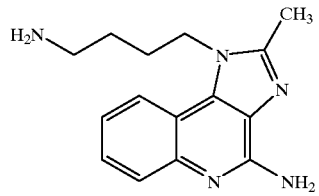

Its spectroscopic data are as follows:
IR (KBr) cm$^{-1}$: 3300, 3080, 1620, 1590, 1540, 1480, 1430, 1380, 1260, 850, 750.
$^1$H-NMR (DMSO-d$_6$) δ (ppm): 1.48 (2H, m), 1.85 (2H, m), 2.58 (2H, t, J=7.0 Hz), 2.60 (3H, s), 4.49 (2H, t, J=7.5 Hz), 6.45 (2H, s), 7.25 (1H, t, J=7.6 Hz), 7.40 (1H, t, J=7.8 Hz), 7.60 (1H, d, J=8.0 Hz), 8.04 (1H, d, J=8.0 Hz).

EXAMPLE 34
4-(4-Phthalimidebutylamino)-2-chloro-3-nitroquinoline (1) 5.41 g (28.74 mmol) of N-(tert-butoxycarbonyl)-1,4-diaminobutane was dissolved in 100 ml of 1,4-dioxane and 4.86 g (28.74 mmol) of N-carboethoxyphthalimide was added thereto. The mixture was heated at 45 to 60° C. and stirred for 4 hours. After the reaction mixture was concentrated under reduced pressure, 1N hydrochloric acid was added thereto and the resulting solution was extracted with ethyl acetate. The extract was washed with brine and dried (Na$_2$SO$_4$). The solvent was distilled off and the residue was purified by silica gel column chromatography (chloroform:methanol=200:1 (v/v)) to obtain 5.40 g (16.96 mmol) of N-[4-(tert-butoxycarbonylamino)butyl] phthalimide as a white solid. Its spectroscopic data are as follows:
$^1$H-NMR (CDCl$_3$) δ (ppm): 1.43 (9H, s), 1.53 (2H, m), 1.71 (2H, m), 3.16 (2H, m), 3.71 (2H, t, J=7.0 Hz), 4.55 (1H, br), 7.71 (2H, dd, J=5.8 Hz, 3.0 Hz), 7.84 (2H, dd, J=5.4 Hz, 3.0 Hz).

(2) 5.13 g (16.11 mmol) of N-[4-(tert-butoxycarbonylamino)butyl]phthalimide was dissolved in 100 ml of methylene chloride and 6.21 ml (80.56 mmol) of trifluoroacetic acid was added thereto. The mixture was stirred overnight at room temperature. The reaction mixture was concentrated to dryness, then dried by heating in vacuum at 50° C. to obtain 5.35 g (16.10 mmol) of N-(4-aminobutyl)phthalimide trifluoroacetate as a pale brown solid.

Its spectroscopic data are as follows:

$^1$H-NMR (CDCl$_3$) δ (ppm): 1.78 (4H, m), 3.13 (2H, m), 3.72 (2H, t, J=6.2 Hz), 7.72 (2H, dd, J=5.7 Hz, 3.1 Hz), 7.81 (2H, dd, J=5.4 Hz, 3.0 Hz).

(3) 5.26 g (15.83 mmol) of N-(4-aminobutyl)phthalimide trifluoroacetate and 3.85 g (15.83 mmol) of 2,4-dichloro-3-nitroquinoline were heated in 70 ml of triethylamine at 70° C. and stirred for 1.5 hours. After the reaction mixture was concentrated under reduced pressure, water was added thereto and the resulting solution was extracted with methylene chloride. The extract was dried (Na$_2$SO$_4$) and the solvent was distilled off. The residue was purified by silica gel column chromatography (chloroform:methanol=150:1 (v/v)). Finally, the purified product was triturated with diethyl ether and collected by filtration to obtain 3.83 g (9.01 mmol) of 4-(4-phthalimidebutylamino)-2-chloro-3-nitroquinoline shown below as a yellow solid.

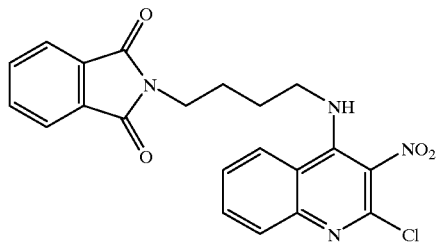

Its spectroscopic data are as follows:

IR (KBr) cm$^{-1}$: 3410, 1770, 1710, 1580, 1530, 1440, 1400, 1380, 1050, 760, 720.

$^1$H-NMR (CDCl$_3$) δ (ppm): 1.82 (4H, m), 3.50 (2H, m), 3.77 (2H, t, J=6.6 Hz), 6.0 (1H, br), 7.55 (1H, t, J=7.7 Hz), 7.73 (2H, dd, J=5.4 Hz, 3.0 Hz), 7.74 (1H, t, J=7.7 Hz), 7.85 (2H, dd, J=5.3 Hz, 3.1 Hz), 7.91 (1H, d, J=8.4 Hz), 7.98 (1H, d, J=8.4 Hz).

EXAMPLE 35

3-Amino-4-(4-phthalimidebutylamino)quinoline hydrochloride 2.0 g (4.71 mmol) of 4-(4-Phthalimidebutylamino)-2-chloro-3-nitroquinoline was dissolved in a mixed solvent of 90 ml of methanol and 60 ml of methylene chloride. One g of 10% Palladium-carbon was added thereto and the mixture was stirred overnight under hydrogen atmosphere. The reaction mixture was filtered and the filtrate was concentrated under reduced pressure. The residue was triturated with diethyl ether and collected by filtration to obtain 1.33 g (3.35 mmol) of 3-amino-4-(4-phthalimidebutylamino)quinoline hydrochloride shown below as a yellow solid.

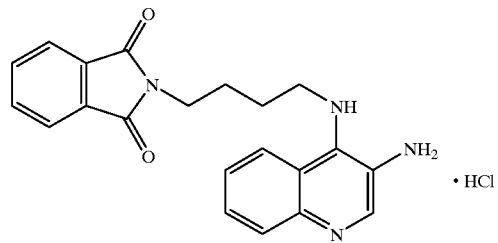

Its spectroscopic data are as follows:

IR (KBr) cm$^{-1}$: 3370, 3190, 2670, 1765, 1700, 1580, 1520, 1410, 1380, 1330, 725.

$^1$H-NMR (DMSO-d$_6$) δ (ppm): 1.70 (2H, m), 2.08 (2H, m), 3.60 (2H, m), 3.88 (2H, m), 5.27 (2H, br), 7.41 (1H, br), 7.51 (1H, t, J=7.7 Hz), 7.70 (1H, t, J=7.8 Hz), 7.81 (1H, d, J=8.4 Hz), 7.84 (4H, s), 8.18 (1H, s), 8.35 (1H, d, J=8.8 Hz).

EXAMPLE 36

2-Ethoxymethyl-1-(4-phthalimidebutyl)-1H-imidazo[4,5-c]quinoline 1.21 ml (12.82 mmol) of ethoxyacetic acid was added to 0.66 g (1.66 mmol) of 3-Amino-4-(4-phthalimidebutylamino)quinoline hydrochloride. The reaction mixture was heated at 120° C. and stirred for 7 hours. After cooling, 1N sodium hydroxide aqueous solution was added thereto and the resulting solution was extracted twice with chloroform. The extract was washed with brine and dried (Na$_2$SO$_4$). The solvent was distilled off under reduced pressure and the residue was purified by silica gel column chromatography (chloroform:methanol=150:1 (v/v)) to obtain 0.59 g (1.38 mmol) of 2-ethoxymethyl-1-(4-phthalimidebutyl)-1H-imidazo[4,5-c]quinoline as a pale yellowish white solid.

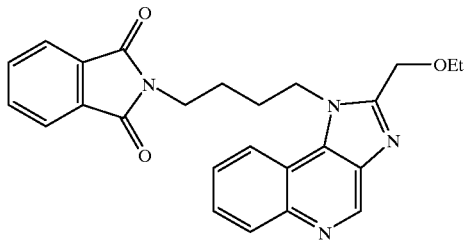

Its spectroscopic data are as follows:

IR (KBr) cm$^{-1}$: 3460, 2980, 2940, 1770, 1700, 1400, 1360, 1330, 1100, 1040, 760, 730.

$^1$H-NMR (CDCl$_3$) δ (ppm): 1.18 (3H, t, J=7.0 Hz), 1.96 (2H, m), 2.08 (2H, m), 3.59 (2H, q, J=6.9 Hz), 3.79 (2H, t, J=6.8 Hz), 4.69 (2H, t, J=7.9 Hz), 4.88 (2H, s), 7.60 (1H, t, J=7.5 Hz), 7.66 (1H, t, J=7.8 Hz), 7.72 (2H, dd, J=5.6 Hz, 3.2 Hz), 7.83 (2H, dd, J=5.4 Hz, 3.4 Hz), 8.11 (1H, d, J=8.0 Hz), 8.26 (1H, d, J=8.2 Hz), 9.28 (1H, s).

EXAMPLE 37

2-Ethoxymethyl-1-(4-phthalimidebutyl)-1H-imidazo[4,5-c]quinoline-5-oxide 0.57 g (1.33 mmol) of 2-Ethoxymethyl-1-(4-phthalimidebutyl)-1H-imidazo[4,5-c]quinoline was dissolved in 25 ml of methylene chloride and 0.36 g (1.46 mmol) of 70% m-chloroperbenzoic acid was added thereto. The mixture was stirred overnight at room temperature. The reaction mixture was poured into a sodium hydrogencarbonate aqueous solution and extracted with chloroform. The extract was washed with water, dried (Na$_2$SO$_4$). The solvent was distilled off and the residue was purified by silica gel column chromatography (chloroform:methanol=70:1 to 30:1 (v/v)). Finally, the purified product was triturated with diethyl ether and collected by filtration to obtain 0.52 g (1.17 mmol) of 2-ethoxymethyl-1-(4-phthalimidebutyl)-1H-imidazo[4,5-c]quinoline-5-oxide shown below as a light brown solid.

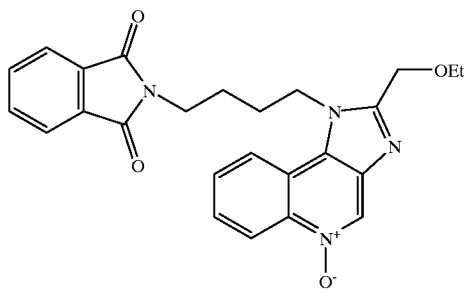

Its spectroscopic data are as follows:
IR (KBr) cm$^{-1}$: 3420, 2980, 1770, 1710, 1400, 1360, 1160, 1150, 1090, 890, 720.
$^1$H-NMR (CDCl$_3$) δ (ppm): 1.19 (3H, t, J=7.0 Hz), 1.96 (2H, m), 2.06 (2H, m), 3.60 (2H, q, J=7.1 Hz), 3.79 (2H, t, J=6.8 Hz), 4.66 (2H, t, J=7.8 Hz), 4.84 (2H, s), 7.73 (2H, dd, J=5.4 Hz, 3.0 Hz), 7.74 (2H, m), 7.82 (2H, dd, J=5.6 Hz, 3.2 Hz), 8.10 (1H, m), 9.02 (1H, s), 9.04 (1H, m).

EXAMPLE 38
2-Ethoxymethyl-1-(4-phthalimidebutyl)-1H-imidazo[4,5-c]quinoline-4-amine 0.45 g (1.01 mmol) of 2-Ethoxymethyl-1-(4-phthalimidebutyl)-1H-imidazo[4,5-c]quinoline-4-amine shown below was obtained as a pale yellowish white solid using 0.50 g (1.12 mol) of 2-ethoxymethyl-1-(4-phthalimidebutyl)-1H-imidazo[4,5-c]quinoline-5-oxide as a starting material in the same manner as in Example 27.

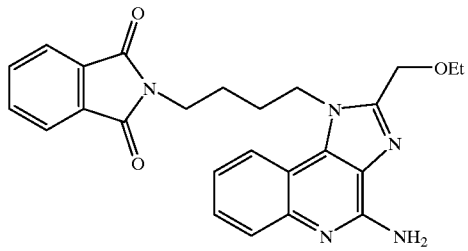

Its spectroscopic data are as follows:
IR (KBr) cm$^{-1}$: 3340, 3170, 1770, 1710, 1620, 1540, 1400, 1080, 760, 720.
$^1$H-NMR (CDCl$_3$) δ (ppm): 1.18 (3H, t, J=6.8 Hz), 1.93 (2H, m), 2.05 (2H, m), 3.58 (2H, q, J=6.9 Hz), 3.78 (2H, t, J=6.8 Hz), 4.61 (2H, t, J=7.8 Hz), 4.80 (2H, s), 5.45 (2H, br), 7.28 (1H, t, J=7.4 Hz), 7.48 (1H, t, J=7.6 Hz), 7.72 (2H, dd, J=5.4 Hz, 3.0 Hz), 7.79 (1H, d, J=8.6 Hz), 7.83 (2H, dd, J=5.2 Hz, 3.2 Hz), 7.88 (1H, d, J=8.6 Hz).

EXAMPLE 39
1-(4-Aminobutyl)-2-ethoxymethyl-1H-imidazo[4,5-c]quinoline-4-amine 0.44 g (0.992 mmol) of 2-Ethoxymethyl-1-(4-phthalimidebutyl)-1H-imidazo[4,5-c]quinoline-4-amine was dissolved in 20 ml of ethanol and 0.30 ml (4.96 mmol) of 80% hydrazine hydrate was added thereto. The mixture was refluxed under heating for 4 hours. After the reaction mixture was concentrated to dryness, 4 ml of 0.5 N sodium hydroxide aqueous solution was added to the residue and the solution was stirred. The precipitate thus formed was collected by filtration, washed with water and diehtyl ether, and dried in vacuum to obtain 0.27 g (0.861 mmol) of 1-(4-Aminobutyl)-2-ethoxymethyl-1H-imidazo[4,5-c]quinoline-4-amine as a yellowish white solid.

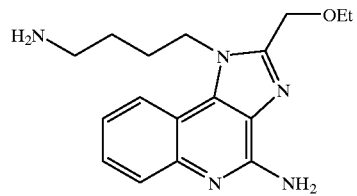

Its spectroscopic data are as follows:
IR (KBr) cm$^{-1}$: 3310, 3130, 1640, 1590, 1530, 1480, 1440, 1390, 1090, 750.
$^1$H-NMR (CDCl$_3$) δ (ppm): 1.25 (3H, t, J=7.2 Hz), 1.66 (2H, m), 2.04 (2H, m),2.80 (2H, t, J=7.2 Hz), 3.61 (2H, q, J=6.9 Hz),4.60 (2H, t, J=8.2 Hz), 4.81 (2H, s), 5.43 (2H, br), 7.34 (1H, t, J=7.6 Hz), 7.53 (1H, t, J=7.7 Hz), 7.83 (1H, d, J=8.4 Hz), 7.97 (1H, d, J=8.0 Hz).

EXAMPLE 40
1-(4-{[α-(2-Dimethylaminoethoxy)-α-phenyl-p-toluoyl]amino}butyl)-1H-imidazo[4,5-c]quinoline-4-amine 0.44 g (1.47 mmol) of α-(2-Dimethylaminoethoxy)-α-phenyl-p-toluic acid was suspended in 10 ml of chloroform. 0.21 ml (2.94 mmol) of thionyl chloride was added thereto, and the mixture was refluxed under heating for 2.5 hour. The reaction solution was concentrated under reduced pressure to obtain a crude product of acid chloride.

0.38 g (1.47 mmol) of 1-(4-Aminobutyl)-1H-imidazo[4,5-c]quinoline-4-amine was dissolved in a mixed solvent of 22 ml of ethanol and 15 ml of water and 1.47 ml of a 1N sodium hydroxide aqueous solution was added thereto. Under ice-cooling, 5 ml of a suspension of the acid chloride product as obtained above in chloroform was added thereto and the mixture was stirred for 20 minutes. The reaction mixture was poured into a sodium hydrogencarbonate aqueous solution and extracted with chloroform and then a chloroform-methanol (10:1 (v/v)) mixed solution. The organic phase was dried (Na$_2$SO$_4$), the solvent was distilled off, and the residue was purified by aluminum column chromatography (chloroform:methanol=200:1 to 30:1 (v/v)). Finally, the purified product was triturated with ether and collected by filtration to obtain 0.44 g (0.820 mmol) of 1-(4-{[α-(2-dimethylaminoethoxy)-α-phenyl-p-toluoyl]amino}butyl)-1H-imidazo[4,5-c]quinoline-4-amine as faint orange white powder (mp: 110 to 114° C.).

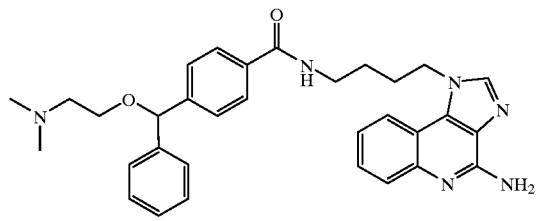

Its spectroscopic data are as follows:
IR (KBr) cm$^{-1}$: 3330, 2950, 1640, 1530, 1480, 1400, 1310, 1250, 1100, 750, 700.
$^1$H-NMR (CDCl$_3$) δ (ppm): 1.70 (2H, m), 2.07 (2H, m), 2.27 (6H, s), 2.60 (2H, t, J=6.0 Hz), 3.50 (2H, q, J=6.6 Hz), 3.56 (2H, td, J=6.0 Hz, 2.4 Hz), 4.60 (2H, t, J=7.2 Hz), 5.39 (1H, s), 5.46 (2H, br), 6.11 (1H, m), 7.23~7.33 (6H, m), 7.40 (2H, d, J=8.4 Hz), 7.48 (1H, t, J=7.7 Hz), 7.63 (2H, d, J=8.4 Hz), 7.81 (1H, d, J=8.4 Hz), 7.83 (1H, s), 7.92 (1H, d, J=8.0 Hz).

EXAMPLE 41

1-[4-(3-{4-[α-(2-Dimethylaminoethoxy)benzyl]phenyl}propanoyl-amino)butyl]-1H-imidazo[4,5-c]quinoline-4-amine 34 mg (0.0602 mmol) of 1-[4-(3-{4-[α-(2-dimethylaminoethoxy)benzyl]phenyl}-propanoylamino)butyl]-1H-imidazo[4,5-c]quinoline-4-amine shown below was obtained as faint yellowish white powder using 75 mg (0.229 mmol) of 3-[4-[α-(2-dimethylaminoethoxy)benzyl]phenyl}propionic acid as a starting material in the same manner as in Example 40.

toluic acid as a starting material in the same manner as in Example 40.

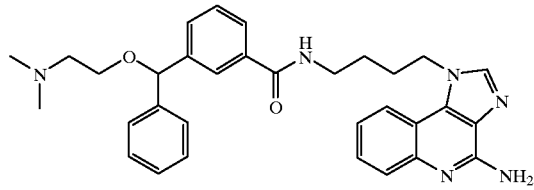

Its spectroscopic data are as follows:
IR (KBr) cm$^{-1}$: 3320, 2950, 1630, 1580, 1530, 1480, 1390, 1250, 1100, 750, 700.
$^1$H-NMR (CDCl$_3$) δ (ppm): 1.73 (2H, m), 2.09 (2H, m), 2.24 (6 H, s), 2.58 (2H, m), 3.51 (2H, q, J=6.6 Hz), 3.54 (2H, t, J=5.4 Hz), 4.60 (2H, t, J=7.2 Hz), 5.38 (1H, s), 5.45 (2H, br), 6.72 (1H, m), 7.22~7.41 (8H, m), 7.51 (1H, t, J=7.7 Hz), 7.66 (1H, d, J=7.6 Hz), 7.82 (1H, d, J=8.2 Hz), 7.85 (1H, s), 7.88 (1H, s), 7.94 (1H, d, J=8.0 Hz).

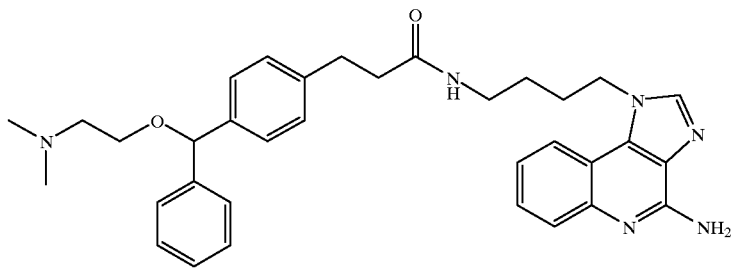

Its spectroscopic data are as follows:
IR (KBr) cm$^{-1}$: 3330, 2930, 1650, 1530, 1480, 1400, 1250, 1100, 750, 700.
$^1$H-NMR (CDCl$_3$) δ (ppm): 1.47 (2H, m), 1.89 (2H, m), 2.24 (6H, s), 2.39 (2H, t, J=7.6 Hz), 2.56 (2H, t, J=5.8 Hz), 2.89 (2H, t, J=7.6 Hz), 3.23 (2H, d, J=6.7 Hz), 3.52 (2H, t, J=5.8 Hz), 4.49 (2H, t, J=7.0 Hz), 5.29 (1H, s), 5.33 (1H, m), 5.48 (2H, br), 7.10 (2H, d, J=8.0 Hz), 7.16~7.36 (8H, m), 7.53 (1H, t, J=7.8 Hz), 7.79 (1H, s), 7.83 (1H, d, J=8.4 Hz) 7.90 (1H, d, J=8.0 Hz).

EXAMPLE 42

1-(4-{[α-(2-Dimethylaminoethoxy)-α-phenyl-m-toluoyl]amino}butyl)-1H-imidazo[4,5-c]quinoline-4-amine 0.18 g (0.335 mmol) of 1-(4-{[α-(2-dimethylaminoethoxy)-α-phenyl-m-toluoyl]amino}-butyl)-1H-imidazo[4,5-c]quinoline-4-amine shown below was obtained as faint yellowish white powder using 0.20 g (0.668 mmol) of α-(2-dimethylaminoethoxy)-α-phenyl-m-

EXAMPLE 43

1-(4-{[α-(3-Dimethylaminopropoxy)-α-phenyl-p-toluoyl]amino}butyl)-1H-imidazo[4,5-c]quinoline-4-amine 22 mg (0.0399 mmol) of 1-(4-{[α-(3-Dimethylaminopropoxy)-α-phenyl-p-toluoyl]amino}-butyl)-1H-imidazo[4,5-c]quinoline-4-amine shown below was obtained as white powder using 36 mg (0.115 mmol) of α-(3-Dimethylaminopropoxy)-α-phenyl-p-toluic acid as a starting material in the same manner as in Example 40.

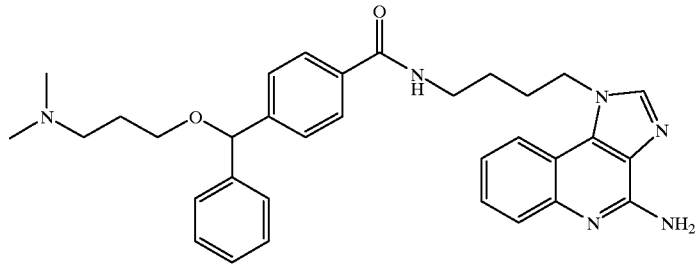

Its spectroscopic data are as follows:
IR (KBr) cm$^{-1}$: 3430, 3300, 2950, 1640, 1530, 1480, 1390, 1100, 750, 700.

¹H-NMR (CDCl₃) δ (ppm): 1.70 (2H, m), 1.82 (2H, m), 2.08 (2H, m), 2.38 (2H, t, J=7.6 Hz), 3.50 (4H, m), 4.60 (2H, t, J=7.2 Hz), 5.36 (1H, s), 5.46 (2H, br), 6.11 (1H, m), 7.23~7.35 (6H, m), 7.39 (2H, d, J=8.4 Hz), 7.48 (1H, t, J=7.7 Hz), 7.64 (2H, d, J=8.4 Hz), 7.81 (1H, d, J=8.4 Hz), 7.83 (1H, s), 7.92 (1H, d, J=8.2 Hz).

EXAMPLE 44

1-(4-{[α-(2-dimethylaminoethoxy)-α-phenyl-p-toluoyl]amino}butyl)-1H-imidazo[4,5-c]quinoline-4-amine 0.24 g (0.425 mmol) of 1-(4-{[α-(2-dimethylaminoethoxy)-α-phenyl-p-toluoyl]amino}-butyl)-1H-imidazo[4,5-c]quinoline-4-amine shown below was obtained as faint yellowish white powder using 0.18 g (0.550 mmol) of α-(2-diethylaminoethoxy)-α-phenyl-p-toluic acid in the same manner as in Example 40.

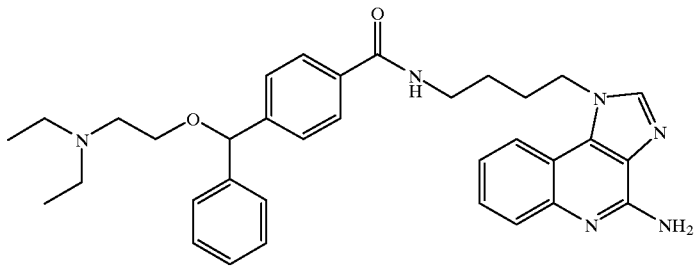

Its spectroscopic data are as follows:
IR (KBr) cm⁻¹: 3320, 2980, 1640, 1530, 1400, 1310, 1250, 1100, 1070, 750, 700.
¹H-NMR (CDCl₃) δ (ppm): 1.01 (6H, t, J=7.0 Hz), 1.70 (2H, m), 2.07 (2H, m), 2.56 (4H, q, J=7.2 Hz), 2.75 (2H, t, J=6.4 Hz), 3.50 (2H, q, J=6.5 Hz), 3.54 (2H, t, J=6.3 Hz), 4.60 (2H, t, J=7.2 Hz), 5.40 (1H, s), 5.47 (2H, br), 6.12 (1H, m), 7.22~7.33 (6H, m), 7.40 (2H, d, J=8.0 Hz), 7.48 (1H, t, J=7.6 Hz), 7.63 (2H, d, J=8.4 Hz), 7.82 (1H, d, J=8.4 Hz), 7.83 (1H, s), 7.92 (1H, d, J=8.0 Hz).

EXAMPLE 45

1-(6-{[α-(2-Dimethylaminoethoxy)-α-phenyl-p-toluoyl]amino}hexyl)-1H-imidazo[4,5-c]quinoline-4-amine 0.12 g, (0.212 mmol) of 1-(6-{[α-(2-dimethylaminoethoxy)-α-phenyl-p-toluoyl]amino}-hexyl)-1H-imidazo[4,5-c]quinoline-4-amine shown below was obtained as faint yellowish white powder using as starting materials 0.16 g (0.534 mmol) of α-(2-dimethylaminoethoxy)-α-phenyl-p-toluic acid and 0.14 g (0.494 mmol) of 1-(6-aminohexyl)-1H-imidazo[4,5-c]quinoline-4-amine in the same manner as in Example 40.

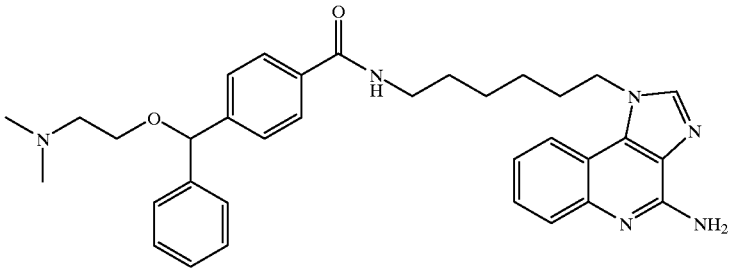

Its spectroscopic data are as follows:
IR (KBr) cm⁻¹: 3330, 3200, 2940, 1640, 1530, 1400, 1310, 1100, 750, 700.
¹H-NMR (CDCl₃) δ (ppm): 1.45 (4H, m), 1.60 (2H, m), 2.01 (2H, m), 2.26 (6H, s), 2.59 (2H, t, J=6.0 Hz), 3.43 (2H, q, J=6.9 Hz), 3.56 (2H, td, J=6.0 Hz, 2.0 Hz), 4.52 (2H, t, J=7.2 Hz), 5.39 (1H, s), 5.46 (2H, br), 6.04 (1H, m), 7.22~7.32 (5H, m), 7.33 (1H, t, J=7.6 Hz), 7.41 (2H, d, J=8.0 Hz), 7.52 (1H, t, J=7.6 Hz), 7.68 (2H, d, J=8.8 Hz), 7.80 (1H, s), 7.83 (1H, d, J=8.4 Hz), 7.94 (1H, d, J=8.4 Hz).

EXAMPLE 46

1-(4-{[α-(2-Dimethylaminoethoxy)-p-toluoyl]amino}butyl)-1H-imidazo[4,5-c]quinoline-4-amine 0.14 g (0.304 mmol) of 1-(4-{[α-(2-dimethylaminoethoxy)-p-toluoyl]amino}butyl)-1H-imidazo[4,5-c]quinoline-4-amine shown below was obtained as pale yellowish white powder using 0.13 g (0.582 mmol) of α-(2-dimethylaminoethoxy)-p-toluic acid as a starting material in the same manner as in Example 40.

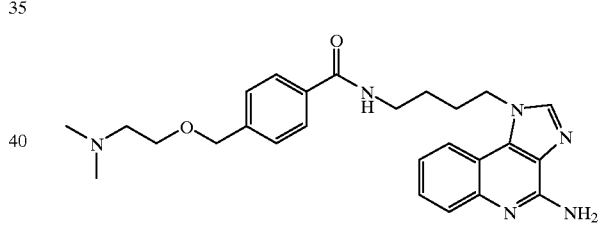

Its spectroscopic data are as follows:
IR (KBr) cm⁻¹: 3360, 3300, 3180, 2940, 1640, 1530, 1470, 1400, 1300, 1100, 750.
¹H-NMR (CDCl₃) δ (ppm): 1.72 (2H, m), 2.09 (2H, m), 2.27 (6H, s), 2.55 (2H, t, J=5.8 Hz), 3.51 (2H, q, J=6.7 Hz), 3.56 (2H, t, J=5.8 Hz), 4.57 (2H, s), 4.61 (2H, t, J=7.0 Hz), 5.46 (2H, br), 6.16 (1H, m), 7.30 (1H, t, J=7.7 Hz), 7.39 (2H, d, J=8.2 Hz), 7.52 (1H, t, J=7.8 Hz), 7.67 (2H, d, J=8.4 Hz), 7.83 (1H, d, J=8.4 Hz), 7.85 (1H, s), 7.94 (1H, d, J=8.4 Hz).

EXAMPLE 47

1-{4-[4-(2-Dimethylaminoethoxy)benzoylamino]butyl}-1H-imidazo[4,5-c]quinoline-4-amine 0.14 g (0.314 mmol) of 1-{4-[4-(2-dimethylaminoethoxy)benzoylamino]butyl}-1H-imidazo[4,5-c]quinoline-4-amine shown below was obtained as pale yellowish white powder using as a starting material 0.13 g (0.621 mmol) of 4-(2-dimethylaminoethoxy)benzoic acid in the same manner as in Example 40.

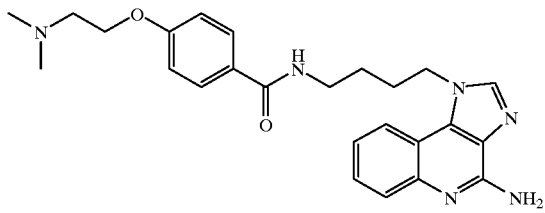

Its spectroscopic data are as follows:
IR (KBr) cm$^{-1}$: 3320, 2950, 1640, 1530, 1500, 1400, 1250, 1180, 1030, 840, 750.
$^1$H-NMR (CDCl$_3$) δ (ppm): 1.71 (2H, m), 2.09 (2H, m), 2.34 (6H, s), 2.74 (2H, t, J=5.6 Hz), 3.50 (2H, q, J=6.7 Hz), 4.10 (2H, t, J=5.8 Hz), 4.61 (2H, t, J=7.0 Hz), 5.45 (2H, br), 6.07 (1H, m), 6.92 (2H, d, J=9.2 Hz), 7.30 (1H, t, J=7.7 Hz), 7.52 (1H, t, J=7.7 Hz), 7.65 (2H, d, J=9.2 Hz), 7.83 (1H, d, J=8.4 Hz), 7.84 (1H, s), 7.94 (1H, d, J=8.2 Hz).

EXAMPLE 48

1-{4-[3-(2-Dimethylaminoethoxy)benzoylamino]butyl}-1H-imidazo[4,5-c]quinoline-4-amine 0.20 g (0.448 mmol) of 1-{4-[3-(2-Dimethylaminoethoxy)benzoylamino]butyl}-1H-imidazo[4,5-c]quinoline-4-amine shown below was obtained as faint yellowish white powder using 0.18 g (0.850 mmol) of 3-(2-dimethylaminoethoxy)benzoic acid as a starting material in the same manner as in Example 40.

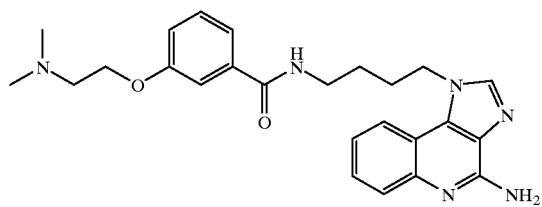

Its spectroscopic data are as follows:
IR (KBr) cm$^{-1}$: 3300, 2950, 1630, 1580, 1520, 1480, 1390, 1310, 1240, 760.
$^1$H-NMR (CDCl$_3$) δ (ppm): 1.72 (2H, m), 2.09 (2H, m), 2.33 (6H, s), 2.73 (2H, t, J=5.6 Hz), 3.51 (2H, q, J=6.7 Hz), 4.09 (2H, t, J=5.6 Hz), 4.61 (2H, t, J=7.2 Hz), 5.45 (2H, br), 6.18 (1H, m), 7.05 (1H, dd, J=8.4 Hz, 2.6 Hz), 7.20 (1H, d, J=8.2 Hz), 7.27~7.34 (3H, m), 7.52 (1H, t, J=7.7 Hz), 7.82 (1H, d, J=8.4 Hz), 7.85 (1H, s), 7.94 (1H, d, J=8.2 Hz).

EXAMPLE 49

1-(4-{3-[3-(2-Dimethylaminoethoxy)phenylpropanoylamino}butyl)-1H-imidazo[4,5-c]quinoline-4-amine 0.14 g (0.295 mmol) of 1-(4-{3-[3-(2-Dimethylaminoethoxy)phenylpropanoylamino}-butyl)-1H-imidazo[4,5-c]quinoline-4-amine shown below was obtained as faint yellowish white powder using 0.13 g (0.548 mmol) of 3-[3-(2-dimethylaminoethoxyphenyl]propionic acid as a starting material in the same manner as in Example 40.

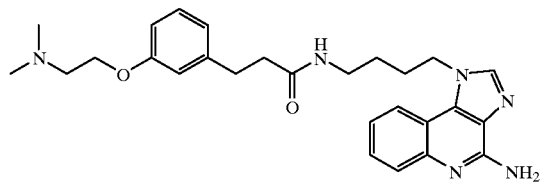

Its spectroscopic data are as follows:
IR (KBr) cm$^{-1}$: 3320, 2950, 1640, 1580, 1530, 1480, 1390, 1260, 1150, 760.
$^1$H-NMR (CDCl$_3$) δ (ppm): 1.50 (2H, m), 1.90 (2H, m), 2.31 (6H, s), 2.43 (2H, t, J=7.6 Hz), 2.69 (2H, t, J=5.8 Hz), 2.89 (2H, t, J=7.6 Hz), 3.25 (2H, q, J=6.5 Hz), 4.01 (2H, t, J=5.6 Hz), 4.52 (2H, t, J=7.0 Hz), 5.38 (1H, m), 5.50 (2H, br), 6.70~6.76 (3H, m),7.13 (1H, t, J=8.0 Hz), 7.33 (1H, t, J=7.6 Hz), 7.53 (1H, t, J=7.6 Hz), 7.80 (1H, s), 7.83 (1H, d, J=8.6 Hz), 7.91 (1H, d, J=8.4 Hz).

EXAMPLE 50

1-(4-{3-[4-(2-Dimethylaminoethoxy)-3-methoxyphenyl]propanoyl-amino}butyl)-1H-imidazo[4,5-c]quinoline-4-amine 0.14 g (0.277 mmol) of 1-(4-{3-[4-(2-Dimethylaminoethoxy)-3-methoxyphenyl]-propanoylamino}butyl)-1H-imidazo[4,5-c]quinoline-4-amine shown below was obtained as faint yellowish white powder using 0.15 g (0.561 mmol) of 3-[4-(2-dimethylaminoethoxy)-3-methoxyphenyl]propionic acid as a starting material in the same manner as in Example 40.

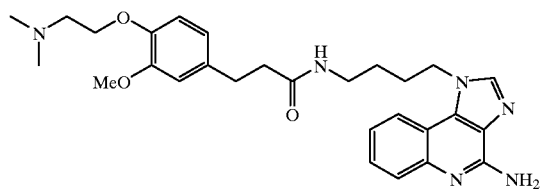

Its spectroscopic data are as follows:
IR (KBr) cm$^{-1}$: 3350, 2950, 1650, 1520, 1480, 1400, 1260, 1220, 1140, 1030, 760.
$^1$H-NMR (CDCl$_3$) δ (ppm): 1.51 (2H, m), 1.92 (2H, m), 2.32 (6H, s), 2.41 (2H, t, J=7.6 Hz), 2.74 (2H, t, J=6.0 Hz), 2.87 (2H, t, J=7.4 Hz), 3.25 (2H, q, J=6.5 Hz), 3.82 (3H, s), 4.04 (2H, t, J=6.2 Hz), 4.53 (2H, t, J=7.2 Hz), 5.35 (1H, m), 5.52 (2H, br), 6.66 (1H, d, J=8.2 Hz), 6.70 (1H, s), 6.76 (1H, d, J=8.4 Hz), 7.34 (1H, t, J=7.6 Hz), 7.53 (1H, t, J=7.8 Hz), 7.82 (1H, s), 7.83 (1H, d, J=8.0 Hz), 7.91 (1H, d, J=8.0 Hz).

EXAMPLE 51

1-{4-[6-(2-Dimethylaminoethoxy)-2-naphthoylamino}butyl)-1H-imidazo-[4,5-c]quinoline-4-amine 0.15 g (0.302 mmol) of 1-{4-[6-(2-Dimethylaminoethoxy)-2-naphtoylamino}butyl)-1H-imidazo-[4,5-c]quinoline-4-amine shown below was obtained as white powder using 0.14 g (0.540 mmol) of 6-(2-dimethylaminoethoxy)-2-naphtoeic acid as a starting material in the same manner as in Example 40.

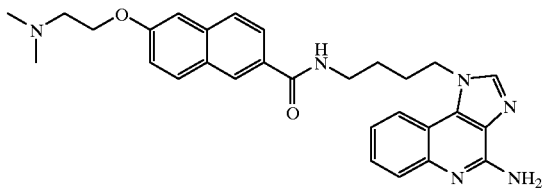
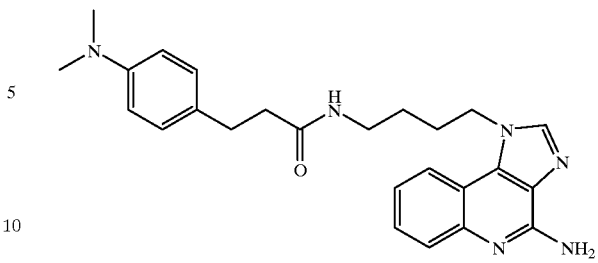

Its spectroscopic data are as follows:
IR (KBr) cm$^{-1}$: 3280, 3100, 2950, 1630, 1530, 1480, 1400, 1310, 1220, 1030, 750.
$^1$H-NMR (CDCl$_3$) δ (ppm): 1.76 (2H, m), 2.12 (2H, m), 2.37 (6H, s), 2.81 (2H, t, J=5.6 Hz), 3.57 (2H, q, J=6.7 Hz), 4.20 (2H, t, J=5.6 Hz), 4.62 (2H, t, J=7.0 Hz), 5.44 (2H, br), 6.29 (1H, m), 7.15 (1H, d, J=2.4 Hz), 7.23 (1H, dd, J=9.2 Hz, 2.4 Hz), 7.29 (1H, t, J=7.6 Hz), 7.50 (1H, t, J=7.8 Hz), 7.73 (2H, s), 7.76 (1H, d, J=9.2 Hz), 7.82 (1H, d, J=8.4 Hz), 7.86 (1H, s), 7.95 (1H, d, J=8.2 Hz), 8.14 (1H, s).

EXAMPLE 52
1-(4-{4-[4-(2-Dimethylaminoethoxy)phenyl]benzoylamino}butyl)-1H-imidazo-[4,5-c]quinoline-4-amine 0.16 g (0.318 mmol) of 1-(4-{4-[4-(2-Dimethylaminoethoxy)phenyl]benzoylamino}butyl)-1H-imidazo-[4,5-c]quinoline-4-amine shown below was obtained as faint yellowish white powder using 0.157 g (0.55 mmol) of 4-[4-(2-dimethylaminoethoxy)phenyl]benzoic acid as a starting material in the same manner as in Example 40.

Its spectroscopic data are as follows:
IR (KBr) cm$^{-1}$: 3320, 2930, 1640, 1520, 1480, 1400, 1350, 1250, 810, 760.
$^1$H-NMR (CDCl$_3$) δ (ppm): 1.50 (2H, m), 1.89 (2H, m), 2.41 (2H, t, J=7.4 Hz), 2.84 (2H, t, J=7.6 Hz), 2.86 (6H, s), 3.25 (2H, q, J=6.7 Hz), 4.50 (2H, t, J=7.2 Hz), 5.33 (1H, br), 5.47 (2H, br), 6.63 (2H, q, J=8.8 Hz), 7.03 (2H, d, J=8.8 Hz), 7.34 (1H, t, J=7.6 Hz), 7.53 (1H, t, J=7.7 Hz), 7.80 (1H, s), 7.83 (1H, d, J=8.4 Hz), 7.91 (1H, d, J=8.2 Hz).

EXAMPLE 54
1-{4-[O-(2-Dimethylaminoethyl)benzilylamino]butyl}-1H-imidazo-[4,5-c]quinoline-4-amine 13 mg (0.0242 mmol) of 1-{4-[O-(2-Dimethylaminoethyl)benzilylamino]butyl}-1H-imidazo-[4,5-c]quinoline-4-amine shown below was obtained as white powder using 0.165 g (0.55 mmol) of O-(2-dimethylaminoethyl)benzilic acid as a starting material in the same manner as in Example 40.

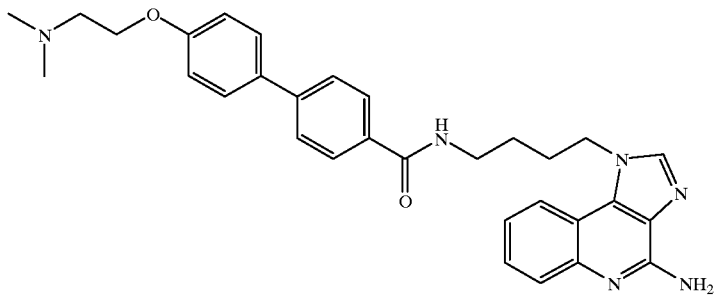

Its spectroscopic data are as follows:
IR (KBr) cm$^{-1}$: 3310, 2940, 1630, 1530, 1490, 1400, 1250, 1030, 830, 750.
$^1$H-NMR (CDCl$_3$) δ (ppm): 1.74 (2H, m), 2.11 (2H, m), 2.36 (6H, s), 2.76 (2H, t, J=5.8 Hz), 3.53 (2H, q, J=6.5 Hz), 4.12 (2H, t, J=5.6 Hz), 4.62 (2H, t, J=7.0 Hz), 5.43 (2H, s), 6.19 (1H, t, J=6.0 Hz), 7.01 (2H, d, J=8.8 Hz), 7.30 (1H, t, J=7.6 Hz), 7.52 (1H, t, J=7.7 Hz), 7.53 (2H, d, J=9.2 Hz), 7.58 (2H, d, J=8.8 Hz), 7.73 (2H, d, J=8.4 Hz), 7.83 (1H, d, J=8.6 Hz), 7.85 (1H, s), 7.94 (1H, d, J=8.4 Hz).

EXAMPLE 53
1-{4-[3-(4-Dimethylaminophenyl)propanoylamino]butyl}-1H-imidazo-[4,5-c]quinoline-4-amine 39 mg (0.0905 mmol) of 1-{4-[3-(4-Dimethylaminophenyl)propanoylamino]butyl}-1H-imidazo-[4,5-c]quinoline-4-amine shown below was obtained as yellowish white powder using 0.11 g (0.55 mmol) of 3-(4-dimethylaminophenyl)propionic acid as a starting material in the same manner as in Example 40.

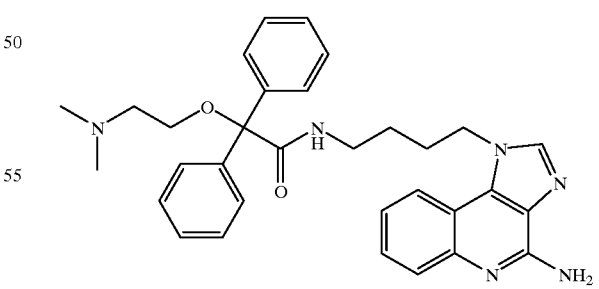

Its spectroscopic data are as follows:
IR (KBr) cm$^{-1}$: 3330, 3210, 1660, 1640, 1530, 1480, 1390, 1250, 1100, 760, 700.
$^1$H-NMR (CDCl$_3$) δ (ppm): 1.60 (2H, m), 1.85 (2H, m), 2.25 (6H, s), 2.50 (2H, t, J=4.8 Hz), 3.03 (2H, t, J=4.6 Hz), 3.38 (2H, q, J=6.3 Hz), 4.41 (2H, t, J=7.2 Hz), 5.57 (2H, br), 7.22~7.32 (6H, m), 7.32 (1H, t, J=7.7 Hz), 7.42~7.49 (4H, m), 7.53 (1H, t, J=7.6 Hz), 7.65 (1H, s), 7.83 (1H, d, J=8.4 Hz), 7.87 (1H, d, J=8.4 Hz), 9.12 (1H, br).

EXAMPLE 55
1-{4-[4-(4-Dimethylamino-1-phenyl-1-butenyl)benzoylamino]butyl}-1H-imidazo-[4,5-c]quinoline-4-amine 0.162 g (0.55 mmol) of 4-(4-Dimethylamino-1-phenyl-1-butenyl)benzoic acid was dissolved in 7 ml of chloroform, 80 µl (1.10 mmol) of thionyl chloride and one drop of N,N-dimethylformamide were added thereto, and the mixture was refluxed under heating for 4 hours. The reaction mixture was then concentrated under reduced pressure to obtain an crude product of acid chloride form.

0.128 g (0.50 mmol) of 1-(4-Aminobutyl)-1H-imidazo-[4,5-c]quinoline-4-amine was dissolved in a mixed solvent of 7 ml of ethanol and 4 ml of water and 0.55 ml of a 1N sodium hydroxide aqueous solution was added thereto. A solution of the acid chloride form product obtained above in 3 ml of chloroform was added dropwise to the above-obtained mixture under ice-cooling. The reaction mixture was stirred for 30 minutes, poured into a sodium hydrogencarbonate aqueous solution, and extracted twice with chloroform. The extract was dried (Na₂SO₄) and the solvent was distilled off. The resulting residue was purified by alminum column chromatography (chloform:methanol=200:1 to 30:1 (v/v)) and then silica gel chromatography (chloform:methanol=6:1 to 4:1 (v/v)). Finally, the purified product was triturated with ether and collected by filtration to obtain 0.152 g (0.285 mmol) of 1-{4-[4-(4-dimethylamino-1-phenyl-1-butenyl)benzoylamino]butyl}-1H-imidazo-[4,5-c]quinoline-4-amine (a mixture of E-form and Z-form) shown below as white powder.

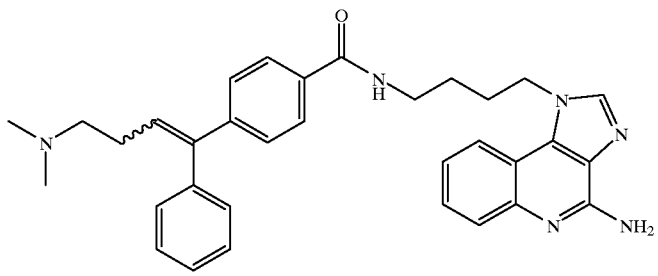

Its spectroscopic data are as follows:
IR (KBr) cm⁻¹: 3330, 2940, 1630, 1530, 1480, 1390, 1300, 1250, 850, 750, 700.
¹H-NMR (CDCl₃) δ (ppm): 1.73 (2H, m), 2.10 (2H, m), 2.19, 2.20 (6H, s×2), 2.29 (2H, m), 2.40 (2H, m), 3.52 (2H, m), 4.60, 4.63 (2H, t×2, J=7.0 Hz, 7.0 Hz), 5.46 (2H, br), 6.12, 6.19 (1H, br×2), 6.13, 6.18 (1H, t×2, J=7.4 Hz, 7.4 Hz), 7.16 (2H, t, J=8.1 Hz), 7.21~7.41 (6H, m), 7.51 (1H, m), 7.58, 7.70 (2H, d×2, J=8.8 Hz, 8.0 Hz), 7.82, 7.83 (1H, d×2, J=8.4 Hz, 8.4 Hz), 7.84, 7.86 (1H, s×2), 7.93, 7.95 (1H, d×2, J=9.0 Hz, 8.4 Hz).

EXAMPLE 56
1-{4-[4-(4-Dimethylamino-1-phenylbutyl)benzoylamino]butyl}-1H-imidazo-[4,5-c]quinoline-4-amine 65 mg (0.122 mmol) of 1-{4-[4-(4-Dimethylamino-1-phenylbutyl)benzoylamino]butyl}-1H-imidazo-[4,5-c]quinoline-4-amine shown below was obtained as white powder using 0.164 g (0.55 mmol) of 4-(4-dimethylamino-1-phenylbutyl)benzoic acid as a starting material in the same manner as in Example 55.

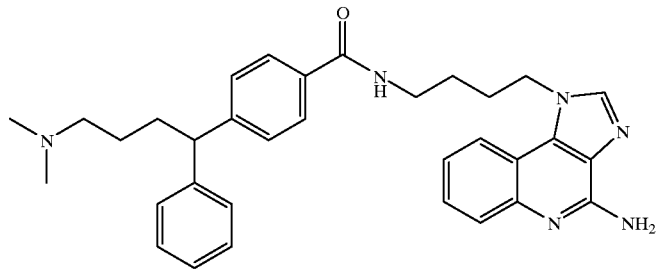

Its spectroscopic data are as follows:
IR (KBr) cm⁻¹: 3330, 2940, 1630, 1530, 1480, 1400, 1310, 1250, 760, 700.
¹H-NMR (CDCl₃) δ (ppm): 1.42 (2H, m), 1.70 (2H, m), 2.07 (4H, m), 2.17 (6H, s), 2.29 (2H, t, J=7.2 Hz), 3.49 (2H, q, J=6.4 Hz), 3.93 (1H, t, J=8.0 Hz), 4.59 (2H, t, J=7.4 Hz), 5.50 (2H, br), 6.11 (1H, t, J=5.6 Hz), 7.15~7.31 (8H, m), 7.48 (1H, t, J=7.7 Hz), 7.60 (2H, d, J=8.8 Hz), 7.82 (1H, d, J=8.2 Hz), 7.83 (1H, s), 7.92 (1H, d, J=8.2 Hz).

EXAMPLE 57
1-{4-[4-(N-(2-dimethylaminoethyl)phenylamino]benzoylamino}-butyl)-1H-imidazo-[4,5-c]quinoline-4-amine 22 mg (0.0421 mmol) of 1-{4-[4-(N-(2-dimethylaminoethyl)phenylamino]benzoylamino}-butyl)-1H-imidazo-[4,5-c]quinoline-4-amine (shown below was obtained as faint yellowish white powder using 0.156 g (0.55 mmol) of 4-[N-(2-dimethylaminoethyl)phenylamino]benzoic acid as a starting material in the same manner as in Example 55.

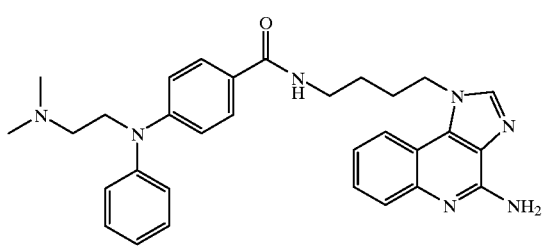

Its spectroscopic data are as follows:
IR (KBr) cm$^{-1}$: 3310, 2940, 1630, 1590, 1530, 1510, 1400, 1290, 1260, 760, 700.
$^1$H-NMR (CDCl$_3$) δ (ppm): 1.71 (2H, m), 2.08 (2H, m), 2.27 (6H, s), 2.57 (2H, t, J=7.6 Hz), 3.50 (2H, q, J=6.5 Hz), 3.86 (2H, t, J=7.6 Hz), 4.61 (2H, t, J=7.2 Hz), 5.53 (2H, br), 6.01 (1H, t, J=6.0 Hz), 6.76 (2H, d, J=9.2 Hz), 7.19 (3H, m), 7.30 (1H, t, J=7.6 Hz), 7.38 (2H, t, J=8.0 Hz), 7.51 (1H, t, J=7.8 Hz), 7.54 (2H, d, J=8.8 Hz), 7.82 (1H, d, J=8.4 Hz), 7.85 (1H, s) 7.94 (1H, d, J=8.4 Hz).

EXAMPLE 58

1-(4-{4-[N-(3-dimethylaminopropyl)phenylamino]benzoylamino}-butyl)-1H-imidazo-[4,5-c]quinoline-4-amine 54 mg (0.101 mmol) of 1-(4-{4-[N-(3-dimethylaminopropyl)phenylamino]benzoylamino}-butyl)-1H-imidazo-[4,5-c]quinoline-4-amine shown below was obtained as pale yellowish white powder using 0.164 g (0.55 mmol) of 4-[N-(3-dimethylaminopropyl)phenylamino]benzoic acid as a starting material in the same manner as in Example 55.

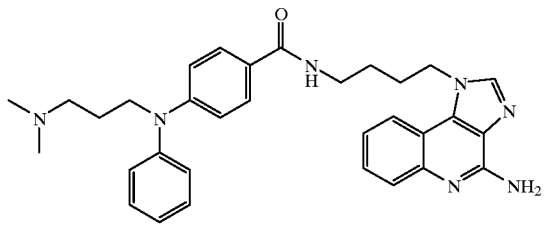

Its spectroscopic data are as follows:
IR (KBr) cm$^{-1}$: 3300, 2940, 1610, 1590, 1530, 1510, 1400, 1310, 1250, 760.
$^1$H-NMR (CDCl$_3$) δ (ppm): 1.71 (2H, m), 1.83 (2H, m), 2.08 (2H, m), 2.22 (6H, s), 2.33 (2H, t, J=7.2 Hz), 3.50 (2H, m), 3.78 (2H, t, J=7.4 Hz), 4.61 (2H, t, J=7.2 Hz), 5.65 (2H, br), 6.03 (1H, br), 6.76 (2H, d, J=8.8 Hz), 7.15~7.22 (3H, m), 7.31 (1H, t, J=7.6 Hz), 7.38 (2H, t, J=7.8 Hz), 7.52 (1H, t, J=7.4 Hz), 7.54 (2H, d, J=8.8 Hz), 7.83 (1H, d, J=8.0 Hz), 7.86 (1H, s), 7.94 (1H, d, J=8.0 Hz).

EXAMPLE 59

1-(4-{[α-(2-Dimethylaminoethoxy)-α-phenyl-p-toluoyl]amino}butyl)-2-methyl-1H-imidazo-[4,5-c]quinoline-4-amine 36 mg (0.0653 mmol) of 1-(4-{[α-(2-Dimethylaminoethoxy)-α-phenyl-p-toluoyl]amino}-butyl)-2-methyl-1H-imidazo-[4,5-c]quinoline-4-amine shown below was obtained as faint yellowish white powder using 67 mg (0.224 mmol) of α-(2-dimethylaminoethoxy)-α-phenyl-p-toluic acid and 55 mg (0.204 mmol) of 1-(4-aminobutyl)-2-methyl-1H-imidazo-[4,5-c]quinoline-4-amine as starting materials in the same manner as in Example 55.

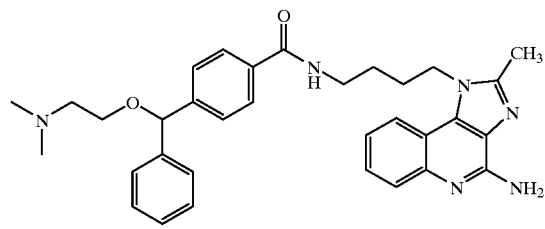

Its spectroscopic data are as follows:
IR (KBr) cm$^{-1}$: 3320, 2940, 1630, 1540, 1480, 1430, 1380, 1310, 1100, 750, 700.
$^1$H-NMR (CDCl$_3$) δ (ppm): 1.77 (2H, m), 2.02 (2H, m), 2.27 (6H, s), 2.60 (2H, t, J=5.8 Hz), 2.65 (3H, s), 3.50 (2H, q, J=6.7 Hz), 3.56 (2H, td, J=6.0 Hz, 2.4 Hz), 4.50 (2H, t, J=7.6 Hz), 5.39 (1H, s), 5.54 (2H, br), 6.13 (1H, t, J=5.8 Hz), 7.22~7.34 (6H, m), 7.41 (2H, d, J=8.4 Hz), 7.45 (1H, t, J=7.8 Hz), 7.63 (2H, d, J=8.0 Hz), 7.81 (1H, d, J=8.4 Hz), 7.89 (1H, d, J=8.0 Hz).

EXAMPLE 60

1-(4-{[α-(2-Dimethylaminoethoxy)-α-phenyl-p-toluoyl]amino}butyl)-2-ethoxymethyl-1H-imidazo-[4,5-c]quinoline-4-amine 0.128 g (0.215 mmol) of 1-(4-{[α-(2-Dimethylaminoethoxy)-α-phenyl-p-toluoyl]amino}-butyl)-2-ethoxymethyl-1H-imidazo-[4,5-c]quinoline-4-amine shown below was obtained as faint yellowish white powder using 0.165 g (0.55 mmol) of α-(2-dimethylaminoethoxy)-α-phenyl-p-toluic acid and 0.157 g (0.50 mmol) of 1-(4-aminobutyl)-2-ethoxymethyl-1H-imidazo-[4,5-c]quinoline-4-amine as starting materials in the same manner as in Example 55.

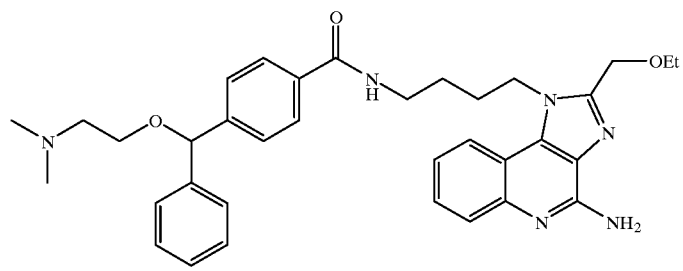

Its spectroscopic data are as follows:
IR (KBr) cm$^{-1}$: 3300, 2940, 1630, 1540, 1480, 1440, 1390, 1310, 1100, 760, 700.
$^1$H-NMR (CDCl$_3$) δ (ppm): 1.20 (3H, t, J=7.0 Hz), 1.82 (2H, m), 2.07 (2H, m), 2.27 (6H, s), 2.60 (2H, t, J=6.0 Hz), 3.52 (2H, q, J=6.4 Hz), 3.56 (2H, td, J=5.9 Hz, 2.5 Hz), 3.59 (2H, q, J=7.1 Hz), 4.62 (2H, t, J=8.0 Hz), 4.79 (2H, s), 5.39 (1H, s), 5.50 (2H, br), 6.18 (1H, t, J=5.9 Hz), 7.22~7.34 (6H, m), 7.40 (2H, d, J=8.4 Hz), 7.46 (1H, t, J=7.7 Hz), 7.64 (2H, d, J=8.4 Hz), 7.80 (1H, d, J=8.4 Hz), 7.91 (1H, d, J=8.0 Hz).

EXAMPLE 61
Production of ointment containing 0.2% of the compound of Example 40

| Preparation: An ointment containing the compound of the present invention was prepared in the following manner | |
|---|---|
| Compound of Example 40 | 0.02 g |
| Sorbitan monolaurate (SP-20) | 2.0 g |
| White petrolatum | 7.98 g |
| Total amount | 10.0 g |

0.02 g of The compound of the present invention was added to 2 g of SP-20 maintained at 80° C. and the mixture was stirred to dissolve the compound. 7.98 g of white petrolatum separately melted by heating (80° C.) was added thereto and the mixture was cooled to room temperature with stirring.

EXAMPLE 62
Production of ointment containing 2% of the compound of Example 40

| Preparation: An ointment containing the compound of the present invention was prepared in the following manner | |
|---|---|
| Compound of Example 40 | 0.2 g |
| Sorbitan monolaurate (SP-20) | 2.0 g |
| White petrolatum | 7.8 g |
| Total amount | 10.0 g |

0.2 g of the compound of the present invention was added to 2 g of SP-20 maintained at 80° C. and the mixture was stirred to dissolve the compound. 7.8 g of white petrolatum separately melted by heating (80° C.) was added thereto and the mixture was cooled to room temperature with stirring.

COMPARATIVE EXAMPLE 1
Production of ointment containing 2% Imiquimod 0.5 g of Imiquimod synthesized by the method described in U.S. Pat. No. 4,988,815 was added to 5 g of isostearic acid maintained at 80° C. and dissolved by stirring. 19.5 g of white petrolatum separately melted by heating (80° C.) was added thereto and the mixture was cooled to room temperature with stirring.

COMPARATIVE EXAMPLE 2
External preparation containing betamethasone valerate 0.12% Rinderon V ointment (Shionogi) was used as it was.

EXAMPLE 63
Measurement of interferon functions
Test method
(1) Preparation of mononuclear cell fraction A 8-ml portion of peripheral blood collected from three human subjects (adult females) was immediately distributed into a Leukoprep tube (tubes for separating leukocytes, Falcon). The resulting Leukoprep tubes were subjected to centrifugation (BECKMAN CS-6KR, 20° C., 3,000 rpm, 30 minutes) and the mononuclear cell phase was recovered. The mononuclear cell phase was washed twice with RPMI-1640 medium (containing 10% fetal calf serum, penicillin-streptomycin, hereinafter referred to as RPMI-1640 medium) and adjusted to give a cell density of 1.3×10$^6$ cells/ml with RPMI-1640 medium.

(2) Preparation of each test drug

The compounds of the present invention were dissolved in DMSO and the solutions were each added to RPMI-1640 medium. The concentration of the drug was adjusted to 40 μM, 12.8 μM, 4 μM, and 1.28 μM.

(3) Interferon induction test

A 150 μl portion of the cells (1.3×10$^6$ cells/ml) prepared by the method as described above was added to each well of a 96-well plate (Corning). A 50 μl portion of the drug prepared by the method as described above was added thereto and the plate was incubated in a CO$_2$ incubator for 24 hours in the case of IFN-α and 96 hours in the case of IFN-γ (final drug concentrations: 10 μM, 3.2 μM, 1 μM, and 0.32 μM, final DMSO concentrations: 0.05 to 0.1%). After completion of the incubation, the cell suspension was transferred to a microtube and centrifuged at 8,000 rpm for 10 minutes to recover a supernatant. The resulting supernatant was subjected to IFN determination by ELISA using a human interferon-α determination kit (Otsuka Pharmaceutical) and a human interferon-γ determination kit (BioSource International).

Results

The activities of inducing interferon from human peripheral blood mononuclear cells of Imiquimod and the compounds of the present invention are shown in Tables 1 and 2.

Many of the compounds of the examples exhibited interferon-inducing activity comparable to or more than that of Imiquimod. Particularly, the compound of Example 40 showed about 100 times as high IFN-α and IFN-γ inducing activity as Imiquimod.

TABLE 1

Induction of interferon-α in human cells

| Test compounds | IFN-α levels (IU/ml) Concentration administered (μM) | | | | | | |
|---|---|---|---|---|---|---|---|
| | 0.01 | 0.032 | 0.1 | 0.32 | 1 | 3.2 | 10 |
| Imiquimod | | | | 0.5 | 1.0 | 39.9 | 40.2 |
| Example 40 | 0.8 | 24.4 | 61.3 | 93.4 | 81.6 | 36.8 | 4.1 |
| Example 41 | 0.7 | 0.9 | 43.5 | 51.3 | 78.1 | 40.5 | 1.9 |
| Example 42 | 1.6 | 40.2 | 83.8 | 75.3 | 28.9 | 2.1 | 0.7 |
| Example 43 | | | 29.1 | 111.6 | 41.2 | 2.1 | 0.1 |
| Example 44 | | | 40.2 | 52.3 | 14.1 | 1.3 | 0.0 |
| Example 45 | 0.1 | 0.7 | 19.2 | 13.4 | 0.4 | 0.1 | 0.1 |
| Example 46 | | | 0.3 | 61.9 | 92.0 | 67.2 | 55.3 |
| Example 47 | | | 21.0 | 91.0 | 89.5 | 83.9 | 72.9 |
| Example 48 | | | 65.4 | 108.5 | 82.5 | 53.9 | 23.5 |
| Example 49 | | | 1.8 | 38.2 | 45.1 | 109.6 | 45.9 |
| Example 50 | | | 0.0 | 0.1 | 37.8 | 73.5 | 41.6 |
| Example 51 | 11.9 | 55.9 | 96.7 | 17.9 | 3.4 | 1.0 | 0.0 |
| Example 52 | | 6.8 | 25.0 | 7.6 | 0.4 | 0.3 | |
| Example 53 | 0.6 | 2.2 | 0.2 | 1.3 | 58.8 | 186.2 | 105.2 |
| Example 55 | 3.7 | 23.5 | 88.5 | 73.2 | 40.1 | 1.8 | 0.3 |
| Example 58 | 1.6 | 7.4 | 146.7 | 157.6 | 92.3 | 47.1 | |

DMSO (reference solvent): 0.1 to 0.7 (IU ml)
PolyI: 100 μg/ml of C induced 10.0 IU/ml of IFN-α

TABLE 2

Induction of interferon-γ in human cells

| Test compounds | IFN-γ levels (pg/ml) Concentration administered (μM) | | | | | | |
|---|---|---|---|---|---|---|---|
| | 0.01 | 0.032 | 0.1 | 0.32 | 1 | 3.2 | 10 |
| Imiquimod |  |  |  | 683.8 | 639.2 | 1228.4 | 1196.1 |
| Example 40 | 496.6 | 778.9 | 1179.9 | 1660.8 | 2287.7 | 1265.2 | 115.2 |
| Example 41 | 188.2 | 402.7 | 192.3 | 412.3 | 615.0 | 843.6 | 1646.4 |
| Example 42 |  |  | 600.6 | 309.4 | 767.1 | 657.6 | 0.0 |
| Example 43 |  |  | 1148.0 | 1274.5 | 1743.6 | 1727.5 | 147.1 |
| Example 44 |  |  | 785.3 | 1271.6 | 1703.9 | 820.1 | 0.5 |
| Example 46 |  |  | 197.1 | 92.9 | 184.1 | 845.9 | 1477.1 |
| Example 47 |  |  | 197.1 | 407.6 | 720.0 | 1066.5 | 1598.2 |
| Example 48 |  |  | 645.1 | 1365.7 | 1812.3 | 2428.9 | 2692.6 |
| Example 49 |  |  | 963.2 | 810.3 | 915.2 | 1552.5 | 2324.0 |
| Example 50 |  |  | 641.7 | 811.8 | 768.6 | 1264.2 | 2180.9 |

DMSO (reference solvent): 314.4 to 590.2 pg/ml
10 μg/ml of Con A induced 4396.8 to 2017.1 pg/ml of IFN-γ

EXAMPLE 64

Eosinophilic leukocyte skin infiltration-inhibiting effect (1) Test method

Four-week-old Balb/c mice (male) were purchased from Nippon Crea. The mice were tamed under conditions of room temperature of 23±2° C., humidity of 50±10% (irradiation time, 8:00 to 20:00) for more than one week and then subjected to the test. The test was carried out under non-fasting conditions and the mice was allowed to freely take water and feed during the test period after the test compound was administered (the weight during the test: 18 to 32 g).

(1) Sensitization and challenge

RO water (3.8 ml) and physiological saline (1.2 ml) were added to an amount of 10 mg protein of mite extract-Dp (Cosmo Bio) to prepare a solution of a concentration of 2 mg protein/ml (undiluted solution). The undiluted solution was adjusted to have a concentration of 500 μg protein/ml using physiological saline and a one-fortieth amount of a Bordetella pertussis solution was added thereto to serve as a sensitization solution. Sensitization was performed by subcutaneously administering 200 μl of the sensitization solution to the cervical region of the mice using Myjector (Terumo). The sensitization was performed three times including the first sensitization every seven days by the above method. Twenty-one days after the first sensitization, challenge was carried out by subcutaneously administering on the back of the mice using Myjector (Termo) 50 μl of the mite antigen solution that had been adjusted with a 0.9% sodium chloride aqueous solution to give a concentration of 200 μg protein/ml.

(2) Recovery of skin and observation of pathological specimen

Forty-eight hours after the challenge, the mice were sacrificed by cervical dislocation. Their skin on the back was peeled off and the skin was cut by 1 cm square taking the marking site as a center. The recovered skin was placed in 10% neutral formarin buffer (using 15-ml centrifugation tube manufactured by Corning) and fixed by allowing it to stand at room temperature for one day or longer. The fixed skin was made into a paraffin section by the conventional method and subjected to Runa staininig. (Two sites, namely the center of the skin sample and 2 mm upper site from it toward the head, were cut off in the vertical direaction of the axis.) The number of eosinophilic leukocytes per 1 cm of one section under optical microscopic observation of the specimen (400-fold magnification).

The inhibitory effect of the drug was caluculated by the following equation:

Inhibitory rate (%)={(number of eosinophilic leukocytes in the base-administered group−number of eosinophilic leukocytes in the test compound-administered group)/number of eosinophilic leukocytes in the base-administered group}×100

(3) Preparation of each test drug

Preparation of 2% Imiquimod ointment

Imiquimod (0.5 g), which had been synthesized by the method as described in U.S. Pat. No. 4,988,815, was added to 5 g of isostearic acid maintained at 80° C. and the mixture was stirred to dissolve the drug. White petrolatum (19.5 g) that had been melted by heating (80° C.) was added thereto and the mixture was cooled to room temperature with stirring.

Preparation of ointment containing 0.2% of the compound of Example 40

The titled ointment was prepared by the method of Example 61.

External preparation of betamethasone valerate 0.12% Rinderon V ointment (Shionogi) was used as it was.

(4) Method of administrating drugs

Percutaneous administration (Occlusive dressing technique (ODT)

Mice were anesthetized with ether and their hair at the center of the back was cut with an electric clipper so as not to hurt the skin. The portion to be subjected to challenge at the center on the back was marked with oil ink in advance. Before the challenge, a drug (test compound) was coated within 3 cm square with the marked portion on the back as the center. In contrast, after the challenge with a mite, the drug was coated within 2 cm square with the challenge site as the center. A lap was layered thereon to cover the coated portion and fixed with an elastic tape (Elascotin, Johnson & Johnson Medical Inc.). Only a base was coated for the control group.

The dose of the drug was 50 mg per animal. The drug was administered for consecutive four days from the day before the challenge as shown in the following schedule:

Two days before the challenge→the day of challenge (immediately after challenge)→the next day of the challenge (three times in total)

(2) Results

Table 3 shows an inhibitory effect of the 2% Imiquimod ointment, ointment of 2% of the compound of Example 40, and 0.12% betamethasone valerate ointment on the mite-induced eosinophilic leukocyte infiltration to mouse skin. The ointment of the compound of Example 40 inhibited the eosinophilic leukocyte infiltration at the level comparable to the betamethasone valerate ointment.

TABLE 3

Inhibitory effect on mite-challenged eosinophilic leukocyte infiltration to mouse skin

| Drug administered and its dose | Number of cases | Number of eosinophilic leukocytes (cells/cm) | Inhibitory rate (%) |
| --- | --- | --- | --- |
| Non-sensitized animals | | | |
| Non-challenge Sensitized animals Challenge by a mite | 3 | 12.0 ± 3.0 | — |
| Base ointment | 7 | 679.57 ± 149.98 | — |
| 2% Imiquimod ointment | 4 | 111.50 ± 30.38 | 83.59 |
| Ointment of 0.2% of the compound of Example 40 | 8 | 164.63 ± 33.43 | 75.77 |
| 0.12% betamethasone valerate ointment | 8 | 108.75 ± 24.99 | 84.00 |

The number of eosinophilic leukocytes in each group two days after the challenge was shown by mean ±S.D.

EXAMPLE 65

Percutaneous absorbability (1) Test method

Four-week old hairless mice (male) were perchased from Nippon Crea and subjected to the test after a one-week taming period. The percutaneous absorbability test was carried out in accordance with the method of Tomohiro Hikima et al. (Yakuzaigaku (Pharmacoloty) 55(2), 122–126, 1995). The unhurt skin (intact skin) on the back of the mice was cut off and set on a vertical 2-cell type membrane permeation test device (VIDREZX). The 2% Imiquimod ointment and the ointment of 2% of the test compound (300 mg) were applied on the skin of the donor cells and the receptor cells were filled with PBS containing penicillin (50 U/ml) and streptomycin (50 ug/ml). The receptor solution was maintained at the constant temperature (37° C.) to perform the permeation test. A 100 μl portion of the test solution was sampled from the sampling outlet with the passage of time and the drug in the sample was determined by HPLC. The rate of drug permeation to the skin was calculated by the results.

(2) Results

As shown in Table 4, the permeation rate of the ointment of 2% of the compound of Example 40 to the hairless mouse skin was found to be about 14 times as fast as that of the 2% Imiquimod ointment in the case of using the intact skin.

TABLE 4

Percutaneous permeability

| Drug administered | Rate drug permeation to intact skin ($\mu g/cm^2/hr$) |
| --- | --- |
| 2% Imiquimod | 0.07 |
| Ointment of 2% of the compound of Example 40 | 0.98 |

INDUSTRIAL APPLICABILITY

As described above, the present invention provides novel amide derivatives. The amide derivatives of the present invention have a potent interferon ($\alpha,\gamma$)-inducing activity and excellent percutaneous absorbability and are useful for therapy of various tumors, viral diseases, and particularly allergic inflammatory diseases such as atopic dermatitis by an eosinophilic leukocyte skin infiltration inhibitory effect.

What is claimed is:

1. An amide derivative represented by the formula (I) and its pharmaceutically acceptable acid addition salt:

$$R_1R_2N\text{---}(CH_2)g\text{---}(X)h\text{---}(CH_2)i\text{---}(Y)j\text{---}(CH_2)k\text{---}$$
$$\text{---}(Z)l\text{---}(CH_2)m\text{---}COHN\text{---}(CH_2)n\text{---} \quad \text{[imidazoquinoline structure]}$$

(I)

wherein the formula (I), $R_1$ and $R_2$ are independently a branched or unbranched $C_{1-6}$ alkyl;

X is a member selected from the group consisting of —O—, —NR$_4$—, —CR$_5$=CR$_6$—, and S(O)$_p$; wherein R$_4$ is at least a member selected from

[phenyl-R$_{15}$ structure]

pyridyl, and a branched or unbranched $C_{1-8}$ alkyl; $R_{15}$ is a member selected from the group consisting of hydrogen, a $C_{1-8}$ alkyl, hydroxyl, hydroxycarbonyl, a $C_{1-8}$ alkoxy, a $C_{1-8}$ alkoxycarbonyl, and a halogen; $R_5$ and $R_6$ are independently hydrogen and phenyl; and p is an integer of 0 to 2;

Y is selected from —CR$_7$R$_8$— and phenylene; wherein R$_7$ is at least a member selected from

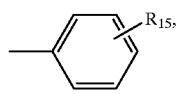

pyridyl, and a branched or unbranched $C_{1-8}$ alkyl; $R_8$ is hydrogen or phenyl; and $R_{15}$ is a member selected from the group consisting of hydrogen, a $C_{1-8}$ alkyl, hydroxyl, hydroxycarbonyl, a $C_{1-8}$ alkoxy, a $C_{1-8}$ alkoxycarbonyl, and a halogen;

Z is selected from

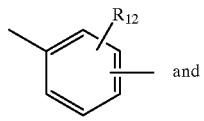 and 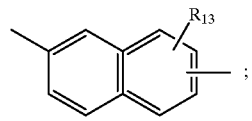 ;

wherein $R_{12}$ and $R_{13}$ are independently a member selected from the group consisting of hydrogen, a $C_{1-8}$ alkyl, hydroxyl, hydrocarbonyl, a $C_{1-8}$ alkoxy, a $C_{1-8}$ alkoxycarbonyl and a halogen;

h, j and l are an integer of 0 or 1;

m is an integer of 0 to 5;

n is an integer of 2 to 12;

g, i and k are an integer of 0 to 6; and $R_3$ is a member selected from the group consisting of hydrogen, phenyl, a branched or unbranched $C_{1-8}$ alkyl and —$(CH_2)_r R_{14}$; wherein r is an integer of 1 to 8, and $R_{14}$ is a member selected from the group consisting of phenyl, phenoxy, benzyloxy, a $C_{1-8}$ alkoxy, amino, a $C_{1-8}$ alkylamino, hydroxycarbonyl and a $C_{1-8}$ alkoxycarbonyl.

2. An amide derivative and its pharmaceutically acceptable acid addition salt according to claim 1 wherein:

$R_1$ and $R_2$ are independently a branched or unbranched $C_{1-6}$ alkyl;

X is a member selected from the group consisting of —O—, —$NR_4$— wherein $R_4$ is phenyl, and —$CR_5$=$CR_6$— wherein $R_5$ and $R_6$ are independently hydrogen or phenyl;

Y is

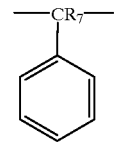

wherein $R_7$ is hydrogen or phenyl, and phenylene;

Z is selected from

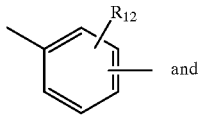 and 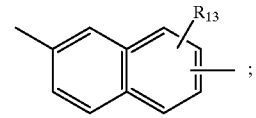 ;

wherein $R_{12}$ and $R_{13}$ are independently a member selected from the group consisting of hydrogen, a $C_{1-8}$ alkyl, hydroxyl, a $C_{1-8}$ alkoxy, and a halogen; and $R_3$ is a member selected from the group consisting of hydrogen, phenyl, a branched or unbranched $C_{1-8}$ alkyl and —$(CH_2)_r R_{14}$; wherein r is an integer of 1 to 8, and $R_{14}$ is a member selected from the group consisting of phenyl, phenoxy, benzyloxy, and a $C_{1-8}$ alkoxy.

3. An amide derivative and its pharmaceutically acceptable acid addition salt according to claim 2 wherein h is 1.

4. A pharmaceutical composition comprising the compound of formula (I) according to claim 1 and a suitable pharmaceutical carrier.

* * * * *

UNITED STATES PATENT AND TRADEMARK OFFICE
CERTIFICATE OF CORRECTION

Page 1 of 2

PATENT NO. : 6,069,149
DATED : May 30, 2000
INVENTOR(S) : R. Nanba, et al.

It is certified that error appears in the above-identified patent and that said Letters Patent is hereby corrected as shown below:

On the title page, item:

[30] Foreign Application Priority Data
Jan. 9, 1997 [JP] Japan ..................... 9-002375

[54] NOVEL AMIDE DERIVATIVES AND INTERMEDIATES FOR THE SYNTHESIS THEREOF

Column 3, line 40, delete "$R_3$" and insert --$R_3'$--

Column 4, line 29, delete "$R_3$" and insert --$R_3'$--

Column 10, line 38, after "for" insert --example, N,N-dimethylformamide, dimethylsulfoxide, chloroform, methylene chloride, toluene, benzene, tetrahydrofuran, dioxane,--

Column 10, lines 65-67 are deleted.

Column 11, line 11, delete "$R_2$" and insert --$R_{12}$--.

Column 19, line 60, delete "abrown" and insert --a brown--.

Column 22, line 10, delete "$^1$-NMR" and insert --$^1$-H-NMR--

Column 22, line 19, delete "acid".

Column 22, line 22, delete "(ppm) 2.23" and insert --(ppm) : 2.23--.

Column 25, line 31, delete "($^1$H" and insert --(1H--.

Column 26, line 26, delete "($^1$H" and insert --(1H--.

Column 28, line 49, at the end of the line, the second "H," is deleted.

Column 29, line 16, delete "5 (ppm)" and insert --δ (ppm)--.

UNITED STATES PATENT AND TRADEMARK OFFICE
CERTIFICATE OF CORRECTION

PATENT NO. : 6,069,149
DATED : May 30, 2000
INVENTOR(S) : R. Nanba, et al.

It is certified that error appears in the above-identified patent and that said Letters Patent is hereby corrected as shown below:

Column 31, line 50, delete "(1H, H, br)" and insert --(1H, br)--.

Column 32, line 65, delete "(shown below)" and after "-4-amine" insert --(shown below)--

Signed and Sealed this

Eighth Day of May, 2001

*Attest:*

NICHOLAS P. GODICI

*Attesting Officer*  Acting Director of the United States Patent and Trademark Office